United States Patent
Sharei et al.

(10) Patent No.: US 11,111,472 B2
(45) Date of Patent: Sep. 7, 2021

(54) DELIVERY OF BIOMOLECULES TO IMMUNE CELLS

(71) Applicants: Massachusetts Institute of Technology, Cambridge, MA (US); President and Fellows of Harvard College, Cambridge, MA (US)

(72) Inventors: Armon R. Sharei, Watertown, MA (US); Shirley Mao, Cambridge, MA (US); George Hartoularos, Boston, MA (US); Sophia Liu, Boston, MA (US); Megan Heimann, Baltimore, MD (US); Pamela Basto, Somerville, MA (US); Gregory Szeto, Baltimore, MD (US); Siddharth Jhunjhunwala, Bengaluru (IN); Darrell Irvine, Arlington, MA (US); Robert S. Langer, Newton, MA (US); Klavs F. Jensen, Lexington, MA (US); Ulrich H. Von Andrian, Chestnut Hill, MA (US)

(73) Assignees: Massachusetts Institute of Technology, Cambridge, MA (US); President and Fellows of Harvard College, Cambridge, MA (US)

(*) Notice: Subject to any disclaimer, the term of this patent is extended or adjusted under 35 U.S.C. 154(b) by 0 days.

(21) Appl. No.: 15/523,142

(22) PCT Filed: Oct. 30, 2015

(86) PCT No.: PCT/US2015/058489
§ 371 (c)(1),
(2) Date: Apr. 28, 2017

(87) PCT Pub. No.: WO2016/070136
PCT Pub. Date: May 6, 2016

(65) Prior Publication Data
US 2018/0142198 A1    May 24, 2018

Related U.S. Application Data

(60) Provisional application No. 62/073,548, filed on Oct. 31, 2014.

(51) Int. Cl.
*C12M 1/42* (2006.01)
*C12M 3/06* (2006.01)
(Continued)

(52) U.S. Cl.
CPC ............. *C12M 35/04* (2013.01); *A61K 39/00* (2013.01); *A61K 45/06* (2013.01);
(Continued)

(58) Field of Classification Search
CPC ........... A61K 39/00; A61K 2039/5158; A61K 45/06; A61K 49/0017; C12N 5/0636;
(Continued)

(56) References Cited

U.S. PATENT DOCUMENTS

| 4,055,799 A | 10/1977 | Coster |
| 4,835,457 A | 5/1989 | Hanss |

(Continued)

FOREIGN PATENT DOCUMENTS

| CN | 101031339 A | 9/2007 |
| CN | 101031641 A | 9/2007 |

(Continued)

OTHER PUBLICATIONS

Rughetti et al. Transfected human dendritic cells to induce antitumor immunity. Gene Therapy (2000), v7, p. 1458-1466. (Year: 2000).*

(Continued)

*Primary Examiner* — Sean C. Barron
(74) *Attorney, Agent, or Firm* — Wolf, Greenfield & Sacks, P.C.

(57) ABSTRACT

A method and device for preferentially delivering a compound such as an antigen to the cytosol of an immune cell.

(Continued)

The method comprises passing a cell suspension comprising the target immune cell through a microfluidic device and contacting the suspension with the compound(s) or payload to be delivered.

145 Claims, 42 Drawing Sheets

Specification includes a Sequence Listing.

(51) Int. Cl.
*A61K 39/00* (2006.01)
*A61K 45/06* (2006.01)
*A61K 49/00* (2006.01)
*C12N 15/87* (2006.01)
*G01N 33/50* (2006.01)
*C12N 5/0781* (2010.01)
*C12N 5/0783* (2010.01)
*C12N 5/0784* (2010.01)

(52) U.S. Cl.
CPC ......... *A61K 49/0017* (2013.01); *C12M 23/16* (2013.01); *C12M 35/00* (2013.01); *C12N 5/0635* (2013.01); *C12N 5/0636* (2013.01); *C12N 5/0639* (2013.01); *C12N 15/87* (2013.01); *G01N 33/5047* (2013.01); *A61K 2039/5158* (2013.01); *C12N 2501/05* (2013.01); *C12N 2501/998* (2013.01); *C12N 2510/00* (2013.01); *C12N 2527/00* (2013.01)

(58) Field of Classification Search
CPC ............ C12N 2527/00; C12N 2501/05; C12N 2501/998; C12N 2510/00; C12N 5/0639; C12N 5/0635; C12N 15/87; G01N 33/5047; C12M 35/04; C12M 23/16
See application file for complete search history.

(56) References Cited

U.S. PATENT DOCUMENTS

| | | |
|---|---|---|
| 5,023,054 A | 6/1991 | Sato et al. |
| 5,643,577 A | 7/1997 | Pang et al. |
| 5,658,892 A | 8/1997 | Flotte et al. |
| 5,842,787 A | 12/1998 | Kopf-Sill et al. |
| 5,951,976 A | 9/1999 | Segal |
| 6,133,503 A | 10/2000 | Scheffler |
| 6,156,181 A | 12/2000 | Parce et al. |
| 6,186,660 B1 | 2/2001 | Kopf-Sill et al. |
| 6,218,166 B1 | 4/2001 | Ravindranath et al. |
| 6,410,329 B1 | 6/2002 | Hansen et al. |
| 6,461,867 B1 | 10/2002 | Cai et al. |
| 6,562,616 B1 | 5/2003 | Toner et al. |
| 7,109,034 B2 | 9/2006 | Ormar et al. |
| 7,704,743 B2 | 4/2010 | Fedorov et al. |
| 7,993,821 B2 | 8/2011 | Chiu et al. |
| 8,211,656 B2 | 7/2012 | Hyde et al. |
| 8,669,044 B2 | 3/2014 | Chiu et al. |
| 8,697,359 B1 | 4/2014 | Zhang |
| 8,844,570 B2 | 9/2014 | Glick et al. |
| 9,005,579 B2 | 4/2015 | Nowinski et al. |
| 9,017,991 B2 | 4/2015 | Diefenbach |
| 9,157,550 B2 | 10/2015 | Wheeler et al. |
| 9,255,245 B2 | 2/2016 | Bernick et al. |
| 9,364,504 B2 | 6/2016 | Godfrin et al. |
| 9,950,049 B2 | 4/2018 | Godfrin et al. |
| 10,124,336 B2 | 11/2018 | Sharei et al. |
| 10,526,573 B2 | 1/2020 | Ding et al. |
| 10,696,944 B2 | 6/2020 | Sharei et al. |
| 10,870,112 B2 | 12/2020 | Sharei et al. |
| 2003/0133922 A1 | 7/2003 | Kasha, Jr. |
| 2004/0176282 A1 | 9/2004 | Dalby et al. |
| 2004/0197898 A1 | 10/2004 | Nakatani et al. |
| 2005/0026283 A1 | 2/2005 | Ormar et al. |
| 2006/0134067 A1 | 6/2006 | Liu et al. |
| 2006/0134772 A1 | 6/2006 | Miles et al. |
| 2006/0223185 A1 | 10/2006 | Fedorov et al. |
| 2007/0243523 A1 | 10/2007 | Ionescu-Zanetti et al. |
| 2007/0249038 A1 | 10/2007 | Adamo et al. |
| 2008/0026465 A1 | 1/2008 | Nakata |
| 2008/0311140 A1 | 12/2008 | Lee et al. |
| 2008/0318324 A1 | 12/2008 | Chiu et al. |
| 2009/0209039 A1 | 9/2009 | Adamo et al. |
| 2009/0280518 A1 | 11/2009 | Adamo et al. |
| 2010/0203068 A1 | 8/2010 | Betz et al. |
| 2010/0249621 A1 | 9/2010 | Ichitani |
| 2010/0323388 A1 | 12/2010 | Chiu et al. |
| 2011/0014616 A1 | 1/2011 | Holmes et al. |
| 2011/0030808 A1 | 2/2011 | Chiou et al. |
| 2011/0091973 A1 | 4/2011 | Glaser |
| 2011/0300205 A1 | 12/2011 | Geall et al. |
| 2012/0064505 A1 | 3/2012 | Suresh et al. |
| 2012/0107925 A1 | 5/2012 | Li et al. |
| 2012/0207745 A1 | 8/2012 | Godfrin et al. |
| 2012/0222143 A1 | 8/2012 | Fahrenkrug et al. |
| 2013/0023051 A1 | 1/2013 | Bundock et al. |
| 2013/0045211 A1 | 2/2013 | Nowinski et al. |
| 2013/0065314 A1 | 3/2013 | Macmillan |
| 2014/0011226 A1 | 1/2014 | Bernick et al. |
| 2014/0273229 A1 | 9/2014 | Meacham et al. |
| 2014/0287509 A1 | 9/2014 | Sharei et al. |
| 2015/0184127 A1 | 7/2015 | White et al. |
| 2015/0196913 A1 | 7/2015 | Liu et al. |
| 2016/0017340 A1 | 1/2016 | Wu et al. |
| 2016/0193605 A1 | 7/2016 | Sharei et al. |
| 2016/0199837 A1 | 7/2016 | Breinlinger et al. |
| 2017/0020926 A1 | 1/2017 | Mata-Fink et al. |
| 2017/0326213 A1 | 11/2017 | Jajosky et al. |
| 2018/0003696 A1 | 1/2018 | Sharei et al. |
| 2018/0016539 A1 | 1/2018 | Ding et al. |
| 2018/0085402 A1 | 3/2018 | Kahvejian et al. |
| 2018/0201889 A1 | 7/2018 | Sharei et al. |
| 2018/0245089 A1 | 8/2018 | Sharei et al. |
| 2019/0017072 A1 | 1/2019 | Ditommaso et al. |
| 2019/0030536 A1 | 1/2019 | Sharei et al. |
| 2019/0093073 A1 | 3/2019 | Sharei et al. |
| 2019/0111082 A1 | 4/2019 | Gilbert et al. |
| 2019/0382796 A1 | 12/2019 | Gilbert et al. |
| 2020/0277566 A1 | 9/2020 | Sharei et al. |

FOREIGN PATENT DOCUMENTS

| | | |
|---|---|---|
| CN | 106244543 A | 12/2016 |
| EP | 882448 A1 | 12/1998 |
| EP | 1225228 A2 | 7/2002 |
| EP | 2169070 A1 | 3/2010 |
| JP | H01196566 A | 8/1989 |
| JP | H03257366 A | 11/1991 |
| JP | 2010-02582 A | 2/2010 |
| JP | 2010-025852 A | 2/2010 |
| JP | 2011-163830 A | 8/2011 |
| JP | 2013-536848 A | 9/2013 |
| JP | 6235085 B2 | 11/2017 |
| KR | 2014-0115560 A | 10/2014 |
| WO | WO 85/00748 A1 | 2/1985 |
| WO | WO 97/20570 A1 | 6/1997 |
| WO | WO 00/07630 A1 | 2/2000 |
| WO | WO 02/067863 A2 | 9/2002 |
| WO | WO 03/020039 A1 | 3/2003 |
| WO | WO 2004/001424 A1 | 12/2003 |
| WO | WO 2006/010521 A1 | 2/2006 |
| WO | WO 2006/095330 A2 | 9/2006 |
| WO | WO 2006/105251 A2 | 10/2006 |
| WO | WO 2007/067032 A1 | 6/2007 |
| WO | WO 2007/097934 A2 | 8/2007 |
| WO | WO 2008/021465 A2 | 2/2008 |
| WO | WO 2008/0214565 A2 | 2/2008 |
| WO | WO 2009/056332 A1 | 5/2009 |
| WO | WO 2010/016800 A1 | 2/2010 |
| WO | WO 2010/077290 A1 | 7/2010 |
| WO | WO 2010/105135 A1 | 9/2010 |
| WO | WO 2010/129671 A2 | 11/2010 |

(56) References Cited

FOREIGN PATENT DOCUMENTS

| | | |
|---|---|---|
| WO | WO 2010/145849 A2 | 12/2010 |
| WO | WO 2011/051346 A1 | 5/2011 |
| WO | WO 2011/119492 A2 | 9/2011 |
| WO | WO 2012/069568 A2 | 5/2012 |
| WO | WO 2012/097450 A1 | 7/2012 |
| WO | WO 2012/106536 A2 | 8/2012 |
| WO | WO 2012/118799 A2 | 9/2012 |
| WO | WO 2012/162779 A1 | 12/2012 |
| WO | WO 2013/059343 A1 | 4/2013 |
| WO | WO 2013/185032 A1 | 12/2013 |
| WO | WO 2014/065596 A1 | 5/2014 |
| WO | WO 2014/106629 A1 | 7/2014 |
| WO | WO 2014/106631 A1 | 7/2014 |
| WO | WO 2014/120956 A1 | 8/2014 |
| WO | WO 2014/165707 A2 | 10/2014 |
| WO | WO 2015/023982 A1 | 2/2015 |
| WO | WO 2015/061458 A1 | 4/2015 |
| WO | WO 2015/153102 A1 | 10/2015 |
| WO | WO 2015/161276 A2 | 10/2015 |
| WO | WO 2016/003485 A1 | 1/2016 |
| WO | WO 2016/070136 A1 | 5/2016 |
| WO | WO 2016/077761 A1 | 5/2016 |
| WO | WO 2016/109864 A1 | 7/2016 |
| WO | WO 2016/115179 A1 | 7/2016 |
| WO | WO 2016/183482 A1 | 11/2016 |
| WO | WO 2017/005700 A1 | 1/2017 |
| WO | WO 2017/008063 A1 | 1/2017 |
| WO | WO 2017/041050 A1 | 3/2017 |
| WO | WO 2017/041051 A1 | 3/2017 |
| WO | WO 2017/106899 A2 | 6/2017 |
| WO | WO 2017/123644 A1 | 7/2017 |
| WO | WO 2017/123646 A1 | 7/2017 |
| WO | WO 2017/123663 A1 | 7/2017 |
| WO | WO 2017/192785 A1 | 11/2017 |
| WO | WO 2017/192786 A1 | 11/2017 |
| WO | WO 2018/089497 A1 | 5/2018 |

OTHER PUBLICATIONS

Sharei et al. A vector-free microfluidic platform for intracellular delivery. PNAS (Jan. 2013), early edition, 6 pages plus 10 page supplement. (Year: 2013).*

Maratou et al. Glucose transporter expression on the plasma membrane of resting and activated white blood cells. European Journal of Clinical Investigation (2007), v37, p. 282-290. (Year: 2007).*

Adamo, Andrea et al., "Microfluidics-Based Assessment of Cell Deformability," Analytical Chemistry (Aug. 7, 2012), vol. 84, No. 15, pp. 6438-6443.

ATCC Thawing, Propagating, and Cryopreserving Protocol, NCI-PBCF-HTB81 (DU 145), Prostate Carcinoma (ATCC® htb-81), Version 1.6, 2012, 23 pages.

Augustsson et al. "Microfluidic, Label-Free Enrichment of Prostate Cancer Cells in Blood Based on Acoustophoresis," Analytical Chemistry, Aug. 28, 2012 (Aug. 28, 2012), vol. 84, No. 18, pp. 7954-7962.

BD Bioscience FITC-labeled anti-CD45 antibody, 2 pages.

BD Bioscience PE-labeled anti-EpCAM antibody, 2 pages.

Boohaker, et al., "The Use of Therapeutic Peptides to Target and to Kill Cancer Cells," Curr. Med. Chem., 19(22), 26 pages, 2012.

Cancer Facts & Figures 2012. Published by the American Cancer Society in Atlanta, 68 pages.

Certificate of Grant dated Jan. 11, 2018 for Chinese Application No. 201280060689.6.

Cross et al., "Nanomechanical analysis of cells from cancer patients," Nature Nanotechnology (Dec. 2007), vol. 2, pp. 780-783.

Downs, C. A. et al. (May 14, 2011). "Cell Culture Models Using Rat Primary Alveolar type 1 Cells", Pulmonary Pharm. & Therapeutics 24(5)577-586.

Eixarch, H. et al. "Tolerance induction in experimental autoimmune encephalomyelitis using non-myeloablative hematopoietic gene therapy with autoantigen." Molecular Therapy 17.5 (2009): 897-905.

Esposito et al., "Intraerythrocytic administration of a synthetic Plasmodium antigen elicits antibody response in mice, without carrier molecules or adjuvants," International Journal of Parasitology, vol. 20, No. 8, pp. 1109-1111 (1990).

European Search Opinion dated Apr. 30, 2015 from European Application No. 12 841 329, 2 pages.

Examination Report No. 1 dated Dec. 1, 2016 from Australian Application No. 2012326203, 10 pages.

Examination Report No. 2 dated Jul. 26, 2017 from Australian Application No. 2012326203, 6 pages.

Extended European Search Report for EP 14836593.5, dated Feb. 23, 2017, 9 pages.

Gasteiger, et al., "Protein Identification and Analysis Tools on the ExPASy Server," The Proteomics Handbook, Chapter 52, pp. 571-607, 2005.

Griesbeck et al., "Sex Differences in Plasmacytoid Dendritic Cell Levels of IRF5 Drive higher IFN-alpha production in Women," The Journal of Immunology (Dec. 2015), vol. 195(11):5327-5336.

Hallow et al., "Shear-Induced Intracellular Loading of Cells With Molecules by Controlled Microfluidics," Biotechnology and Bioengineering (2008), vol. 99(4):846-854.

Han, X. et al., "CRISPR-Cas9 delivery to hard-to-transfect cells via membrane deformation," Sci. Adv., Aug. 14, 2015, e1500454, 8 pages.

Hillerdal et al., "Systemic treatment with CAR-engineered T cells against PSCA delays subcutaneous tumor growth and prolongs survival of mice," BMC Cancer (Jan. 18, 2014), vol. 14, No. 30, pp. 1-9.

Hoeppener et al., "Immunomagnetic Separation Technologies," In: Ignatiadis M., Soritiou C., Pantel K. (eds.), Minimal Residual Disease and Circulating Tumor Cells in Breast Cancer. Recent Results in Cancer Research, vol. 195, pp. 43-58 (2012).

Hoskin, et al., "Studies on anticancer activitied of antimicrobial peptides," Biochimica et Biophysica Acta, v.1778, pp. 357-375, 2008.

Hosokawa, et al., "Size-Selective Microacvity Array for Rapid and Efficient Detection of Circulation Tumor Cells," Anal. Chem, 85:6629-6635, 2010.

Howarth, M. et al. (May 2008). "Monovalent, Reduced-Size Quantum Dots for Imaging Receptors on Living Cells," Nature Methods 5(5):397-399.

International Preliminary Report on Patentability dated Feb. 16, 2016 from International Application No. PCT/US2014/051343.

International Preliminary Report on Patentability, PCT/US2012/060646, dated Apr. 22, 2014, 7 pages.

International Preliminary Report on Pattentability, PCT/US2015/058489, dated May 2, 2017, 12 pages.

International Preliminary Report on Pattentability, PCT/US2015/060689, dated May 16, 2017, 10 pages.

International Search Report and Written Opinion dated Jan. 3, 2017 from International Application No. PCT/US2016/050287, 13 pages.

International Search Report and Written Opinion dated Jan. 12, 2016 from International Application No. PCT/US2016/050288, 11 pages.

International Search Report and Written Opinion dated Feb. 1, 2016 from International Application No. PCT/US15/60689.

International Search Report and Written Opinion dated Feb. 25, 2013 from International Application No. PCT/US12/060646.

International Search Report and Written Opinion dated Mar. 11, 2016 from International Application No. PCT/US15/584489.

International Search Report and Written Opinion dated Mar. 21, 2016 from International Application No. PCT/US2016/013113.

International Search Report and Written Opinion dated Dec. 18, 2014 from International Application No. PCT/US2014/051343.

International Search Report and Written Opinion dated Jul. 21, 2017 from International Application No. PCT/US2017/030933, 20 pages.

International Search Report and Written Opinion dated Sep. 19, 2017 from International Application No. PCT/US2017/030932, 18 pages.

Janeway CA Jr, et al., "The structure of a typical antibody molecule," Immunobiology: The Immune System in Heath and Disease, 5th edition (2001), 5 pages.

(56) References Cited

OTHER PUBLICATIONS

Kim, D., et al., "Microengineered Platforms for Cell Mechanobiology," Annual Review of Biomedical Engineering, 2009, vol. 11, pp. 203-233.
Lee et al., "Nonendocytic delivery of functional engineered nanoparticles into the cytoplasm of live cells using a novel, high-throughput microfluidic device," Nano Letters (2012), vol. 12, pp. 6322-6327.
Lin et al., "Highly selective biomechanical separation of cancer cells from leukocytes using microfluidic and hydrodynamic concentrator," Biomicrofluidics (Jun. 26, 2013), vol. 7, No. 3, pp. 34114-1-34114-11.
Liu et al., "Molecular imaging in tracking tumor-specific cytotoxic T lymphocytes (CTLs)," Theranostics (Jul. 28, 2014), vol. 4, No. 10, pp. 990-1001.
Liu et al., "Spatially selective reagent delivery into cancer cells using a two-layer microfluidic culture system," Analytica Chimica Acta (Sep. 1, 2012), vol. 743, pp. 125-130.
Liu, W. et al. (Jan. 20, 2010). "Compact Biocompatible Quantum Dots via RAFT-Mediated Synthesis of Imidazole-Based Random Copolymer Ligand," JACS 132(2):472-483.
Mattews, B.D., et al., "Cellular adaptation to mechanical stress: role of integrins, Rho, cytoskeletal tension and mechanosensitive ion channels," Journal of Cell Science, vol. 119, pp. 508-518, 2006.
Milo, R. "What is the total number of protein molecules per cell volume? A call to rethink some published values." Bioessays 35.12 (2013): 1050-1055.
Murphy, J. S. et al. (Sep. 1, 1956, e-pub May 2004). "Measurement of Wall Shearing Stress in the Boundary Layer by Means of an Evaporating Liquid Film," Journal of Applied Physics 27(9):1097-1103.
Notice of Grant dated Jan. 11, 2018 for Chinese Patent Application No. 201280060689.6.
Office Action dated Dec. 1, 2016 from Chinese Application No. 201280060689.6, 4 pages.
Office Action dated Dec. 17, 2014 from Chinese Office Action No. 201280060689.6, 9 pages.
Office Action dated Jul. 7, 2016 from Japanese Application No. 2014-537184, 7 pages.
Office Action dated Jun. 14, 2016 from European Application No. 12 841 329, 4 pages.
Office Action dated Jun. 23, 2017 from Chinese Application No. 201280060689.6, 4 pages.
Office Action dated May 13, 2016 from Chinese Application No. 201280060689.6, 4 pages.
Office Action dated Oct. 11, 2017 from European Application No. 12 841 329, 4 pages.
Office Action dated Sep. 6, 2015 from Chinese Office Action No. 201280060689.6, 8 pages.
Office Action dated Aug. 15, 2017 from U.S. Appl. No. 14/912,001, 32 pages.
Office Action dated Feb. 24, 2017 from U.S. Appl. No. 14/352,354, 11 pages.
Office Action dated Jul. 27, 2016 from U.S. Appl. No. 14/352,354, 9 pages.
Office Action dated Jul. 5, 2017 from Chinese Application No. 201480056295.2, 13 pages.
Office Action dated Jul. 7, 2016 from Japanese Application No. 2014-537184, 14 pages.
Office Action dated Mar. 16, 2017 from U.S. Appl. No. 14/912,001, 29 pages.
Office Action dated Mar. 23, 2017 from Russian Application No. 2014119926/10(031699), 10 pages.
Office Action dated May 1, 2017 from Japanese Application No. 2014-537184, 13 pages.
Office Action dated Oct. 26, 2016 from Russian Application No. 2014119926/10(031699), 10 pages.
Polvani et al., "Murine Red Blood Cells as Efficient Carriers of Three Bacterial Antigens for the Production of Specific and Neutralizing Antibodies," Biotechnology and Applied Biochemistry, vol. 14, pp. 347-356 (1991).

Ravilla et al., "Erythrocytes as Carrier for Drugs, Enzymes and Peptides," Journal of Applied Pharmaceutical Science, vol. 2, No. 2, pp. 166-176 (2012).
Rutella et al., "Tolerogenic dendritic cells: cytokine modulation comes of age," Blood, vol. 108, No. 5, pp. 1435-1440 (2006).
Sharei et al, "Ex vivo Cytosolic Delivery of Functional Macromolecules to Immune Cells," (Apr. 13, 2015), PLoS One, vol. 10, No. 4, 12 pp. e0118803.
Sharei et al., "A vector-free microfluidic platform for intracellular delivery," Proc. Natl. Acad. Sci. USA (Feb. 5, 2013), vol. 110, No. 6, pp. 2082-2087.
Sharei et al., "Cell Squeezing as a Robust, Microfluidic Intracellular Delivery Platform," Journal of Visualized Experiments (Nov. 7, 2013), No. 81, 9 pages.
Sharei et al., "Microfluidic Cell Deformation as a Robust, Vector-Free Method for Cystosolic Delivery of Macromolecules 2012 Annual Meeting," (Jan. 1, 2012), 3 pages.
Sharei et al., "Plasma membrane recovery kinetics of a microfluidic intracellular delivery platform," Integrative Biology (2014), vol. 6, pp. 470-475.
Shelby et al., "A microfluidic model for single-cell capillary obstruction by Plasmodium falciparum infected erythrocytes," (Dec. 9, 2003), Proc. Nat. Acad. Sci., vol. 100, No. 25, pp. 14618-14622.
Steinman et al., "Tolerogenic dendritic cells," Annual Review of Immunology, vol. 21, pp. 685-711 (2003).
Stewart et al., "In vitro and ex vivo strategies for intracellular delivery," Nature, vol. 538, No. 7624, pp. 183-192 (2016).
Supplementary European Search Report dated Apr. 30, 2015 from European Application No. 12 841 329, 3 pp.
Swaminathan, et al., "Mechanical Stiffness Grades Metastatic Potential in Patient Tumor Cells and in Cancer Cell Lines," Cancer Research, 71(15):5075-5080, 2011.
Szeto et al., "Microfluidic squeezing for intracellular antigen loading in polyclonal B-cells as cellular vaccines," Scientific Reports, vol. 5, 10276 (May 2015), 13 pages.
Third-Party Submission mailed Oct. 23, 2015 from U.S. Appl. No. 14/352,354, 21 pages.
Williams, A.R. et al. (Nov. 5, 1999). "Filtroporation: A Simple, Reliable Technique for Transfection and Macromolecular Loading of Cells", Biotechnology and Bioengineering 65(3)341-346.
Zarnitsyn et al., "Electrosonic ejector microarray for drug and gene delivery," Biomed Microdevices (2008) 10:299-308.
Extended European Search Report for EP App. No. 16822078.8 dated Jan. 30, 2019.
International Search Report and Written Opinion for PCT/US2016/041653 dated Oct. 4, 2016.
International Preliminary Report on Patentability for PCT/US2016/041653 dated Jan. 18, 2018 (Chapter I).
Extended European Search Report for EP App. No. 16737769.6 dated May 3, 2018.
International Preliminary Report on Patentability for PCT/US2016/013113 dated Jul. 27, 2017 (Chapter I).
Partial Supplementary European Search Report for EP App. No. 15859824.3 dated Jun. 11, 2018.
Partial Supplementary European Search Report for EP App. No. 15855640.7 dated May 30, 2018.
Banz, A. et al., "Tumor Growth Control Using Red Blood Cells as the Antigen Delivery System and Poly(I:C)," J Immunother 2012, 35(5), pp. 409-417.
Chaw et al. Multi-step microfluidic device for studying cancer metastasis. Lab on a Chip (2007), v7, p. 1041-1047.
Cremel, L. et al., "Innovative approach in Pompe disease therapy: Induction of immune tolerance by antigen-encapsulated red blood cells," Int J Pharm. Aug. 1, 2015;491(1-2), pp. 69-77.
Cremel, L. et al., "Red blood cells as innovative antigen carrier to induce specific immune tolerance," Int J Pharm. Feb. 25, 2013;443(1-2), pp. 39-49.
Ding, X. et al., "High-throughput nuclear delivery and rapid expression of DNA via mechanical and electrical cell-membrane disruption," Nature Biomedical Engineering (2017), vol. 1, No. 3, 7 pages.

(56) References Cited

OTHER PUBLICATIONS

Favretto, M. E. et al., "Human erythrocytes as drug carriers: Loading efficiency and side effects of hypotonic dialysis, chlorpromazine treatment and fusion with liposomes," Journal of Controlled Release 2013; 170: 343-351.
Grimm, A. J. et al., "Memory of tolerance and induction of regulatory T cells by erythrocyte-targeted antigens," Sci Rep. Oct. 29, 2015;5:15907, 11 pages.
Kiani et al., Cas9 gRNA engineering for genome editing, activation and repression. Nature Methods. 2015;12:1051-4.
Li, J. et al., "Microfluidic-Enabled Intracellular Delivery of Membrane Impermeable Inhibitors to Study Target Engagement in Human Primary Cells," ACS Chemical Biology 2017, vol. 12, No. 12, pp. 2970-2974.
Lorentz, K. M. et al., "Engineered binding to erythrocytes induces immunological tolerance to E. coli asparaginase," Sci Adv. Jul. 17, 2015;1(6):e1500112, 11 pages.
Mali, P. et al., "RNA-guided human Genome Engineering via Cas9," Science (2013), vol. 339, No. 6121, pp. 823-826.
Rossi, L. et al., "Erythrocyte-mediated delivery of phenylalanine ammonia lyase for the treatment of phenylketonuria in BTBR-Pah.sup.enu2 mice," Journal of Controlled Release 194; 37-44 (2014).
Stevenson, D. J. et al., "Single cell optical transfection," IEEE Transactions on Ultrasonics, Ferroelectrics and Frequency Control, vol. 53, No. 1, 863-871 (2010).
Tlaxca, J. L. et al., "Analysis of in vitro Transfection by Sonoporation Using Cationic and Neutral Microbubbles," Ultrasound in Medicine and Biology, vol. 36, No. 11, 1907-1918 (2010).
Wright et al., Rational design of a split-Cas9 enzyme complex. PNAS. Mar. 2015;112(10):2984-9.
Yin et al., "Delivery technologies for genome editing," Nature Reviews (2017), vol. 16, No. 6, pp. 387-399.
Zdobnova et al., Self-Assembling Complexes of Quantum Dots and scFv Antibodies for Cancer Cell Targeting and Imaging. PLoS One. 2012;7(10):e48248. 8 pages.
Extended European Search Report for EP App. No. 15859824.3 dated Sep. 11, 2018.
Extended European Search Report for EP App. No. 15855640.7 dated Sep. 5, 2018.
Extended European Search Report dated Nov. 21, 2019 for Application No. EP 19187758.8.
Fagerlund et al., The Cpf1 CRISPR-Cas protein expands genome-editing tools. Genome Biol. Nov. 17, 2015;16:251. doi: 10.1186/s13059-015-0824-9.
Gilbert, T-cell-inducing vaccines—what's the future. Immunology. Jan. 2012;135(1):19-26. doi: 10.1111/j.1365-2567.2011.03517.x.
Jiang, The immunopotentiators and delivery systems for use in vaccines. Prog Microbiol Immunol. Dec. 31, 2012;(3):1-8.
Sharei et al., "A vector-free microfluidic platform for intracellular delivery," Proc. Natl. Acad. Sci. USA (Feb. 5, 2013), vol. 110, No. 6, Supporting Information. 10 pages.
Vechkanov et al., Osnovy kletochnoy inzhenerii: Study guide. Rostov-on-Don. 2012; 133 pages. Relevant pp. 15-16.
Yangulov et al., Vliyaniye razlichnykh kriozashchitnykh sred na zhiznesposobnost kriokonservirovannykh limfoblastnykh kletochnyk liniy H-9 I U-937. Problemy kriobiologii. 1991;3:46-9.

Zhdanov et al., Tayna tretiego tsarstva. Znaniye. 1975; 200 pages. Relevant pp. 124-125.
U.S. Appl. No. 17/075,116, filed Oct. 20, 2020, Sharei et al.
Alberts et al., Chapter 11: Ion Channels and the Electrical Properties of Membranes. Molecular Biology of the Cell, $4^{th}$ Ed. New York: Garland Science. 2002. 20 pages.
Azarikia et al., Stabilization of biopolymer microgels formed by electrostatic complexation: Influence of enzyme (laccase) cross-linking on pH, thermal, and mechanical stability. Food Res Int. Dec. 2015;78:18-26. doi: 10.1016/j.foodres.2015.11.013. Epub Nov. 21, 2015.
Chen et al., Patch clamping on plane glass-fabrication of hourglass aperture and high-yield ion channel recording. Lab Chip. Aug. 21, 2009;9(16):2370-80. Epub May 14, 2009. https://doi.org/10.1039/b901025d.
Ditommaso et al., Cell engineering with microfluidic squeezing preserves functionality of primary immune cells in vivo. PNAS. Oct. 2018;115(46):E10907-14.
Escoffre et al., What is (still not) known of the mechanism by which electroporation mediates gene transfer and expression in cells and tissues. Mol Biotechnol. Mar. 2009;41(3):286-95. doi: 10.1007/s12033-008-9121-0. Epub Nov. 18, 2008.
Golzio et al., Direct visualization at the single-cell level of electrically mediated gene delivery. Proc Natl Acad Sci U S A. Feb. 5, 2002;99(3): 1292-7. doi: 10.1073/pnas.022646499. Epub Jan. 29, 2002.
Gossett et al., Hydrodynamic stretching of single cells for large population mechanical phenotyping. PNAS. May 2012;109(20):7630-5.
Nic an tsaoir et al., Scalable Antibody Production from CHO Cell Line of Choice Using Flow Electroporation. MaxCyte. Jun. 2016. 1 page.
Novokhatskiy et al., Problema kontaminatsii kletkami I novyie podkhody k kontroliu perevivaiemykh liniy. Voprosy virusologii. 1977;4:396-408.
Ogurtsov et al., Biotechnology. Principles and Application Training Manual. Ministry of Education and Science. 2012. 344 pages.
Paganin-Gioanni et al., Direct visualization at the single-cell level of siRNA electrotransfer into cancer cells. Proc Natl Acad Sci U S A. Jun. 28, 2011; 108(26):10443-7. doi: 10.1073/pnas.1103519108. Epub Jun. 13, 2011.
Song et al., Scientific basis for the use of hypotonic solutions with ultrasonic liposuction. Aesthetic Plast Surg. Mar.-Apr. 2006;30(2):233-8. doi: 10.1007/s00266-005-0087-z.
Stevenson, D. J. et al., "Single cell optical transfection," J. R. Soc. Interface, vol. 7, 863-871 (2010).
Weaver et al., A brief overview of electroporation pulse strength-duration space: A region where additional intracellular effects are expected. Bioelectrochemistry. Oct. 2012;87:236-43.
Wen et al., Shear Effects on Stability of DNA Complexes in the Presence of Serum. Biomacromolecules Oct. 9, 2017;18(10):3252-3259. doi: 10.1021/acs.biomac.7b00900. Epub Sep. 1, 2017.
Ye, Complexation between milk proteins and polysaccharides via electrostatic interaction: principles and applications—a review. Int J Food Sci Technol. Jan. 31, 2008;43(3):406-15.

* cited by examiner

SEQUENCE LISTING

```
<160> NUMBER OF SEQ ID NOS: 11

<210> SEQ ID NO 1
<211> LENGTH: 21
<212> TYPE: DNA
<213> ORGANISM: Artificial Sequence
<220> FEATURE:
<223> OTHER INFORMATION: Human CD45 siRNA Sense

<400> SEQUENCE: 1
cuggcugaau uucagagcat t                                              21

<210> SEQ ID NO 2
<211> LENGTH: 21
<212> TYPE: DNA
<213> ORGANISM: Artificial Sequence
<220> FEATURE:
<223> OTHER INFORMATION: Human CD4 siRNA Sense

<400> SEQUENCE: 2
gaucaagaga cuccucagut t                                              21

<210> SEQ ID NO 3
<211> LENGTH: 21
<212> TYPE: DNA
<213> ORGANISM: Artificial Sequence
<220> FEATURE:
```

<223> OTHER INFORMATION: vif siRNA Sense

<400> SEQUENCE: 3
cagauggcag gugaugauug t            21

<210> SEQ ID NO 4
<211> LENGTH: 21
<212> TYPE: RNA
<213> ORGANISM: Artificial Sequence
<220> FEATURE:
<223> OTHER INFORMATION: gag siRNA Sense

<400> SEQUENCE: 4
gauuguacug agagacaggc u            21

<210> SEQ ID NO 5
<211> LENGTH: 21
<212> TYPE: RNA
<213> ORGANISM: Artificial Sequence
<220> FEATURE:
<223> OTHER INFORMATION: control scrambled siRNA

<400> SEQUENCE: 5
gccaagcacc gaaguaaauu u            21

<210> SEQ ID NO 6
<211> LENGTH: 21
<212> TYPE: RNA
<213> ORGANISM: Artificial Sequence
<220> FEATURE:
<223> OTHER INFORMATION: Human DC-SIGN siRNA Sense

<400> SEQUENCE: 6
ggaacuggca cgacuccauu u            21

<210> SEQ ID NO 7
<211> LENGTH: 19
<212> TYPE: RNA
<213> ORGANISM: Artificial Sequence
<220> FEATURE:
<223> OTHER INFORMATION: CD4 siRNA

<400> SEQUENCE: 7
gaucaagaga cuccucagu            19

<210> SEQ ID NO 8
<211> LENGTH: 19
<212> TYPE: DNA
<213> ORGANISM: Artificial Sequence
<220> FEATURE:
<223> OTHER INFORMATION: Gapdh forward

<400> SEQUENCE: 8
agccacatcg ctcagacac            19

<210> SEQ ID NO 9
<211> LENGTH: 19
<212> TYPE: DNA
<213> ORGANISM: Artificial Sequence
<220> FEATURE:
<223> OTHER INFORMATION: Gapdh reverse

<400> SEQUENCE: 9
gcccaatacg accaaatcc            19

```
<210> SEQ ID NO 10
<211> LENGTH: 20
<212> TYPE: DNA
<213> ORGANISM: Artificial Sequence
<220> FEATURE:
<223> OTHER INFORMATION: CD4 forward

<400> SEQUENCE: 10
ggcagtgtct gctgagtgac                                               20

<210> SEQ ID NO 11
<211> LENGTH: 19
<212> TYPE: DNA
<213> ORGANISM: Artificial Sequence
<220> FEATURE:
<223> OTHER INFORMATION: CD4 reverse

<400> SEQUENCE: 11
gaccatgtgg gcagaacct                                                19
```

DELIVERY OF BIOMOLECULES TO IMMUNE CELLS

RELATED APPLICATIONS

This application claims the benefit of priority to PCT Application No. PCT/US2015/058489, filed Oct. 30, 2015, which claims the benefit of priority under 35 U.S.C. § 119(e) to U.S. Provisional Application No. 62/073,548, filed Oct. 31, 2014, each of which are incorporated herein by reference in their entireties.

GOVERNMENT SUPPORT

This invention was made with Government support under Grant Nos. GM101420, AI112521, AI111595, and AI069259 awarded by the National Institutes of Health. The Government has certain rights in the invention.

FIELD OF THE INVENTION

The invention relates to the delivery of materials to cells.

REFERENCE TO THE SEQUENCE LISTING

This application incorporates-by-reference nucleotide and/or amino acid sequences which are present in the file named "38172-508001WO_Sequence_Listing.txt," which is 2.31 kilobytes in size, and which was created Oct. 30, 2015 in the IBM-PC machine format, having an operating system compatibility with MS-Windows, which is contained in the text file filed Oct. 30, 2015 as part of this application.

BACKGROUND OF THE INVENTION

Delivery of macromolecules, such as polysaccharides, proteins, or nucleic acids, to the cell cytoplasm can transiently or permanently alter cell function for research or therapeutic purposes. However, existing techniques for intracellular delivery to primary immune cells, especially resting lymphocytes, have limitations. Electroporation results in considerable cellular toxicity. Viral vectors are unable to infect resting lymphocytes. Cell membrane penetrating (or transduction) peptides do not efficiently transfect primary lymphocytes. Antibody-drug complexes and conjugates require specific antibodies for each cell type and distinct designs to carry different payloads. Furthermore, they are expensive to produce and potentially immunogenic. Aptamer-siRNA chimeric RNAs have been shown to cause targeted gene knockdown in vivo, without any toxicity or immune activation, but have only been used to deliver small RNAs and they require identifying specific targeting aptamers for each cell of interest. Advances in nanoparticle and liposome based technologies have resulted in improved intracellular delivery of drugs and antigens to phagocytic antigen presenting cells, such as dendritic cells and monocyte/macrophages, but are ineffective for lymphocytes. Most of these methods lead to endosomal uptake of the payload, and only a very small proportion of the payload (estimated as ~1-2%) escapes from the endosome to the cytosol, where it needs to traffic for biological activity. Many of these techniques also result in accumulation of nonbiodegradable packaging or delivery material in the cell, which may affect cell function. Thus there is a need for alternative techniques capable of efficient and nontoxic delivery of a variety of macromolecules to immune cells.

SUMMARY OF THE INVENTION

The invention provides a solution to previous problems associated with delivery of compounds or compositions to immune cells. Prior to the invention, introduction of compounds, e.g., proteins, nucleic acids, carbohydrates, was difficult and occurred inefficiently and/or required the presence of undesirable mediators such as toxic compounds or viral vectors. According to the invention, a method for engineering of immune cell function comprises intracellular delivery of compounds by transiently disrupting a membrane surrounding the cytoplasm of the immune cell. For example, a viral vector-free method for preferentially delivering a compound to the cytosol of an immune cell includes a step of passing a cell suspension comprising the target immune cell through a microfluidic device and contacting the suspension with the compound(s) or payload to be delivered. The device comprises a constriction length of 10-60 µm and a constriction width of 3-8 µm, e.g., 3-4 µm or 4 µm.

For example, the device comprises a constriction of a diameter of 2 µm-10 µm. In preferred embodiments relating to naïve T and B cells, the device comprises a constriction having a length of about 10, 15, 20, 25, 30, or 10-30 µm, a width of about 3, 3.5, 4, or 3-4 µm, a depth of about 15, 20, 25, or 15-25 µm, and/or an about 5, 6, 7, 8, 9, 10, 11, 12, 13, 14, 15, or 5-15 degree angle.

Following passage through the constriction, the amount of compound delivered to an immune cell is at least 10% greater (e.g., 20%, 50%, 2-fold, 5-fold, 10-fold, or greater) than that delivered to a non-immune cell or compared to the amount delivered to an immune cell in the absence of cell squeezing, e.g., by endocytosis alone. For example, the immune cell comprises a B cell, T cell, macrophage, or dendritic cell. For delivery of payload preferentially to immune cells, an exemplary device is characterized by one or more channels comprising a constriction length of 30 µm and a constriction width of 4 µm through which the cells pass.

A temperature of 0 to 45 degrees Celsius is used during cell treatment, e.g., 0-25° C. For example, treatment of naïve T cells, B cells and/or monocytes is carried out at temperature of 4-8° C., e.g., on ice. In another example, dendritic cells, activated T cells, and/or activated B cells are treated using the device at temperatures of 20-25° C., e.g., at typical ambient room temperature.

The payload contains any molecule or compound sought to be delivered to the cytoplasm of an immune cell. For example, the compound comprises an antigen, e.g., a disease-associated antigen such as a tumor antigen, viral antigen, bacterial antigen, or fungal antigen. The antigen may be purified or in a mixture of other components, e.g., the antigen is present in a cell lysate such as a tumor cell lysate or lysate of biopsied infected or disease-affected tissue from a subject, e.g., a subject suffering from an infectious disease. In some example, the antigen comprises a whole, full-length (or un-processed) protein antigen, e.g., a protein or peptide that exceeds a length of 7, 8, 9, or 10 amino acids. Other cargo molecules include nucleic acids such as siRNA, mRNA, miRNA, coding or non-coding oligonucleotides as well as small molecules, e.g., small molecule probes. Nucleic acids such as DNA, e.g., expression vectors such as plasmids, are also delivered in this manner without the need for a viral vector.

In some examples, the immune cell is in a resting state compared to an activated state. For example, cells are characterized by expression of the following markers:

CD25, KLRG1, CD80, CD86, PD-1, PDL-1, CTLA-4, CD28, CD3, CD62L, CCR7, CX3CR1 and CXCR5, each of which may be manipulated (increased or reduced by introducing molecules into the immune cells using the methods described). Cell suspensions include processed cells, e.g., resuspended buffy coat cells (fractionated white blood cells) or whole blood. Naïve immune cells, e.g., T cells, are characterized by comparatively low levels of expression of CD25, CD80, CD86, PD-1, and CTLA-4 and by comparatively high level of CCR7 (compared to activated cells).

The device for preferentially delivering a compound to an immune cell compared to a non-immune cell, comprises at least one microfluidic channel, e.g., in the form of a syringe, or a plurality of channels, e.g., in the form of a microchip or microfluidic device. For example, the channel comprises a constriction length of 30 μm and a constriction width of 4 μm.

The invention also includes a method for engineering of immune cell function by intracellular delivery of compounds, which delivery is mediated by transiently disrupting a membrane surrounding the cytoplasm of the immune cell and delivering into the cytosol an antigen. For example, the antigen comprises a length of greater than 2, 3, 4, 5, 6, 7, 8, 9, or 10 amino acids and wherein the immune cell processes the antigen into a peptide that is less than 11 amino acids in length. The cell then displays the shorter, processed peptide, a class I histocompatibility antigen restricted processed form of the antigen, on a surface of the immune cell. For example, peptides for MHC/HLA processed for class I presentation to CD8+ T cells or cytotoxic T cells are in the range of 8-10 residues, and peptides processed for MHC/HLA class II presentation to CD4+ T cells or helper cells are in the range of 14-20 residues. Peptides shorter than 8 residues (e.g., 2, 3, 4, 5, 6, or 7 residues) are useful for presentation to other T cell types or NK cells.

For example, the cell membrane is disrupted by passing the immune cell through a constriction of a diameter of 2 μm-10 μm. The antigen delivered by cell squeezing into the cytosol is a full-length, unprocessed protein or a peptide that must be processed to a size/length suitable for binding to a histocompatibility antigen for antigen presentation by the antigen presenting cell. The method of engineering immune cell function may further comprise contacting the antigen-loaded immune cell with an effector T cell and activating a cytotoxic T cell immune response. In some examples, squeezed antigen-loaded immune cell comprises a B cell, dendritic cell or macrophage. In other examples, the squeezed antigen-loaded immune cell comprises a T cell. In either case, the squeezed antigen loaded immune cell comprises at least 10%, 25%, 50%, 2-fold, 5-fold, 10-fold, 20-fold, 25-fold, 50-fold, or more antigen or other payload composition compared to an immune cell contacted with the same antigen or payload in the absence of squeezing, e.g., uptake by endocytosis or pinocytosis alone.

The function, activity, or activation state of the immune cell is altered following such treatment. For example, a method for conferring an antigen presenting phenotype on a T cell is carried out by delivering an antigen, e.g., a whole, unprocessed protein or fragment thereof, to the cytosol of a T cell by passing the T cell through a microfluidic device as described above. For example, the device comprises a constriction of a diameter of about 2 μm-10 μm and the T cell comprises a class I histocompatibility antigen-restricted, processed form of the antigen on a surface of the T cell following passage through the microfluidic device. The method may further comprise contacting the first (squeezed, antigen-loaded) T cell with a second T cell, the second T cell comprising a class I histocompatibility antigen restricted cytotoxic T cell phenotype. Exemplary antigens include one or more tumor antigens, e.g., a mixture of tumor antigens such as a tumor biopsy lysate, or a viral antigen. Production of antigen-loaded T cells in this manner are used in vitro and/or in vivo to elicit a cytotoxic T cell response. Thus, the use of cell-squeezed, antigen loaded T cell to activate a cytotoxic T cell response specific for the antigen is encompassed in the invention. For example, such T cells confer clinical benefit by killing tumor cells and/or killing virally-infected cells, depending upon the antigen delivered/loaded.

The compositions described herein are purified. Purified compounds are at least 60% by weight (dry weight) the compound of interest. Preferably, the preparation is at least 75%, more preferably at least 90%, and most preferably at least 99%, by weight the compound of interest. Purity is measured by any appropriate standard method, for example, by column chromatography, polyacrylamide gel electrophoresis, or HPLC analysis. For example, the compound, e.g., protein antigen, has been separated from one or more compounds with which is occurs in nature. In the case of cells, a purified population is at least 75%, 85%, 90%, 95%, 98%, 99% or 100% the cell type of choice. Methods or purifying or enriching for a particular cell type are well known, including segregating by size or cell surface marker expression using device such as cell sorting machines.

Other features and advantages of the invention will be apparent from the following description of the preferred embodiments thereof, and from the claims. All references cited herein are incorporated by reference.

BRIEF DESCRIPTION OF THE DRAWINGS

FIG. 2A shows representative histograms of T cells, B cells and myeloid cells (CD11 b+) treated by the CellSqueeze device to deliver APC-labeled IgG1.

In FIG. 3A, human T cells and MDDCs were tested for delivery of cascade blue labeled 3 kDa dextran, fluorescein labeled 70 kDa dextran, and APC labeled IgG1. The representative histograms for a 30-4 (T cells) and 10-7 (MDDCs) device (left) and replicates across device designs (right) are displayed. FIG. 3B shows SiRNA mediated knockdown of CD4 and DC-SIGN protein levels in CD4+ T cells and MDDCs respectively. Different siRNA concentrations and device designs were tested to assess knockdown dependence on dose or constriction size. FIG. 3C shows that human regulatory T cells also showed significant knockdown of CD4 expression in response to treatment by a 30-4 device. Dead cells were excluded for delivery or knockdown analysis. FIG. 3D shows a comparison of device performance in T cells to nucleofection by Amaxa. Protein expression 72 hrs after delivery of siRNA against CD4 is shown for the two systems. Cell viability after treatment by the two methods is also shown.

FIG. 24A: splenic DCs cultured in LPS (1 ug/ml) after treatment by squeezing, by antigen endocytosis alone, and untreated cells showed no detectable difference in their ability to upregulate CD80 and CD86 expression. Non stimulated endocytosis conditions and untreated cells maintained at 4° C. were used as controls. FIG. 24B: splenic DCs from a CD45 congenic mouse were injected into the footpad of C57BL6 mice with LPS (1 ug/ml) and recovered in the draining lymph node 18 hrs post injection. No significant difference in lymph node homing ability was detected.

FIG. 25A: in vivo proliferation of adoptively transferred CD8+OT-I T cells in response to subcutaneous DC vaccination. Device treated BMDCs (0.1 mg/ml of Ova) demonstrated a significant increase (P<0.0001) in T cell proliferation relative to those that were allowed to endocytose antigen. FIG. 25B: in vitro proliferation of CD8+OT-I T cells that have been cocultured with BMDCs treated with the cell lysate of an Ova expressing melanoma cell line (B16F10). The % indicates the fraction of cell lysate material that was added to a BMDC cell suspension prior to treatment by a 10-6 CellSqueeze device. The CD8 T cells were labeled by carboxyfluoroscein succinimidyl ester (CFSE) prior to contact with the APC. If they proliferate, the CFSE dye is distributed amongst daughter cells and results in lower fluorescence intensity per cell. Unproliferated T cells retain high CFSE intensity. FIG. 25C: measuring the fraction of antigen-specific IFNγ secreting CD8 T cells. In these experiments, mice were vaccinated against Ova in the absence of adoptively transferred OT-I T cells. The endogenous, antigen specific response was measured by isolating the spleens of vaccinated mice 7 days after vaccination and restimulating them in vitro with SIINFEKL peptide (an OVA epitope). Antigen-specific CD8 T cells secrete IFNγ in response to restimulation. FIG. 25D; in vitro proliferation of CD8+OT-I T cells that have been cocultured with B cells treated with two different device designs (0.1 mg/ml Ova). CpG was used as an adjuvant in these experiments.

DETAILED DESCRIPTION

Figure 1:
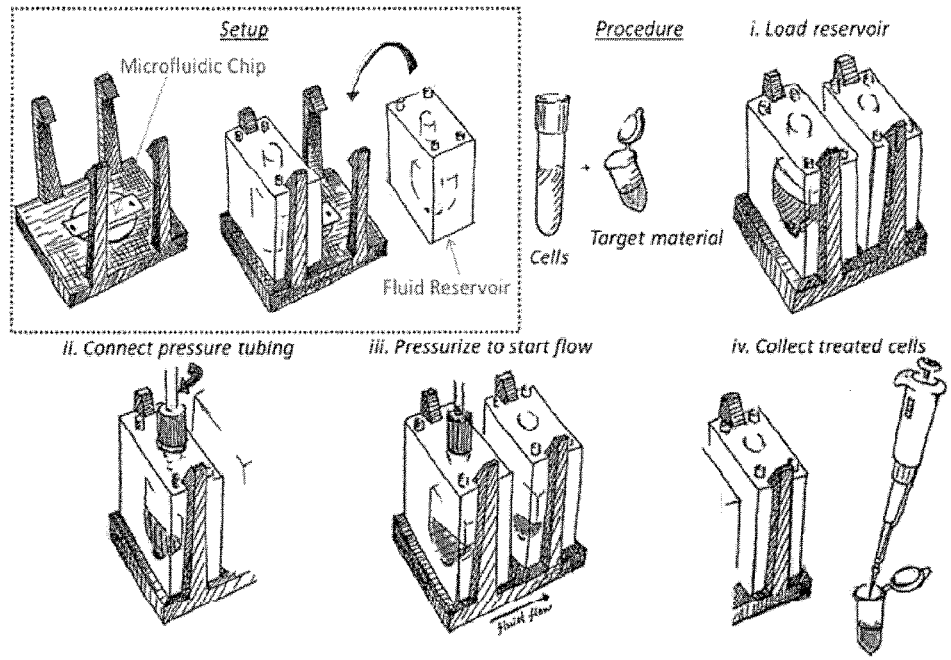
FIG. 1A is a series of diagrams showing a delivery system. To set up the system, each microfluidic chip is mounted into a holder that allows it to interface with polycarbonate fluid reservoirs. To operate the system, the macromolecules to be delivered are mixed with the cells, loaded into the device reservoir in a volume of about 30-15 μl and then connected to the pressure source to induce flow through the microfluidic channels.
FIG. 1B is a diagram showing cell deformation and payload delivery. As the cells flow through the channels, they deform at the constrictions, resulting in membrane disruption. Macromolecules in the fluid then diffuse through the disrupted membrane and remain trapped in the cell after its membrane is repaired. These figures demonstrate delivery by cell squeezing.
Figure 1:
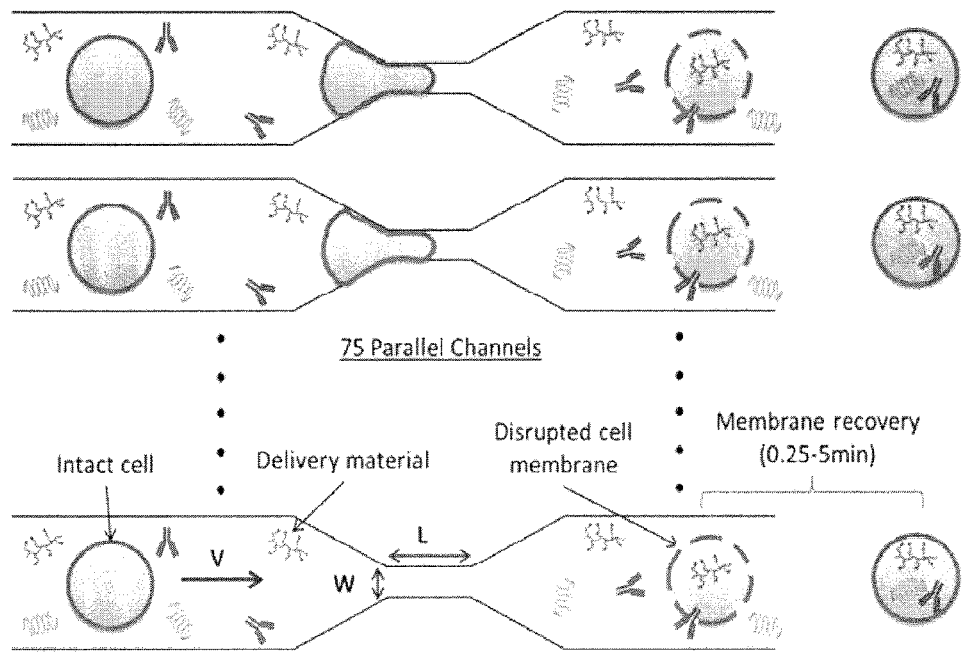

A vector-free microfluidic delivery platform (CellSqueeze) is used to deliver macromolecules directly into the cytosol of primary immune cells, e.g., mouse, human, with minimal cytotoxicity. The principle underlying this approach is temporary membrane disruption by rapid mechanical deformation, or squeezing, of the target cell, which permits the uptake by diffusion of macromolecules in the fluid medium and is followed by cell membrane repair (see, e.g., U.S. Patent Publication No. 20140287509, hereby incorporated by reference. Using a library of microfluidic designs, uptake of test compounds such as dextran polymers, antibodies and small interfering RNAs (siRNA) were delivered into primary human and murine T cells, B cells, monocytes/macrophages, and dendritic cells+. The results demonstrate the utility of the platform to deliver a variety of different sizes and types of macromolecules. Efficient delivery of material to different classes of immune cells, which have a large range of cell diameter (~8-30 μm), distinct morphology, anisotropy and membrane flexibility, required identification of specific conditions for different cell types. For cell squeezing, width of the constriction is a critical parameter, and other parameters such as geometric elements, speed, buffer, and temperature may also affect delivery of cargo. Exemplary constriction widths for delivery of cargo to naïve T or B cells are in the range of 3-4 μm; for delivery to activated T or B cells, 4-6 μm; and for delivery to dendritic cells, 6-8 μm.

Delivery of siRNAs resulted in robust gene knockdown. Moreover, delivery of antiviral siRNAs to CD4+ T cells inhibited HIV replication, demonstrating the functional utility of microfluidic-based delivery. Similarly, delivery of antigenic proteins to dendritic cells and B cells resulted in more effective antigen presentation and greater activation/proliferation of antigen-specific CD8+ T cells in vitro and in vivo. By providing a platform for robust intracellular delivery with minimal loss in viability, cell squeezing represents a flexible and useful tool to probe and control immune cell function for research and clinical applications.

The intracellular delivery of biomolecules, such as proteins and siRNAs, into primary immune cells, especially resting lymphocytes, has been difficult. The vector-free microfluidic platform described herein causes temporary membrane disruption by rapid mechanical deformation of a cell, which leads to intracellular delivery of macromolecules to immune cells such as T cells, B cells, monocytes/macrophages, and dendritic cells. A library of 16 microfluidic device designs was tested for the ability to deliver dextran polymers, siRNA and antibodies to human and murine immune cells. The activity of the delivered material was verified by measuring siRNA-mediated knockdown of CD45, DC-SIGN, and CD4 proteins. Microfluidic delivery, which requires neither viral vectors nor electrical fields, resulted in comparable or better delivery than electroporation, with less cellular toxicity. The technique's utility in disease applications was shown by inhibiting HIV viral replication in primary human CD4 T cells treated with siRNAs directed against viral vif and gag genes. Thus, vector-free microfluidic delivery provides a way to overcome the hurdle of cytosolic delivery of macromolecules to cells which in the past were difficult to engineer (e.g., primary immune cells). The methods and device are therefore useful for engineering of immune cell function.

In certain aspects, the present disclosure relates to methods for preferentially delivering a compound to the cytosol of an immune cell, comprising passing a cell suspension comprising the immune cell through a microfluidic device and contacting the suspension with the compound, wherein the device comprises a constriction of a diameter of about 2 μm, 3 μm, 4 μm, 5 μm, 6 μm, 7 μm, 8 μm, 9 μm, 10 μm or 2 μm-10 μm and wherein the amount of compound delivered to the immune cell is at least 10% greater than that delivered to a non-immune cell. In certain aspects, the present disclosure relates to method for delivering a compound to the cytosol of an immune cell, comprising passing a cell suspension comprising the immune cell through a microfluidic device and contacting the suspension with the compound, wherein the device comprises a constriction of a diameter of about 2 μm, 3 μm, 4 μm, 5 μm, 6 μm, 7 μm, 8 μm, 9 μm, 10 μm or 2 μm-10 μm.

The term 'cell-squeezed' refers to the method comprising passing a cell suspension through a microfluidic device comprising a constriction. In some embodiments, the cell suspension is contacted with the compound, before, concurrently, or after passing through the microfluidic device. In some embodiments, the immune cell comprises at least 10%, 25%, 50%, 2-fold, 5-fold, 10-fold, 20-fold, 25-fold, 50-fold, or more of the compound after passing through the device as compared to an immune cell contacted with the compound without passing through the device.

Engineering Immune Cell Function

By delivering material into the intracellular space of immune cells by transiently disrupting or deforming membrane integrity, internal mechanisms can be interrogated and characterized, and their function manipulated or altered for a diversity of applications.

An effective way to engineer a cell's function and/or understand its inner workings is introduce material (e.g. bioactive molecules) into the cell and directly manipulate intracellular processes. The methods described herein comprise advantages compared to existing or previous approaches, which largely focus on manipulating the content of the media that cells are in and/or signaling through binding to surface receptors. Intracellular delivery to immune cells is a significant challenge using existing or previous technologies. The CellSqueeze platform described herein delivers diverse material into immune cells and has demonstrated the ability to influence cell function in vivo and in vitro. These methods are useful to program (or re-program) immune cell function for clinical use, e.g., adoptive transfer therapies. Moreover, the methods are useful to test and elucidate immunological mechanisms to identify drug targets and/or diagnostics.

Figure 33:
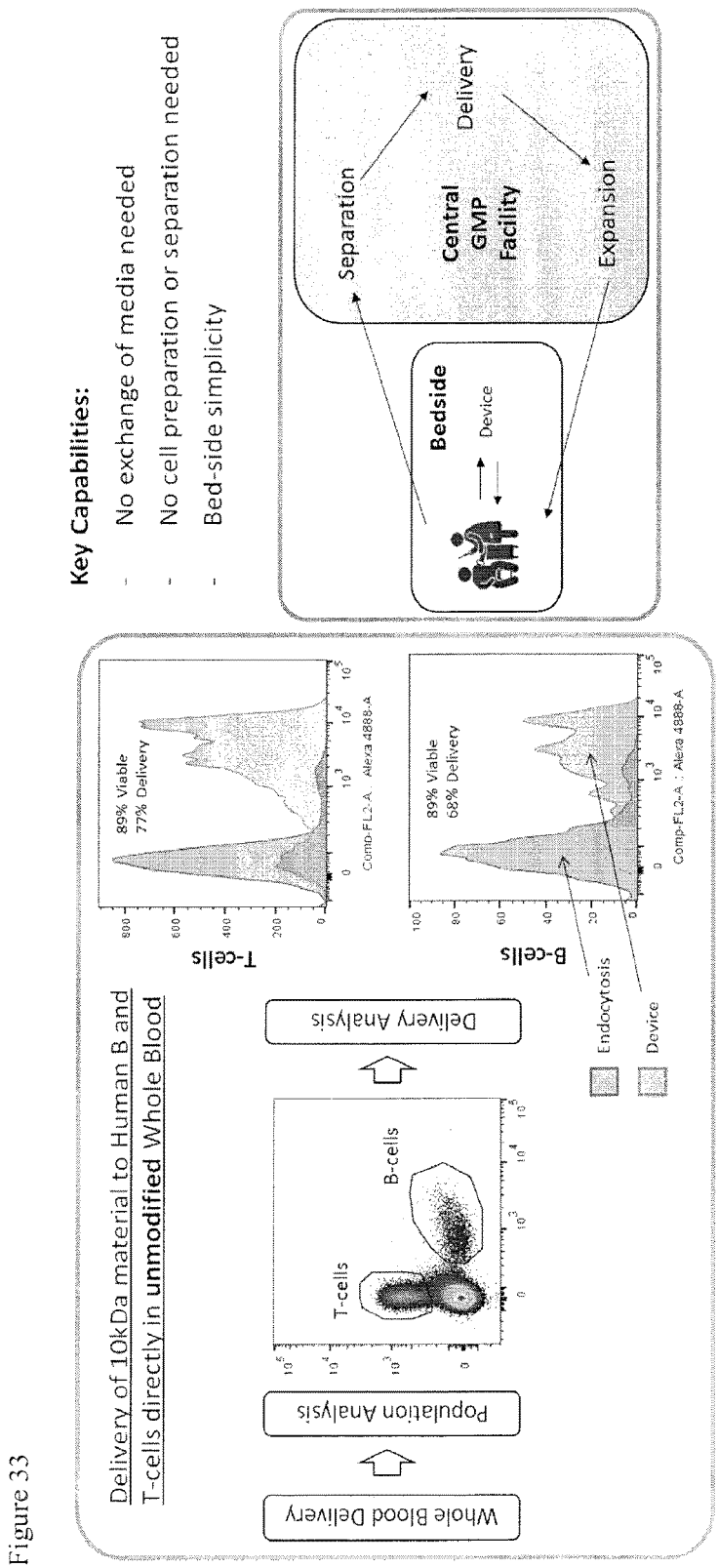
FIG. 33 shows data and a cartoon showing delivery of 10 kDa material to Human B and T-cells directly in unmodified whole blood.
Figure 34:
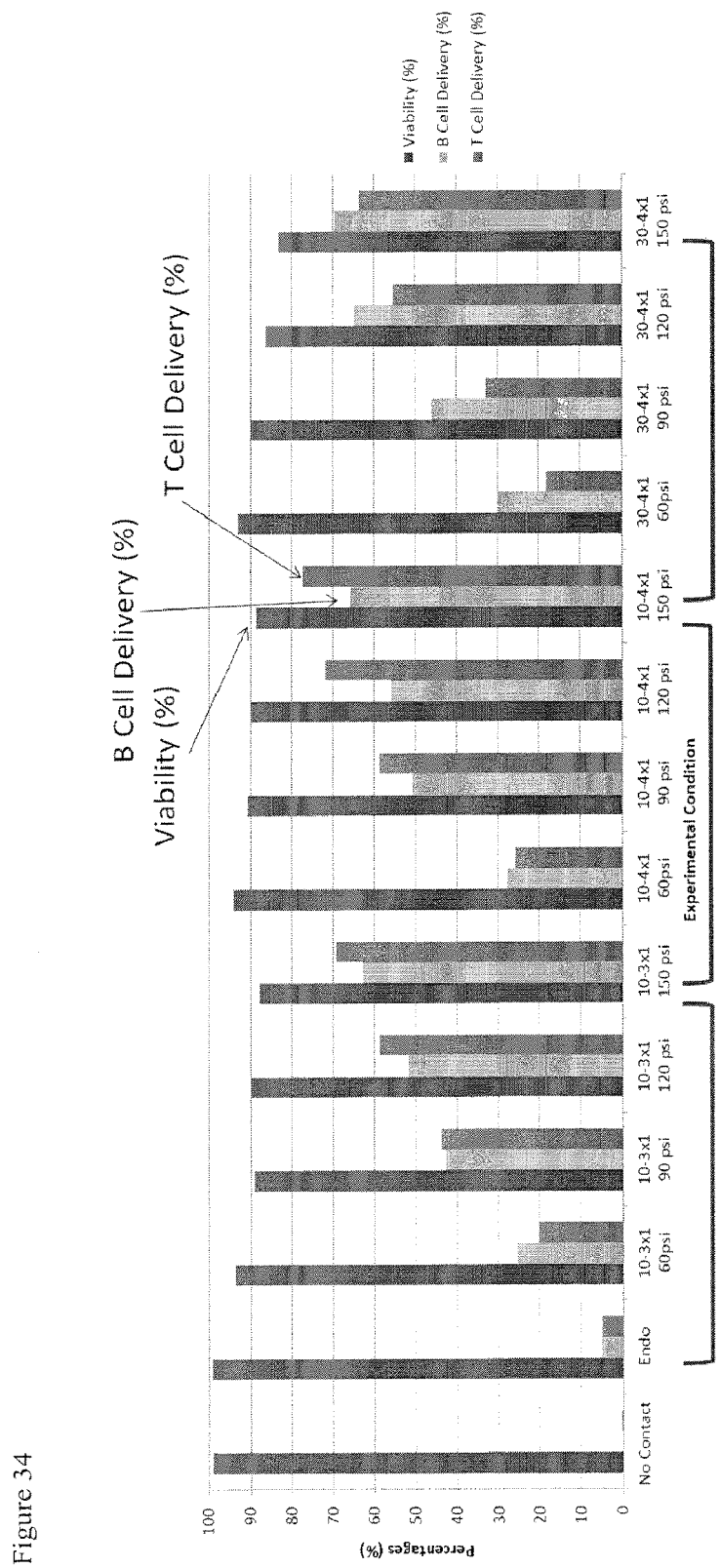
FIG. 34 is a graph showing viability and delivery efficiencies in whole blood.

Aspects of the present invention relate to the surprising discovery that compounds can be delivered to immune cells (such as human B and T cells) while they remain within whole blood. Whole blood is difficult to manipulate without purification, e.g., fractionation or separation of peripheral blood mononuclear cells from red blood cells. However, devices and methods disclosed herein deliver compounds into immune cells within whole blood. The invention enables delivery of compounds to immune cells without the need for separation of the immune cells from whole blood before passing the heterogenous mixture (immune cells, erythrocytes, plasma/serum) through a cell squeezing device. This remarkable result has important technical benefits, and in some instances enables the bedside treatment of patients as well as the ability to process cells in situations without access to cell-fractionation, e.g., a battlefield. For example, a subject may have whole blood removed, processed through a device of the invention, and then reinfused, e.g., in a continuous process. Since the isolation or enrichment of immune cells is not required, less manipulation of the cells is required, and the cells need not be processed using media such as artificial media. Additionally, treating immune cells in whole blood can be performed with high efficiency while maintaining high levels of viability. See, e.g., FIGS. 33 and 34.

In some embodiments that can be combined with the previous embodiments, the cell suspension comprises mammalian cells. In some embodiments, the cell suspension comprises a mixed cell population. In some embodiments, the cell suspension is whole blood. In some embodiments, the cell suspension comprises buffy coat cells. In some embodiments, the cell suspension is lymph. In some embodiments, the cell suspension comprises peripheral blood mononuclear cells. In some embodiments, the cell suspension comprises a purified cell population. In some embodiments, the cell is a primary cell or a cell line cell. In some embodiments, the cell is a blood cell. In some embodiments, the blood cell is an immune cell. In some embodiments, the immune cell is a lymphocyte. In some embodiments, the immune cell is a T cell, B cell, natural killer (NK) cell, dendritic cell (DC), NKT cell, mast cell, monocyte, macrophage, basophil, eosinophil, or neutrophil. In some embodiments, the immune cell is an adaptive immune cell such as a T cell and B cell. In some embodiments, the immune cell is an innate immune cell. Exemplary innate immune cells include innate lymphoid cells (ILC1, ILC2, ILC3), basophils, eosinophils, mast cells, NK cells, neutrophils, and monocytes. In some embodiments, the immune cell is a memory cell. In some embodiments, the immune cell is a primary human T cell. In some embodiments, the cell is a mouse, dog, cat, horse, rat, goat, monkey, or rabbit cell. In some embodiments, the cell is a human cell. In some embodiments, the cell suspension comprises non-mammalian cell. In some embodiments, the cell is a chicken, frog, insect, or nematode cell.

In some examples, the immune cell is in a resting state compared to an activated state, e.g., cells in an activate state generally comprise a larger diameter compared to cells of the same phenotype in a resting state. For example, cells are characterized by expression of the following markers: CD25, KLRG1, CD80, CD86, PD-1, PDL-1, CTLA-4, CD28, CD3, MHC-I, MHC-II, CD62L, CCR7, CX3CR1 and CXCR5, each of which may be modulated (increased or reduced by introducing molecules into the immune cells using the methods described). In some embodiments, the expression of one or more markers is increased on the immune cells by delivery of compounds into the immune cells. In some embodiments, the expression of one or more markers is decreased on the immune cells by delivery of compound into the immune cells. In some embodiments, the expression of one re more markers is increased and the expression of one or more markers is decreased on the immune cells by delivery of compounds into the immune cells. In some embodiments, the immune cell is a naïve immune cell. Naïve immune cells, e.g., T cells, are characterized by comparatively low levels of expression of CD25, CD80, CD86, PD-1, and CTLA-4 and by comparatively high level of CCR7 (compared to activated cells) as compared to the level of expression by activated immune cells.

Aspects of the present subject matter relate to major histocompatibility complexes (MHCs). The major function of MHCs s to bind to peptide fragments derived from pathogens and display them on the cell surface for recognition by the appropriate T cells. In humans, MHCs are also called human leukocyte antigens (HLAs). HLAs corresponding to MHC class I (HLA-A, HLA-B, and HLA-C) present peptides from inside the cell. For example, if the cell is infected by a virus, the HLA system brings fragments of the virus to the surface of the cell so that the cell can be destroyed by the immune system. These peptides are produced from digested proteins that are broken down in the proteasomes. In general and with respect to MHC-1, these particular peptides are small polymers, about 8-10 amino acids in length. Foreign antigens presented by MEW class I attract killer T-cells (also called CD8 positive- or cytotoxic T-cells) that destroy cells. HLAs corresponding to MHC class II (HLA-DP, HLA-DM, HLA-DOA, HLA-DOB, HLA-DQ, and HLA-DR) present antigens from outside of the cell to T-lymphocytes. These particular antigens stimulate the multiplication of T-helper cells, which in turn stimulate antibody-producing B-cells to produce antibodies to that specific antigen. Self-antigens are suppressed by regulatory T cells.

In certain aspects, the present disclosure relates to methods for delivering a compound or composition into a cell. In some embodiments, the compound is a single compound. In some embodiments, the compound is a mixture of compounds. In some embodiments, the compound comprises a nucleic acid. In some embodiments, the compound is a nucleic acid. Exemplary nucleic acids include, without limitation, recombinant nucleic acids, DNA, recombinant DNA, cDNA, genomic DNA, RNA, siRNA, mRNA, saRNA, miRNA, lncRNA, tRNA, and shRNA. In some embodiments, the nucleic acid is homologous to a nucleic acid in the cell. In some embodiments, the nucleic acid is heterologous to a nucleic acid in the cell. In some embodiments, the compound is a plasmid. In some embodiments, the nucleic acid is a therapeutic nucleic acid. In some embodiments, the nucleic acid encodes a therapeutic polypeptide.

In some embodiments the nucleic acid encodes a reporter or a selectable marker. Exemplary reporter markers include, without limitation, green fluorescent protein (GFP), red fluorescent protein (RFP), auquorin, beta-galactosidase, Uroporphyrinogen (urogen) III methyltransferase (UMT), and luciferase. Exemplary selectable markers include, without limitation, Blasticidin, G41 8/Geneticin, Hygromycin B, Puromycin, Zeocin, Adenine Phosphoribosyltransferase, and thymidine kinase. In some embodiments, the compound is a nucleic acid encoding for a MHC complex. In some embodiments, the compound is a nucleic acid encoding for a MHC class I or MHC class II complex. In some embodiments, the nucleic acid encodes for a chimeric antigen receptor, such as a chimeric T cell receptor. In some embodiments, the nucleic acid encodes for a recombinant T cell receptor. For example, nucleic acids encoding chimeric antigen receptors are introduced into a T cell in a virus-free way, i.e., by cell squeezing, to maintain expression of CAR-T. For example, introduction of DNA is accomplished without the use of a viral particle. Nucleic acid constructs may however include viral genome elements, which may help the integration or be maintained as an extrachromosomal nucleic acid.

In some embodiments, the compound comprises a protein or polypeptide. In some embodiments, the compound is a protein or polypeptide. In some embodiments, the protein or polypeptide is a therapeutic protein, antibody, fusion protein, antigen, synthetic protein, reporter marker, or selectable marker. In some embodiments, the protein is a gene-editing protein or nuclease such as a zinc-finger nuclease (ZFN), transcription activator-like effector nuclease (TALEN), mega nuclease, or CRE recombinase. In some embodiments, the fusion proteins can include, without limitation, chimeric protein drugs such as antibody drug conjugates or recombinant fusion proteins such as proteins tagged with GST or streptavidin. In some embodiments, the compound is a transcription factor. Exemplary transcription factors include, without limitation, Oct5, Sox2, c-Myc, Klf-4, T-bet, GATA3, FoxP3, and RORγt. In some embodiments, the nucleic acid is a transposon. A transposon, or transposable element, is a DNA segment that inserts itself into another position within the genome.

In some embodiments, the compound comprises an antigen. In some embodiments, the compound is an antigen. An antigen is a substance that stimulates a specific immune response, such as a cell or antibody-mediated immune response. Antigens bind to receptors expressed by immune cells, such as T cell receptors (TCRs), which are specific to a particular antigen or to antigen presentation molecules such as MHC/HLA heterodimers. Antigen-receptor binding subsequently triggers intracellular signaling pathways that lead to downstream immune effector pathways, such as cell activation, cytokine production, cell migration, cytotoxic factor secretion, and antibody production. In some embodiments, the compound comprises a disease-associated antigen. In some embodiments, antigens are derived from foreign sources, such as bacteria, fungi, viruses, or allergens. In some embodiments, antigens are derived from internal sources, such as tumor cells or self-proteins (i.e. self-antigens). In some embodiments, the tumor antigen is in a tumor lysate. Self-antigens are antigens present on an organism's own cells. Self-antigens do not normally stimulate an immune response, but may in the context of autoimmune diseases, such as Type I Diabetes or Rheumatoid Arthritis, Multiple Sclerosis (and other demyelinating disorders). In some embodiments, the antigen is a neoantigen. Neoantigens are antigens that are absent from the normal human genome, but are created within oncogenic cells as a result of tumor-specific DNA modifications that result in the formation of novel protein sequences. Exemplary viral antigens include HIV antigens, Ebola antigen, HPV antigens, and EBV antigens, which are purified or delivered as a mixture, or delivered as killed or attenuated virus or virus fragments. In some embodiments, the HPV antigens are derived from the oncogenes E6 and E7 of HPV16. In some embodiments, the compound comprises cell lysate from tissue infected with an unknown pathogen. In some embodiments, the antigen is a non-protein antigen, such as a lipid, glycolipid, or polysaccharide.

In some embodiments the protein or polypeptide is a reporter or a selectable marker. Exemplary reporter markers include, without limitation, green fluorescent protein (GFP), red fluorescent protein (RFP), auquorin, beta-galactosidase, Uroporphyrinogen (urogen) III methyltransferase (UMT), and luciferase. Exemplary selectable markers include, without limitation, Blasticidin, G418/Geneticin, Hygromycin B, Puromycin, Zeocin, Adenine Phosphoribosyltransferase, and thymidine kinase.

In some embodiments, the compound comprises a small molecule. In some embodiments, the compound is a small molecule. Exemplary small molecules include, without limitation, fluorescent markers, dyes, pharmaceutical agents, metabolites, or radionucleotides. In some embodiments, the pharmaceutical agent is a therapeutic drug and/or cytotoxic agent.

In some embodiments, the compound comprises a nanoparticle. Examples of nanoparticles include gold nanoparticles, quantum dots, carbon nanotubes, nanoshells, dendrimers, and liposomes. In some embodiments, the nanoparticle contains or is linked (covalently or non-covalently) to a therapeutic molecule. In some embodiments, the nanoparticle contains a nucleic acid, such as mRNA or cDNA. In some embodiments, the nanoparticle contains a label, such as a fluorescent or radioactive label.

Aspects of the present invention relate to the improved delivery of intracellular antibodies. Non-limiting examples of intracellular antibodies are described in U.S. Pat. No. 6,004,940, issued Dec. 21, 1999; U.S. Pat. No. 6,329,173, issued Dec. 11, 2001; U.S. Patent Application Publication No. 2010/0143371, published Jun. 10, 2010; and U.S. Patent Application Publication No. 2006/0034834, published Feb. 16, 2006, the contents of each of which are incorporated herein by reference. A limitation impacting the usefulness of intracellular antibodies has been expressing them in cells of interest, including cells within whole blood. The present invention overcomes this limitation, and enables isolated antibodies, or constructs encoding antibodies, to be delivered to the cytosol of immune cells.

The invention encompasses not only delivery of an intact monoclonal antibody, but also an immunologically-active antibody fragment, e.g., a Fab or (Fab)2 fragment; an engineered single chain Fv molecule; or a chimeric molecule, e.g., an antibody which contains the binding specificity of one antibody, e.g., of murine origin, and the remaining portions of another antibody, e.g., of human origin. In another example, the chimeric molecule is a fusion of single-chain variable fragment (scFv) derived from a monoclonal antibody fused to CD3-zeta transmembrane and endodomain. Such molecules result in the transmission of a zeta signal in response to recognition by the scFv of its target. The variable portions of an immunoglobulin heavy and light chain are fused by a flexible linker to form a scFv. This scFv is preceded by a signal peptide to direct the nascent protein to the endoplasmic reticulum and subsequent surface expression. A flexible spacer allows the scFv to orient in different directions to enable antigen binding. The transmembrane domain is a typical hydrophobic alpha helix usually derived from the original molecule of the signaling endodomain which protrudes into the cell and transmits the desired signal. Such chimeric antigen receptors are delivered to T cells using the microfluidic squeeze method described herein.

In some embodiments, the compound comprises a chimeric antigen receptor (CAR). In some embodiments, the compound is a chimeric antigen receptor (CAR). In some embodiments, the CAR is a fusion of an extracellular recognition domain (e.g., an antigen-binding domain), a transmembrane domain, and one or more intracellular signaling domains. Upon antigen engagement, the intracellular signaling portion of the CAR can initiate an activation-related response in an immune cell, such as the release of cytokines or cytolytic molecules. In some embodiments, the CAR is a chimeric T-cell antigen receptor. In some embodiments, the CAR contains an antigen-binding domain specific to a tumor antigen. In some embodiments, the CAR antigen-binding domain is a single-chain antibody variable fragment (scFv). In some embodiments, the compound enhances T cell function. In some embodiments, the compound that enhances T cell function is an immune checkpoint pathway inhibitor. Exemplary immune checkpoint pathway inhibitors include, without limitation, programmed death-1 pathway inhibitors, a programmed death ligand-1 pathway inhibitors, and an anti-cytotoxic T-lymphocyte antigen 4 pathway inhibitors. For example, the immune checkpoint pathway inhibitors can target SHP2, a tyrosine phosphatase that is involved in PD-1 and CTLA-4 signaling.

In some embodiments, the compound comprises a fluorescently tagged molecule. In some embodiments, the compound is a fluorescently tagged molecule, such as a molecule tagged with a fluorochrome such as pacific blue, Alexa 288, Cy5, or cascade blue. In some embodiments, the compound is a radionucleotide, dextran particle, magnetic bead, or impermeable dye. In some embodiments, the compound is a 3 kDa dextran particle labeled with PacBlue. In some embodiments, the compound is a 10 kDa dextran particles labeled with Alexa488. In some embodiments, the compound is a small molecule fluorophore tagged protein. In some embodiments, the compound is a small molecule tagged with Alexa647. In some embodiments, the compound comprises a virus or virus-like particle. In some embodiments, the virus is a therapeutic virus. In some embodiments, the virus is an oncolytic virus. In some embodiments, the virus or virus-like particle contains nucleic acid encoding for a therapeutic molecule, such as a therapeutic polypeptide.

In some embodiments, the compound comprises a tolerogenic factor. In some embodiments, the compound comprises an adjuvant. In some embodiments, the compound comprises a differentiation factor. Exemplary differentiation factors to be delivered to the cytosol of T cells to promote differentiation and/or activation/maturation of T cells include T-box transcription factors T-bet and Eomesodeimin (Eomes), NFKB and/or forkhead box P3 (FOXP3).

Exemplary compounds and compositions for intracellular delivery include:

Nucleic acids, particularly: DNA (plasmid or other oligos) and RNA (e.g. siRNA, mRNA, tRNA, saRNA, lncRNA, miRNA, guide RNA) chemically, biologically or otherwise modified. Proteins: e.g. antibodies, inhibitors, enzymes (e.g. kinases), transcription factors, ribosomes, antigens, cell lysates;

Peptides: long (100-10,000 amino acids) and short (1-100 amino acids) Nanomaterials: e.g. lipid-based nanoparticles, polymeric nanoparticles, carbon nanotubes, quantum dots, metallic nanoparticles (including gold);

Virus: Cytoplasmic delivery of viral (or virus-like) particles yield successful gene delivery for cells that are otherwise resistant to infection. Use of a replication incompetent virus represents an additional means of manipulating cell function;

Other materials: polymers, dyes, TrisNTA, small molecule drugs, adjuvants, probes;

Mixtures of any combination of the above.

Exemplary cell types info which compounds/compositions are delivered (all adaptive and innate immune cells) include:

All mammalian species, e.g., human, mouse, dog, cat, horse, monkey

B cells (e.g. naïve B cells, plasmablasts);

T cells (e.g. Th1, Th17, Th2, Treg, CD8, CD4, Trm, Tem, Tcm);

Dendritic cells (e.g. pDCs, monocyte derived DCs, cDCs, $CD8^+$ DCs, $CD11b^+$ DCs;

Monocytes, macrophage;

Neutrophils, NK cells, innate lymphoid cells (ILC1, ILC2, ILC3), basophils, granulocytes and mast cells.

Precursor cells, (hematopeotic stem cells, CLPs, mesenchymal stem cells)

Engineering Immune Cell Antigen Presentation

Certain aspects of the present disclosure relate to a method for engineering of immune cell function comprising intracellular delivery of compounds by transiently disrupting a membrane surrounding the cytoplasm of the immune cell and delivering into the cytosol an antigen. In some embodiments, the antigen comprises a length of greater than 7, 8, 9 or 10 amino acids and wherein the immune cell processes the antigen and displays a class I histocompatibility antigen restricted processed form of the antigen on a surface of the immune cell.

Certain aspects of the present disclosure relate to a method for engineering of immune cell function comprising intracellular delivery of a compound by passing an immune cell through a microfluidic device comprising a constriction and contacting the immune cell with the compound. In some embodiments, the compound comprises an antigen and the immune cell processes the antigen and displays the antigen on a surface of the immune cell. In some embodiments, the immune cell displays a class I histocompatibility antigen restricted processed form of the antigen on a surface of the immune cell. In some embodiments, the immune cell displays a class II histocompatibility antigen restricted processed form of the antigen on a surface of the immune cell. In some embodiments, the cell membrane is disrupted by passing the immune cell through a constriction of a diameter of 2 μm-10 μm. In some embodiments, the antigen comprises a full-length, unprocessed protein. In some embodiments, the immune cell is contacted with an effector T cell, such as a CD8+ T cell and activates a cytotoxic T cell immune response. In some embodiments, the immune cell is contacted with an effector T cell, such as a CD4+ T cell, and activates a helper T cell immune response. In some embodiments, immune cell is contacted with an effector T cell and activates a tolerogenic T cell immune response. In some embodiments, the immune cell comprises a B cell, dendritic cell or macrophage. In some embodiments, the immune cell comprises a T cell.

Certain aspects of the present disclosure relate to a method for conferring an antigen presenting phenotype on a T cell, comprising delivering a whole, unprocessed antigen to the cytosol of a T cell by passing the T cell through a microfluidic device, wherein the device comprises a constriction of a diameter of 2 μm-10 μm and wherein the T cell comprises a class I histocompatibility antigen restricted processed form of the antigen on a surface of the immune cell following passage through the microfluidic device. Certain aspects of the present disclosure relate to a method for conferring an antigen presenting phenotype on a T cell, comprising delivering a whole, unprocessed antigen to the cytosol of a T cell by passing the T cell through a microfluidic device, wherein the device comprises a constriction of a diameter of 2 μm-10 μm and wherein the T cell comprises a class II histocompatibility antigen restricted processed form of the antigen on a surface of the immune cell following passage through the microfluidic device. In some embodiments, the antigen comprises a tumor antigen or a viral antigen. In some embodiments, the T cell is further contacted with a second T cell, the second T cell comprising a class I histocompatibility antigen restricted cytotoxic T cell phenotype. In some embodiments, the T cell is further contacted with a second T cell, the second T cell comprising a class II histocompatibility antigen restricted helper T cell phenotype.

Certain aspects of the present disclosure relate to the use of a cell-squeezed, antigen loaded T cell to activate a cytotoxic T cell response specific for an antigen. Certain aspects of the present disclosure relate to the use of a cell-squeezed, antigen loaded T cell to activate a helper T cell response specific for an antigen. Certain aspects of the present disclosure relate to the use of a cell-squeezed, antigen loaded T cells to induce a tolerogenic T cell response specific for an antigen.

Engineering Immune Cell Homing

Certain aspects of the present disclosure relates to a method for conferring a homing phenotype to an immune cell, comprising delivering a compound to the cytosol of a T cell by passing the immune cell through a microfluidic device, wherein the device comprises a constriction of a diameter of 2 μm-10 μm and wherein the compound confers the expression of a homing phenotype to the immune cell. For example, the delivered compounds can increase the expression of chemokine receptors that direct homing to a particular site and downregulate the expression of conflicting chemokine receptors.

In some embodiments, the compound comprises a nucleic acid. In some embodiments, the compound is a nucleic acid. Exemplary nucleic acids include, without limitation, recombinant nucleic acids, DNA, recombinant DNA, cDNA, genomic DNA, RNA, siRNA, mRNA, saRNA, miRNA, lncRNA, tRNA, and shRNA.

In some embodiments, the compound comprises a protein or polypeptide. In some embodiments, the compound is a protein or polypeptide. In some embodiments, the protein is a gene-editing protein or nuclease such as a zinc-finger nuclease (ZFN), transcription activator-like effector nuclease (TALEN), mega nuclease, or CRE recombinase. In some embodiments, the compound is a transcription factor. Exemplary transcription factors include, without limitation, Oct5, Sox2, c-Myc, Klf-4, T-bet, GATA3, FoxP3, and RORγt. In some embodiments, the transcription factor induces the cellular expression of MHC complexes.

In some embodiments, the compound comprises a chimeric antigen receptor (CAR). In some embodiments, the compound is a chimeric antigen receptor (CAR). In some embodiments, the CAR is a fusion of an extracellular recognition domain (e.g., an antigen-binding domain), a transmembrane domain, and one or more intracellular signaling domains. Upon antigen engagement, the intracellular signaling portion of the CAR can initiate an activation-related response in an immune cell, such as homing to a particular tissue or physiological location. In some embodiments, the CAR is a chimeric T-cell antigen receptor.

Engineering Immune Cells for Tolerance

Certain aspects of the present disclosure relates to a method for conferring a tolerogenic phenotype to an immune cell, comprising delivering a compound to the cytosol of a T cell by passing the immune cell through a microfluidic device, wherein the device comprises a constriction of a diameter of 2 µm-10 µm and wherein the compound induces the differentiation of the immune cell into a cell with a tolerogenic phenotype. In some embodiments, the compound comprises a nucleic acid. In some embodiments, the compound is a nucleic acid. Exemplary nucleic acids include, without limitation, recombinant nucleic acids, DNA, recombinant DNA, cDNA, genomic DNA, RNA, siRNA, mRNA, saRNA, miRNA, lncRNA, tRNA, and shRNA.

Certain aspects of the present disclosure relate to a method of treating a patient by introducing the immune cells modified according to the methods described to a patient. In some embodiments, the immune cells are for use in immunosuppressive therapy. In some embodiments, the cells are isolated from a patient, modified according to the methods described herein, and introduced back into the patient. In some embodiments, an immune checkpoint inhibitor is further administered to the patient.

Engineering Kamikaze Immune Cells

Certain aspects of the present disclosure relates to a method for generating a Kamikaze immune cell, comprising delivering self-amplifying RNA to the cytosol of a T cell by passing the immune cell through a microfluidic device, wherein the device comprises a constriction of a diameter of 2 µm-10 µm and wherein the self-amplifying RNA encodes for continual production of an encoded protein. In some embodiments, the compound comprises a nucleic acid. In some embodiments, the compound is a nucleic acid. In some embodiments, the nucleic acid is self-amplifying RNA (saRNA).

Screening Antigens for Vaccine Development

In some embodiments, immune cells modified according to the methods described herein are used to screen antigens for vaccine development. For example, a tumor cell lysate is delivered to antigen presenting cells, T cells, or B cells using the squeeze method described herein. The APC are incubated with patient-derived T cells or T cell clones/lines to determine the identity of vaccine candidate antigens. In another approach, the antigen processed and presented by the tumor-lysate loaded APCs is identified by Mass Spectroscopy. Antigens identified in this manner are then subsequently used for vaccination.

Immune Cell Trafficking

Certain aspects of the present disclosure relate to a method of determining T cell trafficking within a patient, comprising delivering a label into a T cell according to the methods described herein and administering the labeled T cell into a patient, wherein T cell trafficking within the patient can be determined by detecting the labeled T cell. In some embodiments, The label is a fluorescent or radioactive label. In some embodiments, the T cell trafficking is trafficking to a tumor. For example, T cells can be isolated from a patient, passed through the microfluidic device in order to deliver an isotope into the T cells, and injected back into the patient. Imaging methods, such as a PET scan, can then be used to detect the label and track the trafficking of the T cells through the body.

Antigen Presentation for Vaccines

Because the system enables delivery of proteins preferentially to immune cells, it is useful to engineer such cells for use in vaccination of a patient (human, mouse, non-human primate, etc.) against a target of interest. By delivering specific antigenic proteins (or mixtures of antigenic proteins, mixtures of proteins+adjuvant, or peptides corresponding to fragments of the proteins) directly to the cytosol of a target cell (e.g., a DC, T cell or B cell), MHC class I presentation of an antigen is induced which subsequently drives CD8 T cell mediated immunity against a target disease, e.g., cancer or a pathogenic microbial infection such as a viral infection. The optional use of adjuvants in this process enhances the response (e.g. co-delivery of a material that enhances efficacy or incubation of cells in presence of an adjuvant factor). The ability to manipulate immune cells, which prior to the invention, have been difficult or impossible to engineer, permits therapeutic and prophylactic vaccine applications which were not possible prior to the invention, especially for currently challenging diseases such as cancer and HIV. Other manifestations include co-delivering materials to enhance cell survival, so that the cells can present antigen for longer; vaccination against multiple antigens simultaneously; vaccination in conjunction with the delivery of (or exposure to) activating factors to provide adjuvant effects and enhance the immune response; and/or rapid-response vaccines using cell lysate as the antigen source. In the latter example (vaccination against a new unknown pathogen/disease), infected or cancerous cells are taken from a patient, e.g. by tissue sampling or biopsy, and the lysate of these cells is delivered to immune cells using the strategy described above. This approach raises an immune response against antigens associated with that unknown disease without one knowing a priori the identity of the antigens.

Vaccine Adjuvants

Adjuvants or immune response activators/potentiators are used to boost elicitation of an immune cell, e.g., T cell, response to a vaccine antigen. In some embodiments, an immune cell is contacted with an adjuvant after the immune cell passes through the microfluidic device. For example the cell is contacted with the adjuvant about 5 minutes to about 2 hours after passing through the microfluidic device or any time or range of times therebetween. For example, the cell is contacted with the adjuvant about 5 minutes to about 1.5 hours, about 5 minutes to about 1 hour, about 5 minutes to about 45 minutes, about 5 minutes to about 30 minutes, about 5 minutes to about 15 minutes, or about 5 minutes to about 10 minutes after passing through the microfluidic device. In some embodiments, the cell is contacted with the adjuvant about 10 minutes to about 2 hours, about 15 minutes to about 2 hours, about 30 minutes to about 2 hours, about 45 minutes to about 2 hours, about 1 hour to about 2 hours, or about 1.5 hours to about 2 hours after passing through the microfluidic device. In addition to classic adjuvants such as alum or water-in-oil emulsions (e.g., Freund's Incomplete Adjuvant and MF59®), other adjuvants such as ligands for pattern recognition receptors (PRR), act by inducing the innate immunity, targeting the APCs and consequently influencing the adaptive immune response. Members of nearly all of the PRR families are targets for adjuvants. These include Toll-like receptors (TLRs), NOD-like receptors (NLRB), RIG-I-like receptors (RLRs) and C-type lectin receptors (CLRs). They signal through pathways that involve distinct adaptor molecules leading to the activation of different transcription factors. Transcription factors (NF-κB, IRF3) induce the production of cytokines and chemokines that play a key role in the priming, expansion and polarization of the immune responses. Activation of some members of the NLR family, such as NLRP3 and NLRC4, triggers the formation of a protein complex, called inflammasome, implicated in the induction of the pro-inflammatory cytokines IL-1β and IL-18. The NLRP3 and NLRC4 inflammasomes have been involved in the innate immunity induced by certain adjuvants but their mechanism of action remains unclear.

Natural ligands or synthetic agonists for PRRs, either alone or with various formulations. PRR activation stimulate the production of pro-inflammatory cytokines/chemokines and type I IFNs that increase the host's ability to eliminate pathogens. The incorporation of pathogens associated molecular patterns (PAMPs) in vaccine formulations improves and accelerates the induction of vaccine-specific responses. Used in combination with alum or classical emulsion adjuvants, PAMPS are useful to drive an immune response towards a Th1 response.

TLR3 and RLR Ligands. Double-stranded RNA (dsRNA), which is produced during the replication of most viruses, is a potent inducer of innate immunity. Synthetic analogs of dsRNA, such as poly(I:C) are useful as adjuvants. They act through TLR3 and RIG-I/MDA-5, inducing IL-12 and type I IFNs production, facilitating antigen cross-presentation to MHC class II molecules, and improving generation of cytotoxic T cells.

TLR4 Ligands. Bacterial lipopolysaccharides (LPS), which are ligands for TLR4, have long been recognized as potent adjuvants, but their pyrogenic activity prevented their clinical use. The development of less toxic derivative includes monophosphoryl lipid A (MPLA). MPLA is useful as an adjuvant and to drive the immune response to a Th1 response.

TLR5 Ligands. The TLR5 ligand, bacterial flagellin, is a potent T-cell antigen and has potential as a vaccine adjuvant. Unlike other TLR agonists, flagellin tends to produce mixed Th1 and Th2 responses rather than strongly Th1 responses. Flagellin can be used as an adjuvant mixed with the antigen or fused to a recombinant vaccine antigen.

TLR7/8 Ligands. These ligands, specialized in the recognition of single stranded viral RNA, are also useful vaccine adjuvants. For example, Imidazoquinolines (i.e. imiquimod, gardiquimod and R848) are synthetic compounds that activate TLR7/8 in multiple subsets of dendritic cells leading to the production of IFN-α, and IL-12 thus promoting a Th1 response.

TLR9 Ligands. Oligodeoxynucleotides containing specific CpG motifs (CpG ODNs such as ODN 1826 and ODN 2006) are recognized by TLR9. They enhance antibody production as well as drive/promote Th cell responses to Th1 and away from Th2 responses.

NOD2 Ligands. Fragments of bacterial cell walls, such as muramyl dipeptide (MDP), are well known adjuvants. MDP triggers the activation of NOD2 and the NLRP3 inflammasome.

These classes of adjuvants, e.g., modulators of PRR pathways, are useful in vaccines due to their ability to induce strong cell-mediated immunity. Preferred adjuvants include CpG oligodeoxynucleotide, R848, lipopolysaccharide (LPS), rhIL-2, anti-CD40 or CD4O L, IL-12, and/or dicyclic nucleotides.

Engineering T Cells for Immunotherapy

Certain aspects of the present disclosure relate to a method of treating a patient by introducing the immune cells modified according to the methods described to a patient. In some embodiments, the immune cells are for use in immunotherapy. For example, by enabling delivery of a diversity of material to T cells, T cell function is engineered to target a disease of interest. For example, by delivering chimeric antigen receptors, or DNA/mRNA for a TCR that targets the antigen of interest, T cells that are specific against a disease antigen and prompt a killer (and or helper) T cell response are generated. Other materials, such as NF-kB, Bcl-2, Bcl-3, Bcl-xl, upregulators of CD3/CD28, CpG, R848, suppressors of PD-1, suppressors of PDL-1, suppressors of CTLA-4 are delivered to enhance cell activity and survival.

For example, one common challenge in current adoptive T cell transfer therapies is that the activated T cells are exposed to the immunosuppressive microenvironment of the tumor and become exhausted/anergic thus minimizing their efficacy. Intracellular delivery using the methods described are used to disrupt immunosuppression pathways [e.g. by deletion of immunosuppressive genes CTLA-4, PD-1, PD-2, PD1-1, PD1-2, or siRNA mediated knockdown, or small molecule inhibitor/antibody based suppression using known methods such as Transcription activator-like effector nucleases (TALENS), or zinc finger nuclease (ZFN) based approaches)] and thus allow these T cells to retain their highly activated, killer state in the tumor environment. Moreover, this approach is used to induce T cells to become memory cells by co-delivery of appropriate factors to drive differentiation to that phenotype (thus providing better long-term protection). In conventional adoptive transfer, the T cells being introduced into the patient are already in an activated, semi-exhausted state due to proliferation. The methods described herein are used to reset their phenotype to a naïve state. Thus, the cells become capable of much more in vivo proliferation post-transfer and no longer have an exhausted phenotype.

In some embodiments, the methods of the present disclosure are used to generate antigen specific T cells ex vivo. For example, antigen is delivered to an immune cell, such as a DC, and the antigen loaded immune cell is then cultured with patient-derived T cells to activate them in vitro. These T cells can then be expanded through further stimulation before being re-injected into the patient.

Antigen Presentation for Tolerance:

To induce tolerance to the cell-presented antigen, the cell is further contacted with a tolerogen such as thymic stromal lymphopoietin, dexamethasone, vitamin D, retinoic acid, rapamycin, aspirin, transforming growth factor beta, interleukin-10, or vasoactive intestinal peptide together with antigen(s) one could induce tolerance instead.

Tumors and T Cell Tolerance

In the tumor microenvironment, tumor reactive T cells can become tolerized. This is due to multiple suppressive mechanisms, including the tolerogenic activity of other cells associated with tumor development (Anderson et al., J

*Immunol* 2007, 178:1268-1276; Probst et al., *Nat Immunol* 2005, 6:280-286). Antibody-based drugs that block signaling through checkpoint receptors, such as CTLA-4 and PD-1, have yielded anti-tumor responses in both primary and metastatic disease. Malignant tumors that responded to checkpoint blockade have high mutation frequencies and are infiltrated by T-cells reactive to cancer antigens (Taneja, *J Urol* 2012, 188:2148-2149; Brahmer et al., *N Engl J Med* 2012, 366:2455-2465; Wolchok et al., *N Engl Med* 2013, 369:122-133). While this approach has been successful for certain indications, the existence of multiple inhibitory checkpoint surface receptors can undermine the application of the currently limited panel of function blocking antibodies available for immunotherapy. Furthermore, the requirement for systemic treatment with multiple blocking antibodies can have increased toxicity (Ribas et al., *N Engl J Med* 2013, 368:1365-1366; Weber et al., *Cancer* 2013, 119:1675-1682), especially when used in combination (reviewed in Postow et al., *J Clin Oncol* 2015, 33:1974-1982 and Gao et al., *Oncogene* 2015). In some aspects of the invention, dramatic improvements in patient outcomes are achieved by suppressing inhibition pathways in tumor reactive T cells only. In non-limiting examples, this may be achieved by inhibiting or enabling genetic knockdown or knockout of inhibitory pathways within T-cells used in adoptive transfer approaches, such as tumor infiltrating lymphocytes (TIL), recombinant TCRs, and chimeric antigen receptor (CAR) T cells.

SHP2 is a ubiquitous tyrosine phosphatase that, upon activation in T-cells, dampens TCR signaling, and in turn the T-cell response against cancer cells. Signaling through SHP2 by several immune checkpoint receptors diminishes T-cell activity. Inhibitory receptors that activate SHP2 include, but are not limited to, PD-1 (Yokosuka et al., *J Exp Med* 2012, 209:1201-1217), CTLA-4 (Marengere et al., *Science* 1996, 272:1170-1173), BTLA (Watanabe et al., *Nat Immunol* 2003, 4:670-679) and LAIR-1 (Lebbink et al., *J Immunol* 2004, 172:5535-5543) (also reviewed in Nirschl et al., *Clin Cancer Res* 2013, 19:4917-4924). In some embodiments, the genetic inactivation or down-regulation (for example, using RNA interference) of SHP2 in tumor-reactive T cells provides an antitumor response analogous to blocking signaling of several inhibitory checkpoint receptors. Such embodiments may have advantages (such as reduced side effects) over the therapeutic use of sodium stibogluconate (SSG), a pharmacological inhibitor of tyrosine phosphatases, including SHP-1 and -2, in combination with other anti-tumor immunotherapies (Yi et al., *Oncotarget* 2011, 2:1155-1164; Naing et al., *J Cancer* 2011, 2:81-89; Pathak et al., *J Immunol* 2001, 167:3391-3397). SHP2 has been shown to play T cell extrinsic roles, and the inhibition of this molecule on T-cells specifically could eliminate any potential side effects associated with a systemic inhibition of its function. Moreover, by targeting multiple inhibitory signaling pathways through genetic disruption or down-regulation of a single intracellular signaling molecule in T cells, greater efficacy than combinations of T cell adoptive transfer and system checkpoint blockade are achieved. In some embodiments, proteins or nucleic acids, e.g., siRNA, a small molecule inhibitor, an antibody, a Transcription activator-like effector nuclease, or a zinc finger nuclease, are delivered to immune cells, e.g., T cells, to modulate expression of a gene or activity of a gene product such as SHP2 to modify the behavior or function of the T cell. For example, Shpt impaired CD8 T-cells have higher potency of controlling tumor progression than non-impaired cells.

The challenges of modulating gene expression in T cells associated with earlier approaches have been overcome using CellSqueeze devices and methods described herein. Non-limiting aspects of CellSqueeze devices are discussed in the Proceedings of the National Academy of Sciences (Sharei et al., *Proc Natl Acad Sci USA* 2013, 110:2082-2087) and *Nano Letters* (Lee et al., *Nano Lett* 2012, 12:6322-6327), the entire contents of each of which are hereby incorporated herein by reference. For example, CellSqueeze technology may include a microfluidic chip capable of rapidly deforming cells as they pass through a constriction to temporarily disrupt their membrane and enable transport of the target material to the cell cytoplasm. Moreover, by eliminating the need for electrical fields (e.g., in some embodiments, the device and method do not include exposure or application of the cells to an electric field) or potentially toxic exogenous materials, CellSqueeze technology minimizes the potential for cell toxicity and off-target effects. The microfluidic designs and treatment processes described herein are capable of generating more effective engineered T cell therapies for a variety of cancer indications.

Engineering T Cells for Immunosuppression

Auto-immune diseases often involve self-reactive immune cells that are damaging healthy tissue. Intracellular delivery of FoxP3 (and/or other factors) to T cells is used to generate regulatory T cells to counter auto-immunity. These Tregs are generated for broad systemic immunosuppression or to reprogram a self-antigen specific T cell to a Treg phenotype. The latter results in the Treg homing to the same target site as the cells that are perpetuating the auto-immunity and induce localized suppression of their activity.

Self-Amplifying RNA (sa RNA)

Self-amplifying RNAs provide unique capabilities, because not only do they express the protein of interest, but they also replicate their sequence cytoplasmically with no risk of integration into the host genome. Thus introduction of self-amplifying RNA into immune cells is useful to engineer immune cell function. Some specific manifestations include Kamikaze immune cells, alternatives to protein delivery, or continual modulation of cell function, each of which is described below.

Kamikaze Immune Cells

For vaccination or immunosuppression strategies similar to those described above, saRNAs that encode antigen(s) of interest are delivered to immune cells that home to desired locations. For example, delivery of a cancer antigen encoding saRNA to T cells (or B cells, monocytes, DCs, or macrophages) and injection of those cells into the patient, results in rapid production of the antigen in the T cells and eventual death of these T cells due to rapid saRNA replication. These bursts of dying T cells loaded with target antigen simulate an infection and result in uptake of material by innate cells in the target tissues and prime a vaccine response against the target antigen. Depending on the target tissue, presence of adjuvants, and overall inflammatory state of the patient, this strategy is used to induce tolerance as well. To induce tolerance, the aforementioned kamikaze cells are engineered to release tolerogenic factors and antigen or are contacted with tolerogenic factors such as TGF-beta and IL-10. For example, a kamikaze T or B cell may be loaded with an mRNA, DNA or saRNA that overexpresses a desired antigen while also expressing factors that are tolerogenic (e.g., secretion of TGF-beta and IL-10). These cells will then migrate to the lymphoid organs before undergoing death, which will release the antigens and the tolerogenic factors to the environment and help induce tolerance against the target antigen. This would help eliminate auto-reactive effector T cells and spur production of T regs capable of protecting against autoreactivity. In one non-limiting example, this approach is employed using a rheumatoid arthritis antigen.

Alternative to Protein Delivery saRNAs, mRNAs or expression vectors, e.g., plasmids, provide continual protein production for the duration of vaccine treatment vs. a pulse of protein delivery Continual Modulation of Cell Function Using T cell adoptive transfer therapies as an example, development of better T cell therapies is accomplished by using saRNA that encode inhibitors of immunosuppression pathways. saRNA is also used to express stimulatory proteins to maintain high states of T cell activation and/or anti-apoptotic proteins to prolong survival. Non-limiting examples of suppression inhibitors include any materials that block PD-1, PD-L1, CTLA-4 or other checkpoint inhibitors. Be expressing IL-2, NF-Kb, IL-7, IL-15, IL-12, etc. high T cell activity can be maintained and proteins like Bcl2 and Bclx1 can help prolong survival.

Reprogramming of Immune Cell Function

Immune cells are used as a source of autologous cells. The cells are reprogrammed to perform numerous disease treating functions. For example, in the case of arthritis, materials are delivered to a T cell to induce its expression of a joint homing pheonotype and program the release of factors (such as IL-4, IL-6, IL-10, IL-13, IL-11, TGFb, retinoic acid, and checkpoint stimulants) that can alleviate symptoms or in the case of Parkinson's disease, materials to a T cell or B cell to induce its expression of brain-horning receptors and secretion of factors to improve patient outcomes. With respect to arthritis, removing pro-inflammatory cytokines is also useful, e.g., a T cell with high affinity for IL-2 would soak up cytokine that the auto-reactive effector cells require.

The following materials and methods were used to generate the data described herein.

CellSqueeze Microfluidic Devices

The CellSqueeze platform consists of three major components: a) a silicon and glass microfluidic chip that contains multiple channels in parallel, each containing at least one constriction point b) a reservoir system that interfaces with the chip and allows one to load/collect the cell suspension c) a pressure regulation system to pressurize the reservoirs and facilitate fluid flow through the chip. In a typical workflow (FIG. 1A), the target delivery material is mixed with the desired cells (in suspension) and load them into the reservoir. Then pressure tubing is connected to the reservoir and the chamber is pressurized at the desired level to initiate fluid flow. After treatment, the cells may be collected from the output reservoir and incubated at the desired temperature for a period of time, e.g., at least 1, 2, 3, 4, 5 min. or more, to ensure proper membrane recovery before further processing.

CellSqueeze devices and the associated operating equipment were obtained from SQZ Biotechnologies, USA. Devices were assembled and used in accordance with manufacturer protocols. Sharei, A., N. Cho, S. Mao, E. Jackson, R. Poceviciute, A. Adamo, J. Zoldan, R. Langer, and K. F. Jensen. 2013. Cell squeezing as a robust, microfluidic intracellular delivery platform. Journal of visualized experiments: JoVE: e50980.

For example, individual CellSqueeze devices and the associated reservoir systems were kept in 70% ethanol to maintain sterility. For each experiment, the desired CellSqueeze device was connected to the reservoirs and 70 ul of PBS was used to flush the system prior to use with cell samples.

During a delivery experiment, the target cells, device+reservoir, and collection plate are kept on ice (T cells and B cells) or at room temperature (dendritic cells). Cells (at a concentration of $2\times10^6$-$1\times10^7$ cells/ml in PBS or culture media) are mixed with the target delivery material at the desired concentration prior to being added to the fluid reservoir. The pressure tubing is connected, system is set at the desired operating pressure, and the flow is initiated by pressurizing the reservoir containing the sample. After passing through the chip, cells are collected from the collection reservoir and transferred to a 96-well plate. This process is optionally repeated. To minimize clogging, the direction of flow in the chip is alternated between samples. Samples are allowed to incubate on ice for 5 min post-treatment before media is added and they are transferred for further processing.

CAR T Cells

By modifying T cells to express a chimeric antigen receptor (CAR) that recognizes cancer-specific antigens, one can prime the cells to recognize and kill tumor cells that would otherwise escape immune detection. The process involves extracting a patient's T cells, transfecting them with a gene for a CAR, then reinfusing the transfected cells into the patient.

These artificial T cell receptors (also known as chimeric T cell receptors, chimeric immunoreceptors, or CARs) are engineered receptors, which graft an arbitrary specificity onto an immune effector cell. Typically, these receptors are used to graft the specificity of a monoclonal antibody onto a T cell. Prior to the invention, transfer of nucleic acid coding sequence was typically facilitated by retroviral vectors. The methods described herein do not utilize or encompass viral vectors. The coding sequence or protein CAR is delivered to the cytosol of an immune cell such as a T cell using cell squeezing with the described device without the need for a viral vector.

For therapeutic applications, a patient's T cells are obtained (and optionally enriched or purified) from peripheral blood and modified to express an artificial (chimeric) receptor specific for a particular cancer-associated antigen. After the modification, the T cells recognize and kill cancer. For example, an exemplary CAR recognizes CD19, an antigen expressed in B-cell¬blood malignancies. After the T cells have been modified to express the CAR, the modified T cells are reinfused into the patient. The engineered cells recognize and kill cancerous cells. Such therapy has been used for ALL, non-Hodgkin's lymphoma, and chronic lymphocytic leukemia (CLL), and is appropriate for therapy for any type of cancer, including blood-born cancers such as leukemias, B-cell malignancies (e.g., acute lymphoblastic leukemia (ALL) and chronic lymphocytic leukemia), as well as solid cancers. The cell processing methods described herein represent a superior process for generating CAR T cells.

The autologous T cells express CAR proteins that confer upon the engineered T cells the ability to recognize a specific antigen on tumor cells. Such tumor-associated antigens have been identified and are known in the art (see tables below). The engineered CAR T cells are then expanded in the laboratory, and the expanded population of CAR T cells is then infused into the patient. The T cells multiply in the patient's body and, recognize, bind to, and kill cancer cells that bear the tumor-associated antigen on their surfaces. Optionally, immune checkpoint inhibitors such as programmed death-1 (PD-1) inhibitors or inhibitors of the ligand (PD-L1) and/or anti-cytotoxic T-lymphocyte antigen 4 anti-CTLA4 drugs may be combined with CAR T cells.

Treatment of Tumors

Immune cells treated as described above to introduce compounds or compositions into the cytosol are used to treat tumors, e.g., by eliciting a tumor-specific T-cell mediated immune response to kill or inhibit the proliferation of a tumor. The method is applicable to any tumor type, because the devices and methods introduce into the immune cells tumor-specific/tumor associated antigens or mixtures thereof, e.g., tumor biopsy cell lysate preparations. For example, tumor types include bladder cancer, breast cancer, colon and rectal cancer, endometrial cancer, kidney cancer, leukemia, lung cancer, melanoma, non-Hodgkin lymphoma, pancreatic cancer, prostate cancer, thyroid cancer, which are prevalent in the U.S. population. (American Cancer Society: Cancer Facts and Figures, 2015, Atlanta, Ga.: American Cancer Society, 2015. Available online.) Other tumor types to be treated using the processed immune cells include brain (glioblastoma), liver (hepatocellular carcinoma) as well as metastatic cancers that occur in anatomic sites or tissues in the body distinct from the site or tissue of a primary tumor.

In preferred embodiments, the tumor is a pancreatic cancer, ovarian cancer, melanoma, lung cancer, glioma or glioblastoma tumor. In some embodiments, the tumor of a specific patient is targeted. For example, tumor lysate from a patient may be used as antigens to be delivered to immune cells using cell squeezing.

Tumor Cell Antigens

Purified tumor-associated antigens or tumor cell lysates (heterogenous mixture of antigens) are used as antigens to be delivered to immune cells using cell squeezing. Tumor cell lysates are produced from tumor cell lines or tumor biopsy tissue obtained from the subject, who has been diagnosed with a tumor and/or is slated for treatment for a pathological malignancy. Production of tumor cell lysates is known in the art. Such tumor lysate preparations are suitable for use in cell squeeze-based delivery to the cytosol of immune cells For example, tumor tissue is resected from a subject, and the tissue minced. Tumor cells are processed, e.g., fractionated, enriched or purified/isolated. In the case of non-solid tumor, blood-borne tumor (primary or metastatic), or cell line, cells enriched), cells are obtained from a bodily fluid, e.g., peripheral blood, and optionally enriched or purified to concentrate tumor cells from non-tumor cells. Tumor cells (or populations of cells enriched for tumor cells) are processed to obtain a tumor cell lysate (e.g., as described by Hatfield et al., J Immunother. 2008 September; 31(7): 620-632.) For example, the cells are subjected to a freeze-thaw cycle (e.g., 1, 2, 3, 4, 5, 10 or more cycles of freeze/thaw). Optionally, steps include removal of solid debris and filtering, e.g., 0.2 micron filter, to obtain a mixture of patient-specific tumor cell antigens.

In a non-limiting example, the cells are lysed through multiple (for example 4) consecutive freeze/thaw cycles using liquid nitrogen. The cells are then sonicated for about 10, 15, or 20 seconds before centrifuging at 1000 g to remove insoluble debris. The supernatant is then used for lysate delivery. Optionally, lipids and/or nucleic acids are removed from the lysate prior to delivery to immune cells. Adjuvants are optionally added prior to delivery to augment APC function.

In some embodiments, common endogenous proteins such as actin are removed so as to selectively increase the proportion of cancer antigens in the lysate. In some implementations, a mild surfactant is added to a lysed cell composition to help prevent proteins from forming aggregates that may be difficult to deliver or process for presentation by a cell.

Autologous tumor cell lysate may also be generated using commercially available devices/methods, e.g., gentleMACS™ Dissociator (Miltenyi Biotec GmbH).

Tumor-associated antigens are known in the art and such antigens can be biochemically purified, recombinantly expressed, and/or otherwise purified/isolated. Examples of such antigens are shown in the tables below.

|  |  | Type of tumor | Normal tissue distribution |
|---|---|---|---|
| Shared Antigens |  |  |  |
| Cancer-testis (CT) Ags | BAGE GAGE MAGE NY-ESO-1 SSX | melanoma, lymphoma, lung, bladder, colon and breast carcinomas | spermatocytes/ spermatogonia of testis, placenta, ovary cells |
| Differentiation Ags | Gp100 Melan-A/ Mart-1 Tyrosinase PSA CEA Mammaglobin-A | melanoma, prostate cancer, colon and breast carcinomas | melanocytes, epithelial tissues, prostate, colon |
| Overexpressed Ags | p53 HER-2/neu livin survivin | esophagus, liver, pancreas, colon, breast, ovary, bladder and prostate carcinomas | ubiquitous (low level) |
| Unique Antigens |  |  |  |
| Unique Ags | β-catenin-m β-Actin/4/m Myosin/m HSP70-2/m HLA-A2-R170J | melanoma, non-small cell lung cancer, renal cancer | N/A |
| Unique/Shared Antigens |  |  |  |
| Tumor-associated Carbohydrate Ags | GM2 GD3 MUC-1 sTn globo-H | melanoma, neuroblastoma, colorectal, lung, breast, ovarian and prostate cancer | epithelial tissues (e.g., renal, intestinal, colorectal) |

| Tumor | Antigen |
|---|---|
| Acute Myelocytic Leukemia | WT1, PR1 |
| Breast | E75, p53; HER-2/neu |
| Colorectal | ras; CEA |
| Liver | AFP; CEA |
| Lung | URLC10; ras; HER-2; VEGFR1 and 2; mutant p53 |
| Melanoma | MAGE; gp100; MART-1; Tyrosinase; NY-ESO-1 |
| Ovarian | P53; NY-ESO-1; HER-2 |
| Uterine | HPV16 E7; Survivin; mutant p53 |
| Pancreas | ras; VEGFR1 and 2; MUC-1; Survivin |

(Buonaguro et al., Clin Vaccine Immunol. 2011 January; 18(1): 23-34.)

Other purified tumor antigens are known in the art, e.g., described in Tumor-Associated Antigens. Edited by Olivier Gires and Barbara Seliger, 2009, WILEY-VCH Verlag GmbH & Co., KGaA, Weinheim.

Viral Antigens

Virus-associated antigens may be delivered to immune cells using cell squeezing. Virus-associated antigens are known in the art and such antigens can be biochemically purified, recombinantly expressed, and/or otherwise purified/isolated. Examples of viral antigens are shown in the table below.

| Virus | Antigen |
|---|---|
| Human Immunodeficiency Virus (HIV) | Viral capsid p24 protein; Group-Specific Antigens |
| Human Papillomavirus (HPV) | L1 capsid protein; E6; E7 |
| Epstein-Barr Virus (EBV) | Viral Capsid Antigen (VGA); Early Antigen (EA); Nuclear Antigen (EBNA) |
| Ebola Virus | Nucleoprotein (NP); Viral Proteins VP40; Viral Protein VP24; Protein VP30; Protein VP35; glycoprotein (GP) |
| Influenza Viruses | Hemagglutinin (HA) proteins, such as any of H1 to H18; neuraminidase (NA) proteins |
| Measles Virus | Haemolysin; Haemagglutinin |
| Hepatitis C (HCV) | Core Antigen |
| Smallpox Virus | Intracellular mature virion (IMV) antigen A27L; Intracellular mature virion (IMV) antigen L1R; Extracellular enveloped virion (EEV) antigen A33R; Extracellular enveloped virion (EEV) antigen B5R |
| Herpes Simplex Virus (HSV) | Glycoprotein G-1; Glycoprotein G-2; Glycoprotein E; Glycoprotein D; Glycoprotein I; Glycoprotein B; VHS; VP7; VP16; VP21; VP23; VP24; VPAP; DNB; VP11/12; VP22a; RIR1 |
| Severe Acute Respiratory Syndrome (SARS) Associated Coronavirus | M protein; E Protein; S Protein; Nucleocapsid Protein |
| Poliovirus | VP1; VP2; and VP3 |

Bacterial Antigens

Bacterial antigens may also be delivered to immune cells using cell squeezing. In preferred embodiments, the bacterial antigens are associated with intracellular bacteria such as a *Mycoplasma* sp., *Mycobacterium* sp. (e.g., *M. tuberculosis*) or *Listeria monocytogenes*.

The following materials and methods were used to generate the data described herein.

Mouse Immune Cell Isolations

T and B cells were isolated from the spleens of wild-type C57BL6/J mice using known methods, e.g., cell-specific isolation kits from Stemcell Technologies (Vancouver, Canada) based on manufacturer's instructions (negative selection technique). Monocytes/macrophages were isolated from the peritoneal cavity of wild-type C57BL6/J mice 3 days following intraperitoneal injection of 1 ml of thioglycollate solution. Cells were purified using CD11 b positive selection kit from Stemcell Technologies (Vancouver, Canada) based on manufacturer's instructions. Cells were cultured in glutamine containing RPMI 1640 media containing 10% fetal bovine serum, 1% antibiotics/antimycotic, 0.5% beta-mercaptoethanol, 1% non-essential amino-acids, 1 mM sodium pyruvate, and 10 mM HEPES buffer (all from (Life Technologies, NY, USA)).

Human Primary T Cells and Monocyte Derived Dendritic Cells

Human PBMCs were separated using known methods, e.g., Ficoll-Paque (GE Healthcare, Uppsala, Sweden) density gradient centrifugation from whole blood. CD4+ T cells were separated from the CD14-negative fraction of PBMCs using CD14 and CD4 magnetic microbeads (MACS Miltenyi Biotec, Auburn, Calif.). T cells were cultured in RPMI 1640 media (Cellgro, Manassas, Va.) containing 10% Human Serum (AB) (GemCell, West Sacramento, Calif.), 100 U/ml penicillin and streptomycin sulfate 100 μg/ml (H 10 medium) supplemented with 5 ng/ml rhIL-15 (R&D Systems, Minneapolis, Minn.) to maintain cell viability without cell activation. Human Monocyte derived Dendritic Cells (MDDCs) were prepared from CD14-positive monocytes selected from peripheral blood mononuclear cells using anti-CD14 magnetic microbeads (MACS Miltenyi Biotec) and cultured for 6 days with 100 ng/ml interleukin-4 and 50 ng/ml granulocyte-macrophage colony-stimulating factor (R & D Systems).

Cell Transfection

Human CD45 siRNA:
sense
(SEQ ID NO: 1)
5'-AF488 CUGGCUGAAUUUCAGAGCAdTdT-3',

Human CD4 siRNA:
sense
(SEQ ID NO: 2)
5'-GAUCAAGAGACUCCUCAGUdTdT-3'
(Alnylam, Cambridge, MA);

vif siRNA:
sense
(SEQ ID NO: 3)
5'-CAGAUGGCAGGUGAUGAUUGT-3', gag siRNA:
sense
(SEQ ID NO: 4)
5'-GAUUGUACUGAGAGACAGGCU-3' (Huang et al., 2013, Nature Biotechnology 31: 350-356);
(GenePharma, Shanghai, China);

control scrambled siRNA:
(SEQ ID NO: 5)
5'-GCCAAGCACCGAAGUAAAUUU-3',

Human DC-SIGN siRNA:
sense
(SEQ ID NO: 6)
5'-GGAACUGGCACGACUCCAUUU-3'
(Dharmacon, ThermoScientific, Pittsburgh, PA).

Nucleofection

In the described electroporation experiments, Amaxa Nucleofector II (Lonza Inc., Allendale, N.J.) was used according to the manufacturer's recommendations. Human T cell experiments were conducted using the program for human unstimulated T cells, high viability, U-014 with a human T cell kit. For human MDDCs we used the program for human dendritic cells U-002 with a human dendritic cells kit for MDDCs. Briefly 2×10$^6$ cells were suspended in 100 μl of Nucleofection solution with 200 pmol of siRNA and nucleofected by the machine. To test protein delivery, we used an APC-labeled mouse IgG1 (cl. MOPC-21, Biolegend) at 0.02 mg/ml for both CellSqueeze and nucleofection experiments. We also used 3 kDa Cascade Blue labeled dextran and 70 kD Fluorescein labeled dextran at 0.2 mg/ml (Invitrogen).

Regulatory T Cells

Regulatory T cells (Tregs) were isolated and expanded using known methods. For example, CD4+ T Cell-enriched PBMC were isolated from peripheral blood of healthy individuals by density centrifugation using the CD4+ T cells RosetteSep enrichment kit (Sigma-Aldrich and STEMCELL Technologies) and labeled with anti-CD3-PE-Cy7, CD4-FITC, CD25-APC and CD127-PE. CD3+CD4+CD25+CD127low Tregs were sorted on a FACS Aria cell sorter (BD Biosciences), stimulated with anti-CD3/anti-CD28-coated microbeads (Invitrogen) and cultured with IL-2 (300 U/ml).

For siRNA delivery, at day 7 of culture, Tregs were washed and resuspended at 1.0×10^7 cells/ml in X-VIVO 15 (Lonza) media alone. 1.0×10$^6$ cells were used per condition. CD4 siRNA (5'-GAUCAAGAGACUCCUCAGU-3' (SEQ ID NO: 7), Alnylam) and control siRNA (siGENOME Non-Targeting siRNA Pool #1, Thermo Fisher) were used at liAM with 30-4 chips design at 100 psi.

2 days after siRNA delivery, cells were stained with LIVE/DEAD® Fixable Violet Dead Cell Stain Kit (Life Technologies) and anti-CD4-APC. Data were acquired on a LSR2 flow cytometer (BD Biosciences) and analyzed on FlowJo (Treestar).

Flow Cytometry

Mouse cells were stained with the following antibodies: anti-CD8-Pacific Blue, anti-CD4-APC, anti-CD11b-PE (cl. M1/70), anti-CD11c-APC. Propidium iodide was used to exclude dead cells. Data was acquired using a FACS CantoII, LSR II, or LSRFortessa (BD Biosciences) and analyzed using FlowJo (Tree Star, Ashland, Oreg.).

Human cells were stained with the following antibodies: anti-CD3-APC (cl.OKT3), anti-CD45RA-PE-Cy7 (cl. HI100) and anti-CD4-AF488 (cl.OKT4) from Biolegend (San Diego, Calif.) and an anti-DC-SIGN-APC (cl.9E9A8) (R & D Systems, Minneapolis, Minn.). Dead cells were excluded using Sytox blue and 7-AAD (7-Aminoactinomycin D) dead stain dye (Invitrogen). Data were acquired using a FACS CantoII (BD Biosciences) and analyzed using FlowJo (Tree Star, Ashland, Oreg.).

HIV Infection and Intracellular p24 Antigen Staining

Primary CD4+ T cells were treated with 5 μM siRNA using a 10-4 chip. For knockdown of CD4, siRNA was delivered 48 hrs prior to infection while siRNA targeting viral genes vif and gag were delivered 24 hrs prior to infection. The cells were then stimulated overnight with 5 pg/ml Phytohaemagglutinin (PHA) and infected with HIV-IIIB in 96 well plates at 2×10$^5$ cells/well with HIV IIIB (400 ng/mi p24). HIV IIIB was obtained from the N1H AIDS Reagent Program and viral stock was prepared as previously described (18). The infection was enhanced by the addition of polybrene at 5 μg/ml and spinoculation at 1200×g, for 2 hrs at 37° C. (19). Intracellular p24 antigen staining was performed 24 hrs later using an anti-p24 KC57-FITC Antibody (Beckman Coulter, Fullerton, Calif.) with Fix & Penn Kit for Cell penneabilization (Invitrogen) and analyzed by flow cytometry.

Quantitative RT-PCR

Total RNA was isolated from T cells using RNeasy Mini Kit (Qiagen) and copy DNA was synthesized using Superscript III and random hexamers (Invitrogen). Real Time PCR was performed using SsoFast EvaGreen Supemix and a Bio-Rad CFX96 Real-Time PCR System (Bio-Rad Laboratories, Hercules, Calif.). The primers were as follows: Gapdh forward: 5'-AGCCACATCGCTCAGACAC-3' (SEQ ID NO: 8), Gapdh reverse: 5'-GCCCAATACGAC-CAAATCC-3' (SEQ ID NO: 9), CD4 forward: 5'-GGCAGTGTCTGCTGAGTGAC-3' (SEQ ID NO: 10), CD4 reverse: 5'-GACCATGTGGGCAGAACCT-3' (SEQ ID NO: 11).

Statistical Analysis

One-way analysis of variance (ANOVA) with Bonferroni's Multiple comparison test was performed when comparing multiple groups, or two-tailed Student's T test was performed when comparing 2 groups using GraphPad Prism 4 software (GraphPad Software, San Diego, Calif.). *,  and * indicate P values below 0.05, 0.01 and 0.001 when using Bonferroni's Multiple comparison test, and ### indicate P values below 0.001 when using two-tailed Student's T test. Data are represented as mean±1 standard deviation unless otherwise indicated.

Delivery by Mechanical Membrane Disruption

The microfluidic devices tested contained 45-75 parallel microfluidic channels of varying constriction lengths (10-50 μm), widths (4-9 μm) and number of constrictions per channel (1-5 constrictions). (Sharei et al., 2013, Proceedings of the National Academy of Sciences of the United States of America 110: 2082-2087; Sharei et al., 2014, Integrative biology: quantitative biosciences from nano to macro 6: 470-475).

The system required to operate the microfluidic chip included a mounting component that secures fluid reservoirs to the silicon and glass device, and a pressure regulation system that controls the gas pressure used to drive the fluid through the system. In some embodiments, the device comprises a syringe or pressure source to induce flow through a microfluidic channel.

The operating procedure is illustrated in FIG. 1A. As cells flow through the microfluidic channels (FIG. 1B), they reach a constriction point in the channel (about 50% less than the diameter of the majority of cells to be treated) which results in rapid mechanical deformation (exemplary dimensions of constriction point for target cells are as follows T cells (resting: 7-8 μm, activated (7-15 μm), macrophage (resting and activated: 10-30 μm), dendritic cells (resting and activated: 10-30 μm) of the cell, or squeezing. When the channel constriction is appropriately sized, the deformation transiently disrupts the cell membrane (e.g., the deformation process takes 0.1 μs-1 ms but the membrane disruptions can stay open for up to 5 min). Macromolecules present in the surrounding buffer then enter the cell cytosol if they are small enough to transit through the membrane disruptions. Within ~5 min, the membrane recovers its integrity and the macromolecules taken up by the cell remain trapped in the cell cytosol. Previous studies identified constriction length (L), width (W) and fluid speed (V, note that fluid speed is determined by operating pressure) as important parameters that influence delivery efficiency and cell viability. (Sharei et al., 2013, Proceedings of the National Academy of Sciences of the United States of America 110: 2082-2087).

A library of 16 different constriction designs were tested under different flow conditions. Library of tested device designs. The first number indicates constriction length, subsequent numbers preceded by a dash indicate the width of a constriction. If there are multiple identical constrictions in series it is indicated by an 'x' followed by the number of constrictions. For example, 10-5-4-5 contains 3 10 μm long constrictions in series with widths of 5 μm, 4 μm, and 5 μm. 10-4×5 contains 5 10 μm long constrictions in series, each with a 4 μm width.

| Tested Library of constriction designs | | | |
| --- | --- | --- | --- |
| 10-4 | 10-6-4-6 | 10-6 | 10-7x5 |
| 10-4x2 | 30-4 | 30-6 | 10-7 |
| 10-4x5 | 30-5-4-5 | 50-6 | 10-8 |
| 10-5-4-5 | 30-5x5 | 10-6x5 | 10-9 |

Each of the numbers in the width designation "5-4-5" (after the length designation "10") representing three different constriction points These variables included changes in pressure (to change the flow rate) and temperature to optimize macromolecule delivery and minimize cellular toxicity. All the buffers tested (PBS, PBS+2% serum, complete culture media, and whole human blood) were found to be compatible with the system, indicating that any physiologically compatible fluid or solution is suitable for suspending cells through the delivery device and process.

30-5×5, 10-4×2, 10-5-4-5, 10-6-4-6, 30-5-4-5, and 10-4×5 designs were also tested for murine and human T cells, but none was superior to the performance of 30-4.

TABLE 2

Delivery parameters and their influence on performance

| | |
|---|---|
| Constriction Design | Constriction geometry (specifically length and width) and number of constrictions in series affect delivery efficiency and cell viability. Longer, narrower, and more numerous constrictions typically result in more effective delivery but can lead to lower viability |
| Operating Pressure | The operating pressure of the system determines the speed at which cells move through the channels and are deformed. Higher speeds lead to more rapid deformation, which can result in higher delivery efficiency and potentially lower viability. |
| Flow Buffer | The buffer in which cells are suspended during treatment can affect cell health and may potentially interact with the biomolecule being delivered (e.g. serum proteins may bind certain materials). One known effect on delivery is mediated by calcium. The presence of calcium ions in the running buffer speeds up membrane repair post-treatment. Operating in calcium-free buffers can increase delivery at the risk of reducing viability. |
| Operating Temperature | Lower temperatures (i.e. on ice) improve delivery efficiency. Temperature could influence many parameters. One possibility is that low temperatures retard membrane repair post-treatment. |

In some embodiments, the device comprises a constriction length of about 5 μm to about 50 μm or any length or range of lengths therebetween. For example, the constriction length ranges from about 5 μm to about 40 μm, about 5 μm to about 30 μm, about 5 μm to about 20 μm, or about 5 μm to about 10 μm. In some embodiments, the constriction length ranges from about 10 μm to about 50 μm, about 20 μm to about 50 μm, about 30 μm to about 50 μm, or about 40 μm to about 50 μm. In some embodiments, the constriction depth ranges from about gum to about 200 um or any depth or range of depths therebetween. For example, the constriction depth ranges from about 2 μm to about 150 μm, about 2 μm to about 100 μm, about 2 μm to about 50 μm, about 2 μm to about 25 μm, about 2 μm to about 15 μm, or about 2 μm to about 10 μm. In some embodiments, the constriction depth ranges from about 10 μm to about 200 μm, about 25 μm to about 200 μm, about 50 μm to about 200 μm, about 100 μm to about 200 μm, or about 150 μm to about 200 μm. In some embodiments, the angle of the entrance or exit portion of the constriction ranges from about 0 degrees to about 90 degrees or any angle or range of angles therebetween. For example, the angle is about 5, about 10, about 15, about 20, about 30, about 40, about 50, about 60, about 70, about 80, or about 90 degrees or more. In some embodiments, the pressure ranges from about 50 psi to about 200 psi or any pressure or range of pressures therebetween. For example, the pressure ranges from about 50 psi to about 150 psi, about 50 psi to about 125 psi, about 50 psi to about 100 psi, or about 50 psi to about 75 psi. In some embodiments, the pressure ranges from about 75 psi to about 200 psi, about 100 psi to about 200 psi, about 125 psi to about 200 psi, about 150 psi to about 200 psi, or about 175 psi to about 200 psi. In some embodiments, the device comprises a constriction width of between about 2 μm and about 10 μm or any width or range of widths therebetween. For example, the constriction width can be any one of about 3 μm, about 4 μm, about 5 μm, about 6 μm, or about 7 μm.

Delivery to Primary Mouse Cells

Figure 2:
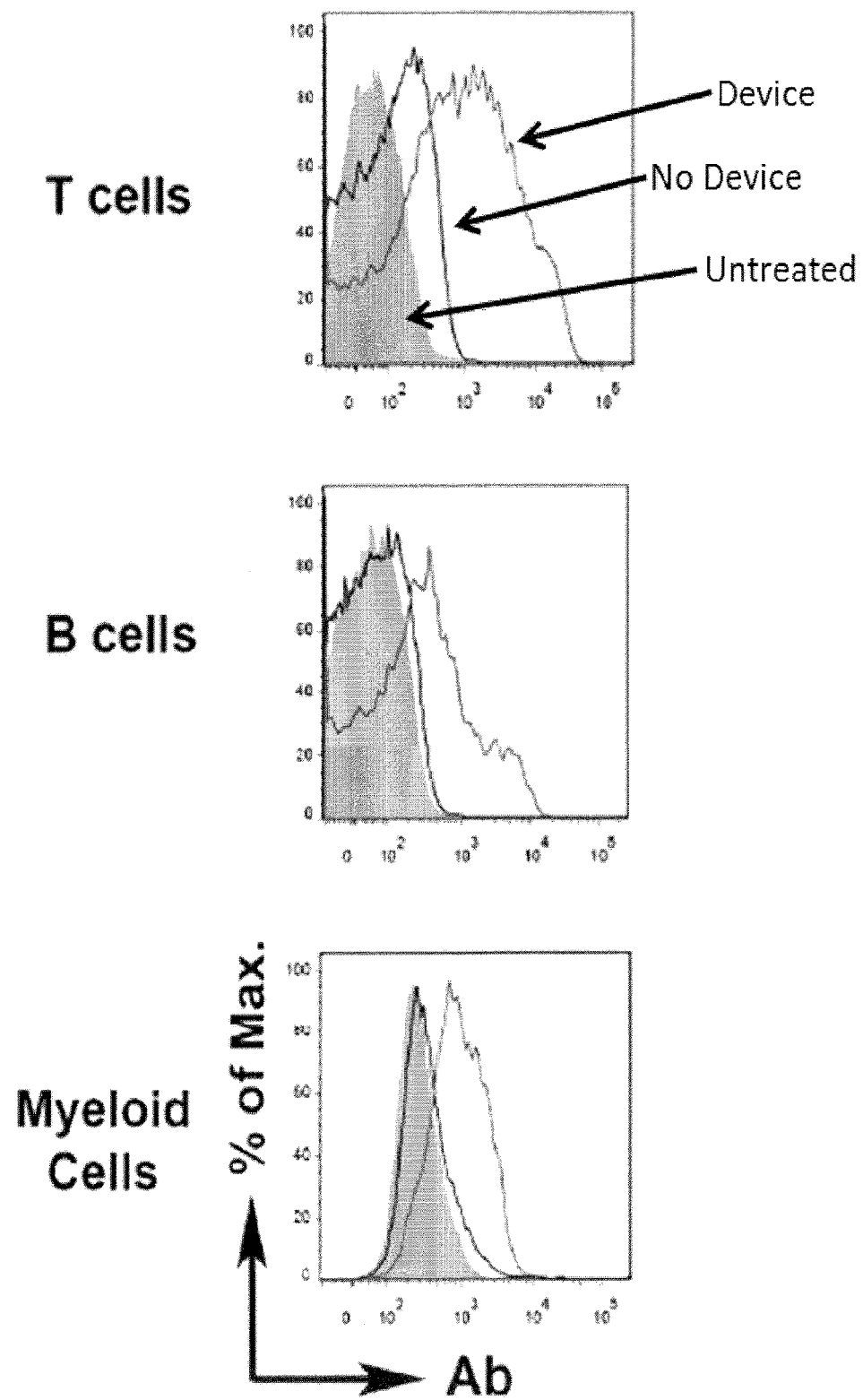
FIGS. 2A and B are a histogram and a bar graph showing dextran and antibody delivery to murine immune cells.
FIG. 2B shows delivery efficiency. All results were measured by flow cytometry within an hour of treatment. Dead cells were excluded by propidium iodide staining. Data in FIG. 2B (mean±SD) are from 3 independent experiments. Untreated cells were not put through the device or exposed to the biomolecules. The 'no device' samples were incubated with the biomolecules, but were not treated by the device. This control is meant to account for surface binding, endocytosis and other background effects.
Figure 2:
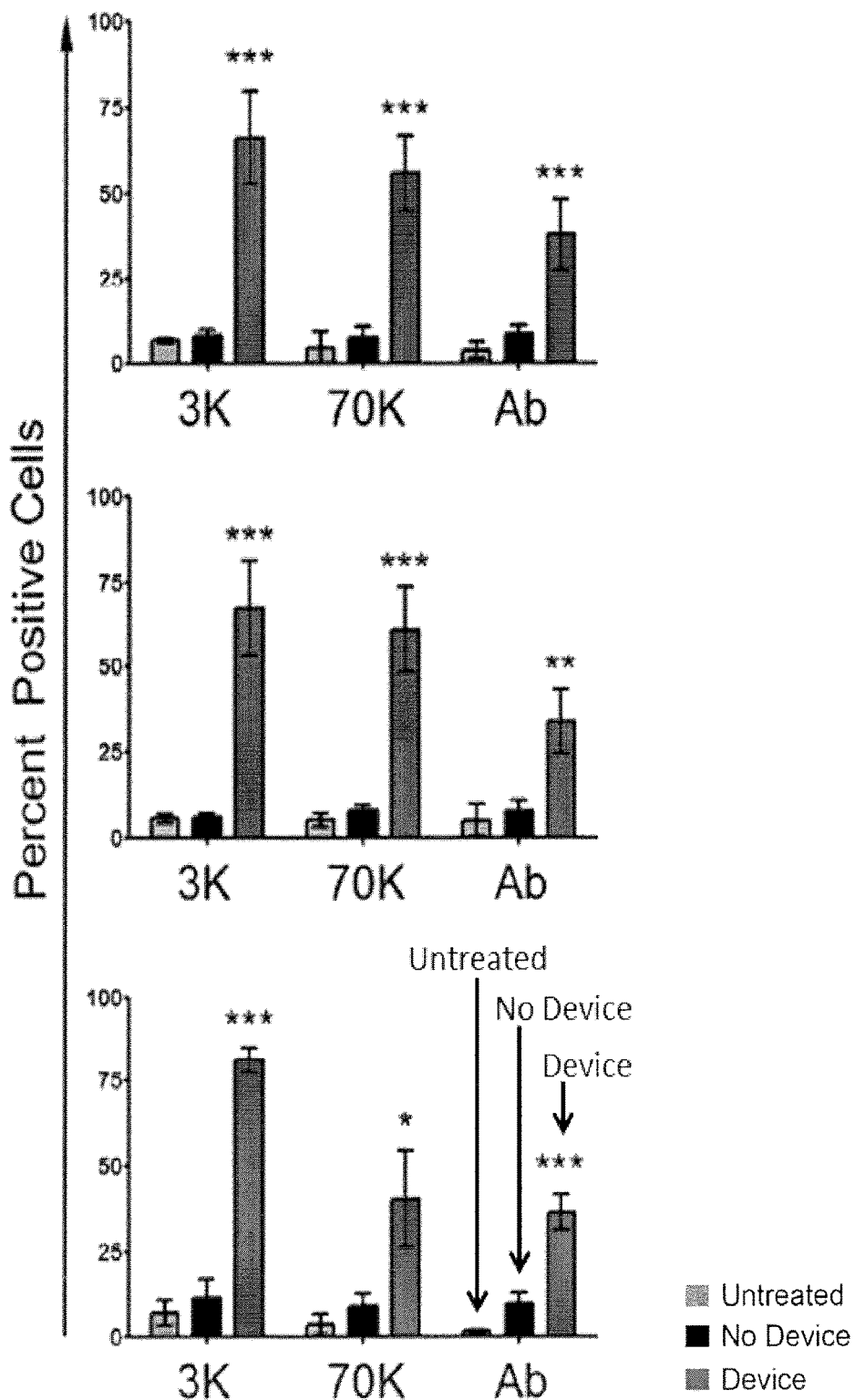

To assess the potential of this platform to enable intracellular delivery to primary immune cells, mouse T cells, B cells, and monocytes/macrophages were passed through microfluidic devices in the presence of fluorescently labeled dextran (3, and 70, and 2,000 kDa), and antibodies (about 150 kDa). These materials were selected as models for small molecules, polysaccharides, and proteins, respectively. At least four device designs and two operating pressures were tested per cell type. The initial selection of constriction dimensions was guided by work in cell lines, primary fibroblasts and embryonic stem cells. (Sharei et al., 2013, Proceedings of the National Academy of Sciences of the United States of America 110: 2082¬2087). Specifically, the widths of the constrictions were selected to be ~50% of the average diameter of the target cells. Delivery using the 30-4 design (i.e. constriction has a 30 μm length and 4 μm width) was the most effective for lymphocytes and myeloid cells (FIGS. 2A-C).

Figure 7:
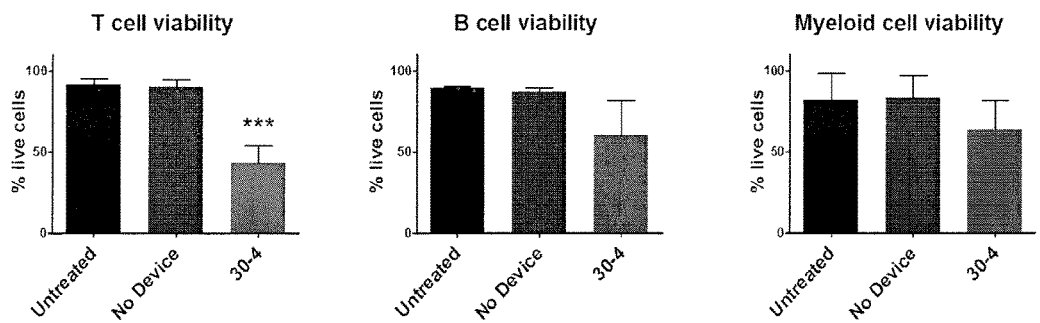
FIG. 7 is a series of bar graphs showing cell viability data corresponding to the experiments presented in FIG. 2. *** indicated p<0.001 when comparing viability of cells treated with 30-4 device to no device or untreated cases. Changes in viability of B cells and myeloid cells treated with the device were not significantly different from the untreated or no device cases.
Figure 8:
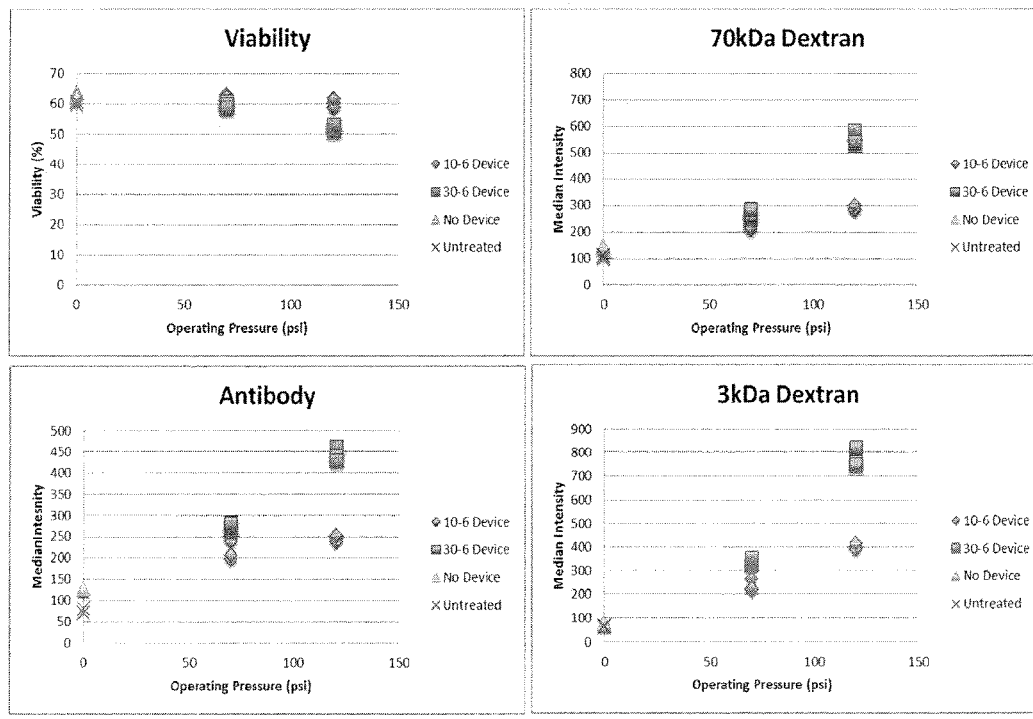
FIG. 8 is a series of graphs showing delivery of dextran and antibodies to bone marrow-derived dendritic cells (BMDCs). BMDCs were generated from C57BL6 mice by culturing bone marrow cells in GM-CSF containing media for 8 days. Cascade blue-labeled 3 kDa dextran, fluorescein-labeled 70 kDa dextran, and APC-labeled IgG1 were delivered using two device designs, 10-6 and 30-6.
Figure 9:
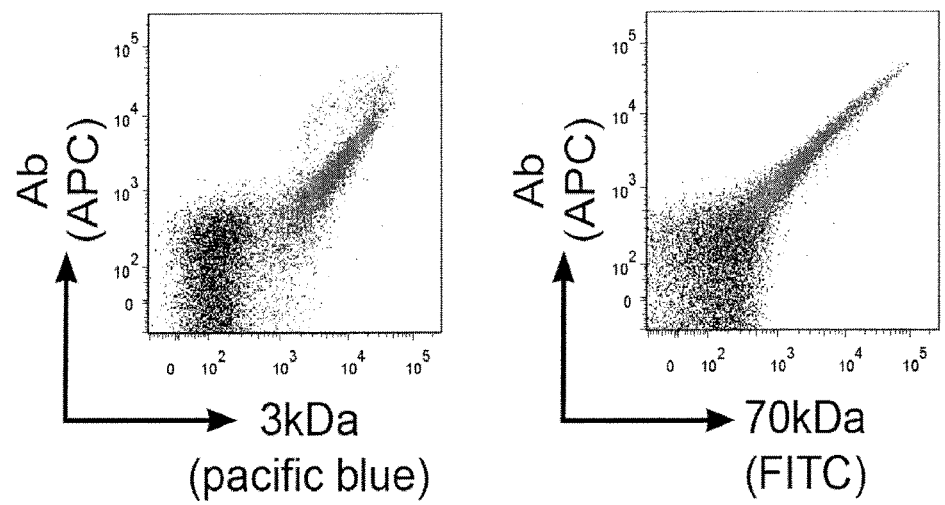
FIG. 9 is a graph showing correlation of antibody and dextran delivery. Dextran (3 kDa and 70 kDa) and antibody delivery to T cells using the 30-4 device (grey dots; center, upper right) compared to incubation with the material, i.e. no device (black dots; lower left).
Figure 10:
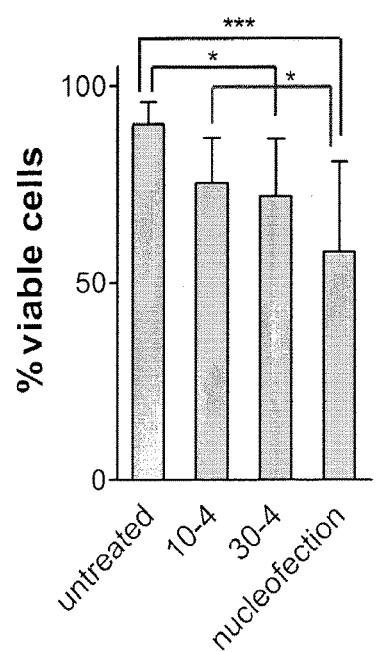
FIG. 10 is a bar graph showing viability of human CD4+ T cells. Cells that pass through the device have reduced viability when compared to untreated controls, but have better viability than cells that have undergone nucleofection. One-way ANOVA followed by Boneferroni's test was used to calculate statistical significance. * indicates p<0.05 and *** indicates p<0.001. Other groups of comparison did not show significantly different viability (i.e. 10-4 compared to untreated or 30-4, and 30-4 compared to nucleofection).
Figure 11:
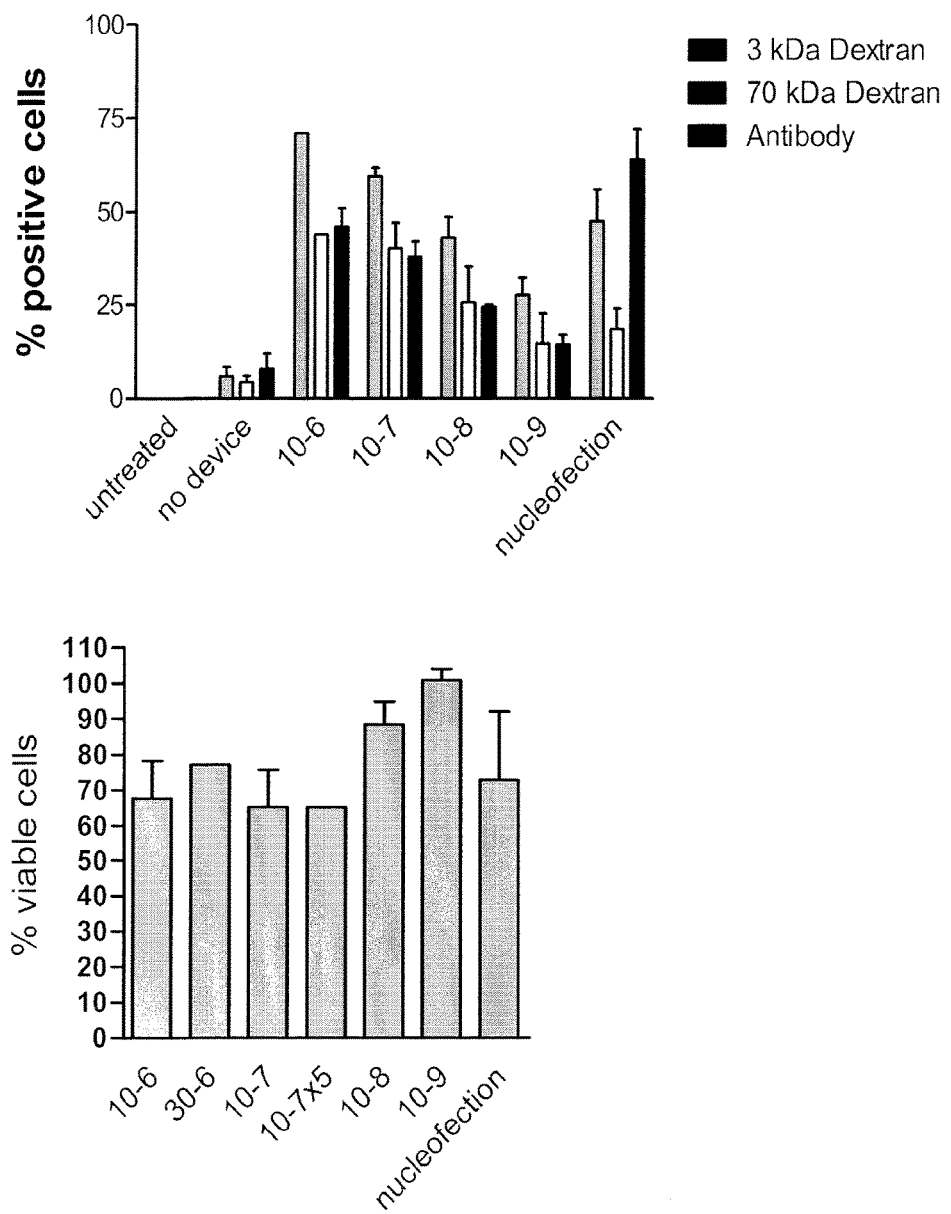
FIG. 11 is a series of bar graphs showing delivery (top) and viability (bottom) Results from testing different device designs for human MDDCs. Cascade blue labeled 3 kDa dextran, fluorescein labeled 70 kDa dextran, and APC labeled IgG1 isotype control antibodies were delivered using 6 different device designs and using Amaxa nucleofection. Viability and delivery results were measured immediately after treatment.

Delivery of biomolecules (FIGS. 2A-C and FIG. 6) and cell viability (FIG. 7) were measured by flow cytometry 1-2 hours post-treatment. FIGS. 2A-C shows representative histograms of antibody delivery (A), delivery efficiency of 3 kDa dextran, 70 kDa dextran, and antibodies in independent experiments (B), and representative median intensity data (C). Delivery efficiency (defined as the percentage of live cells with fluorescence above background) and median fluorescence intensity were used as the primary measures of delivery. 3 kDa dextran was delivered to 66.2±13.4%, 67.5±13.9%, and 80.8±3.46% of T cells, B cells, and myeloid cells, respectively. The uptake of the larger 70 kDa dextran and the Ab were less efficient than uptake of the 3 kDa dextran as expected, suggesting that smaller molecules are more efficiently delivered. Cell viability of T cells, but not B cells or myeloid cells, was somewhat impaired compared to untreated cells. Changes in viability of B cells and myeloid cells treated with the device were not significantly different from the untreated or no-device cells. Bone-marrow derived dendritic cells took up dextran and antibody, with limited loss of viability, using a larger constriction width of 6 μm because of their larger size (FIG. 8). Simultaneous delivery of dextran (3 kDa and 70 kDa) and antibody showed that the delivery of these molecules was proportional, i.e. cells that received antibody, also received a comparative amount of dextran molecules (FIG. 9).

Delivery to Human Immune Cells

Figure 3:
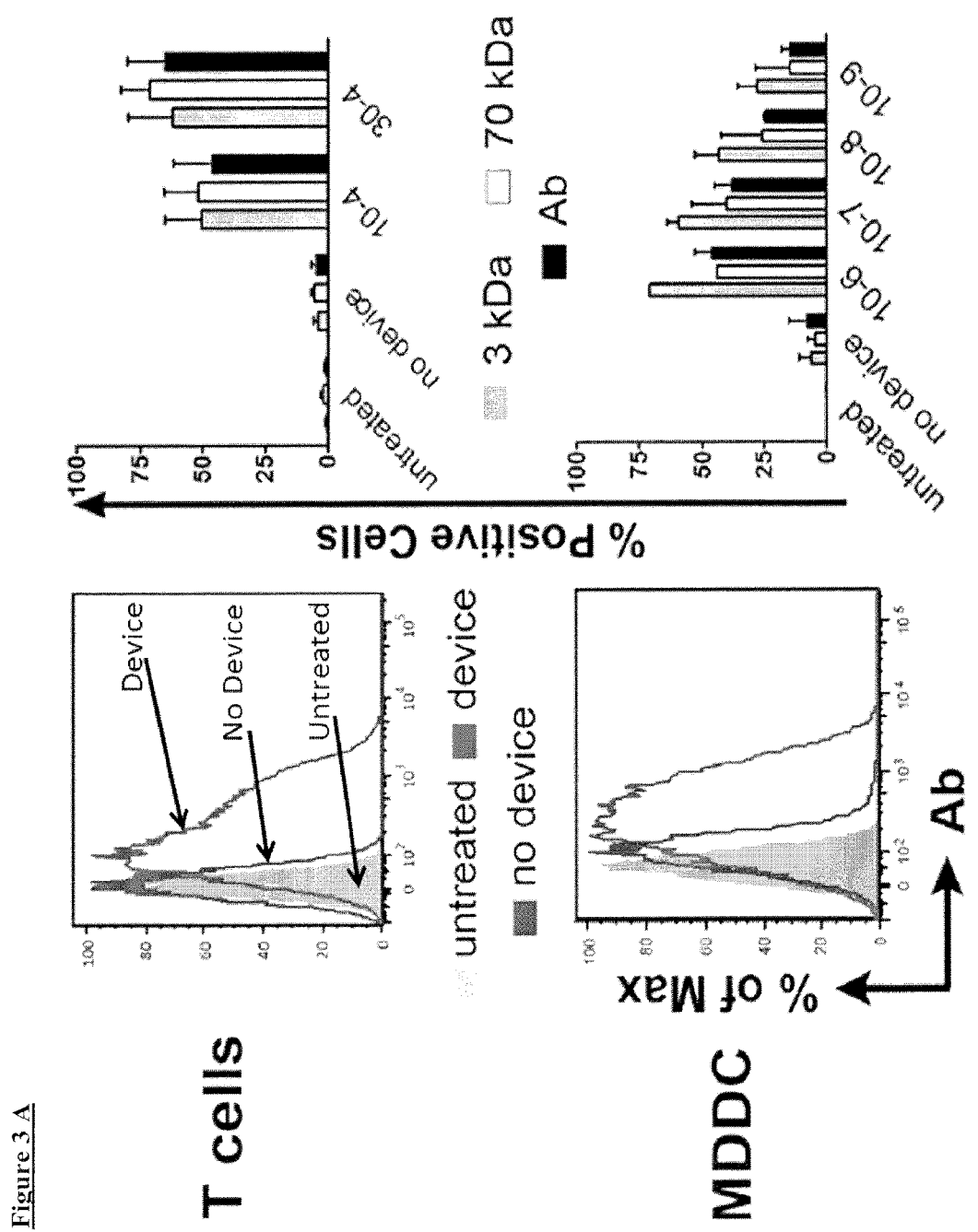
FIGS. 3A-D are graphs showing delivery of dextrans, antibodies and siRNA to human immune cells.
Figure 3:
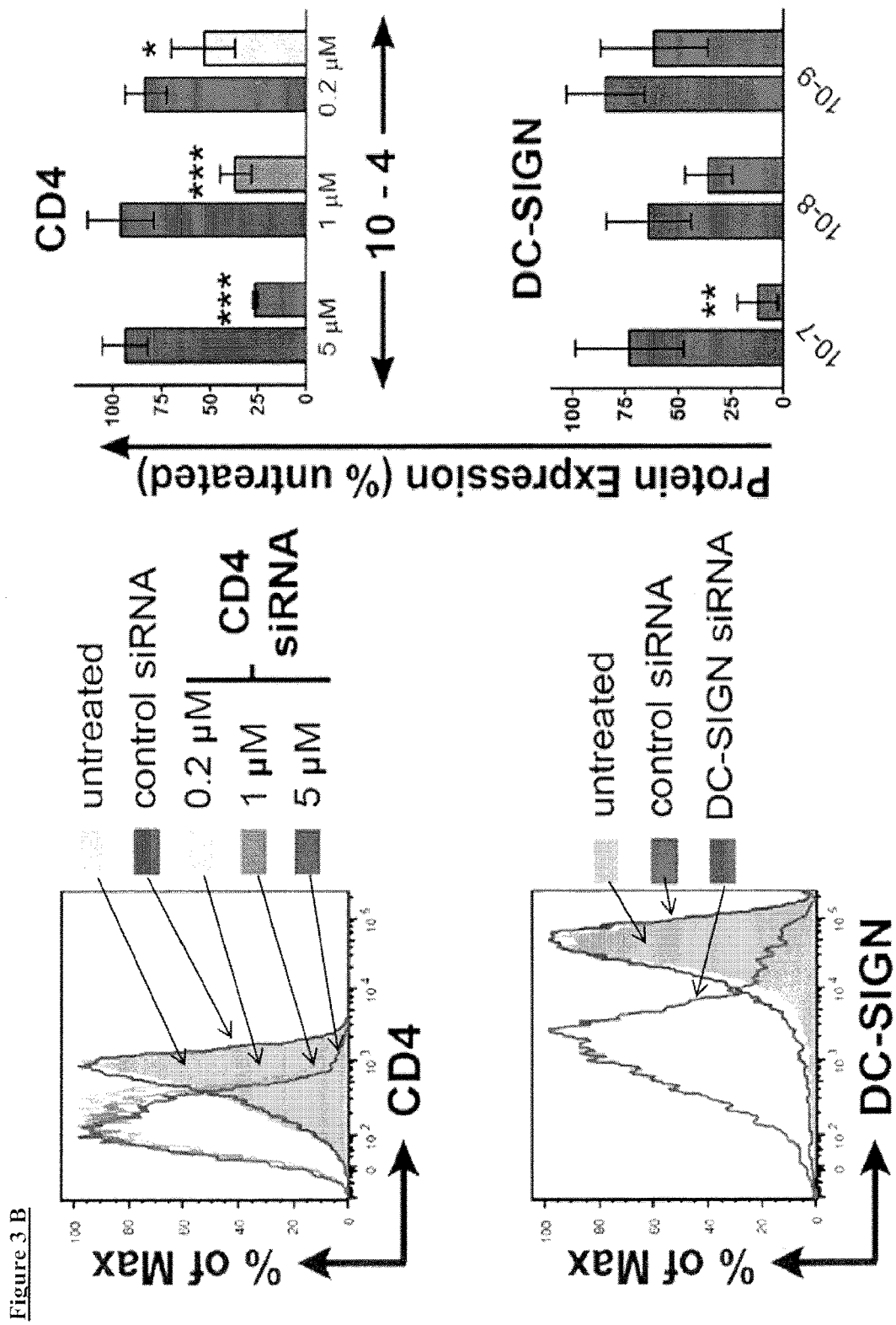
Figure 3:
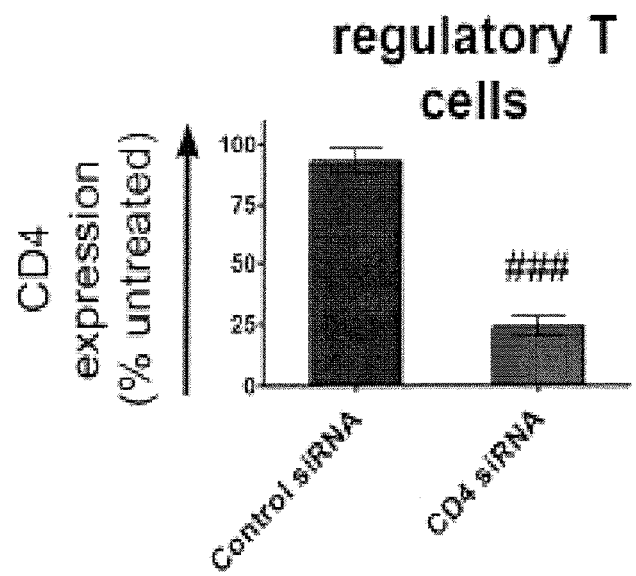
Figure 3:
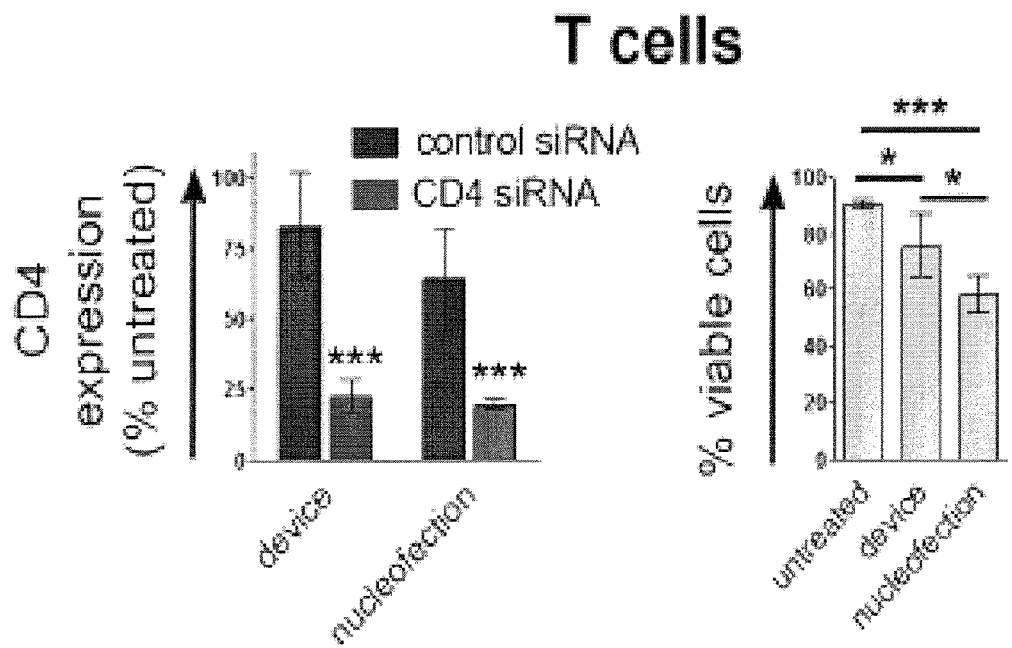

To examine the applicability of this approach to human immune cells, device designs with constriction widths ranging from 4-6 μm for T cells and 6-9 μm for monocyte-derived dendritic cells (MDDCs) were tested. Representative histograms of antibody delivery and efficiency data for different biomolecules are shown in FIG. 3A. The most effective designs delivered 3 kDa dextran to 70%±9% of T cells (4 μm constriction size) and 60%±4.5% of MDDCs (7 μm constriction size) (FIG. 3A). 70 kDa Dextran was delivered to 71%±11% of T cells and 40%±14% of MDDCs and protein (antibody) was delivered to 65%±15% of T cells and 38%±7% of MDDCs. Delivery of fluorescently labeled siRNA (CD45RA siRNA—Alexa-Fluor-488) yielded similar results (FIGS. 12, 13).

Figure 12:
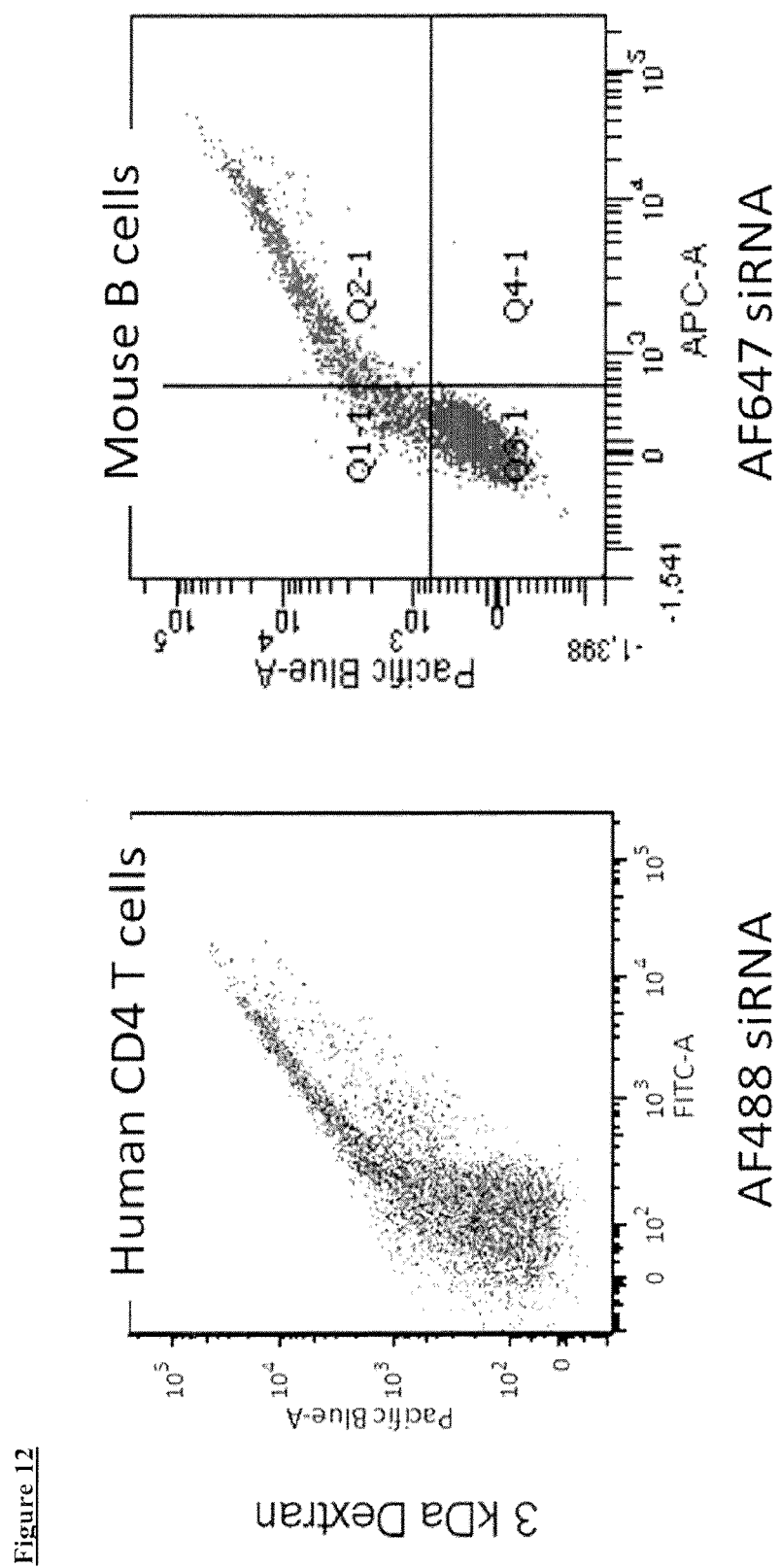
FIG. 12 is a series of graphs showing Alexa 488 or Alexa 647 labeled siRNA and 3 kDa cascade blue labeled dextran were delivered simultaneously to human CD4 T cells by a 10-4i device and murine B cells by a 30-5x5i device. The data indicate that delivery of the two materials correlates closely. This result is consistent with the proposed diffusive delivery mechanism, i.e. delivery efficacy is mostly dependent on material size rather than chemical structure.
Figure 13:
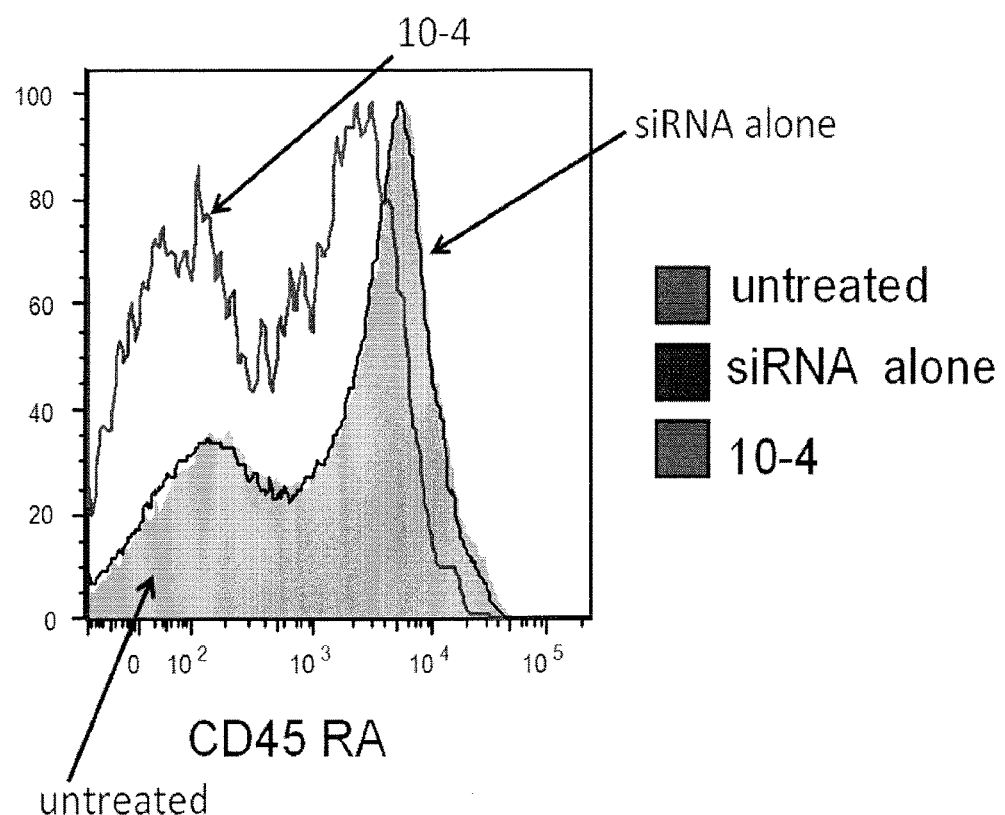
FIG. 13 is a graph showing CD45RA expression. siRNA against CD45RA was delivered to human T cells by a 10-4 device. Knockdown was measured by flow cytometry 72 hours post-treatment.
Figure 14:
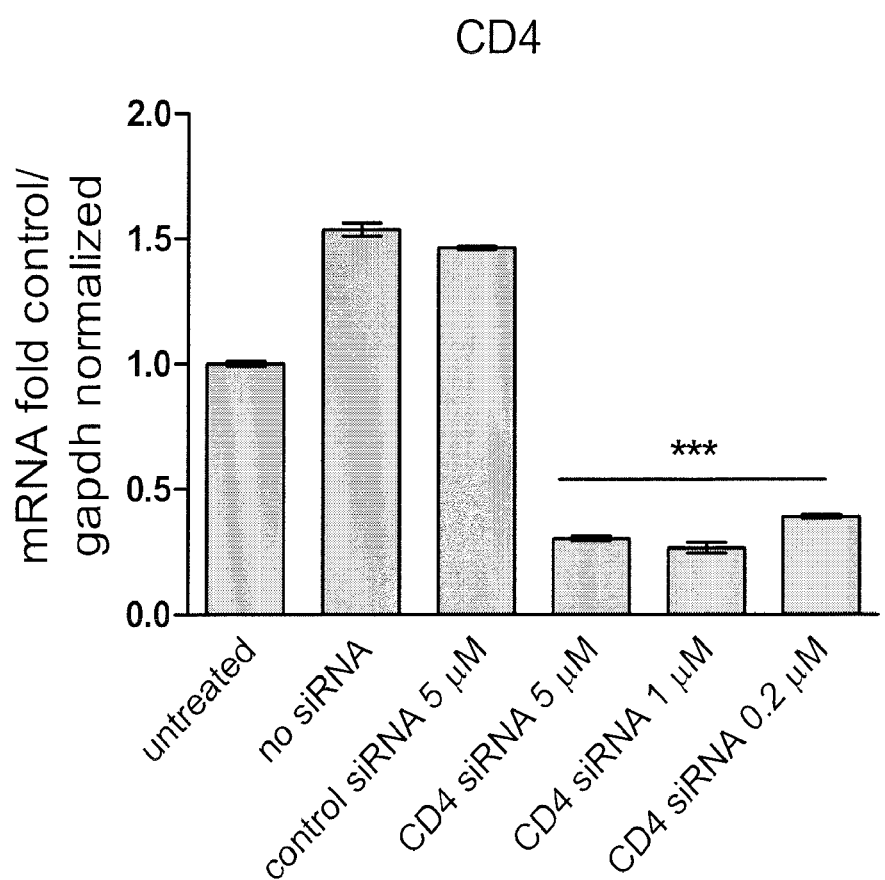
FIG. 14 is a bar graph showing CD4 mRNA knockdown (as measured by PCR 48 hours after delivery).
Figure 15:
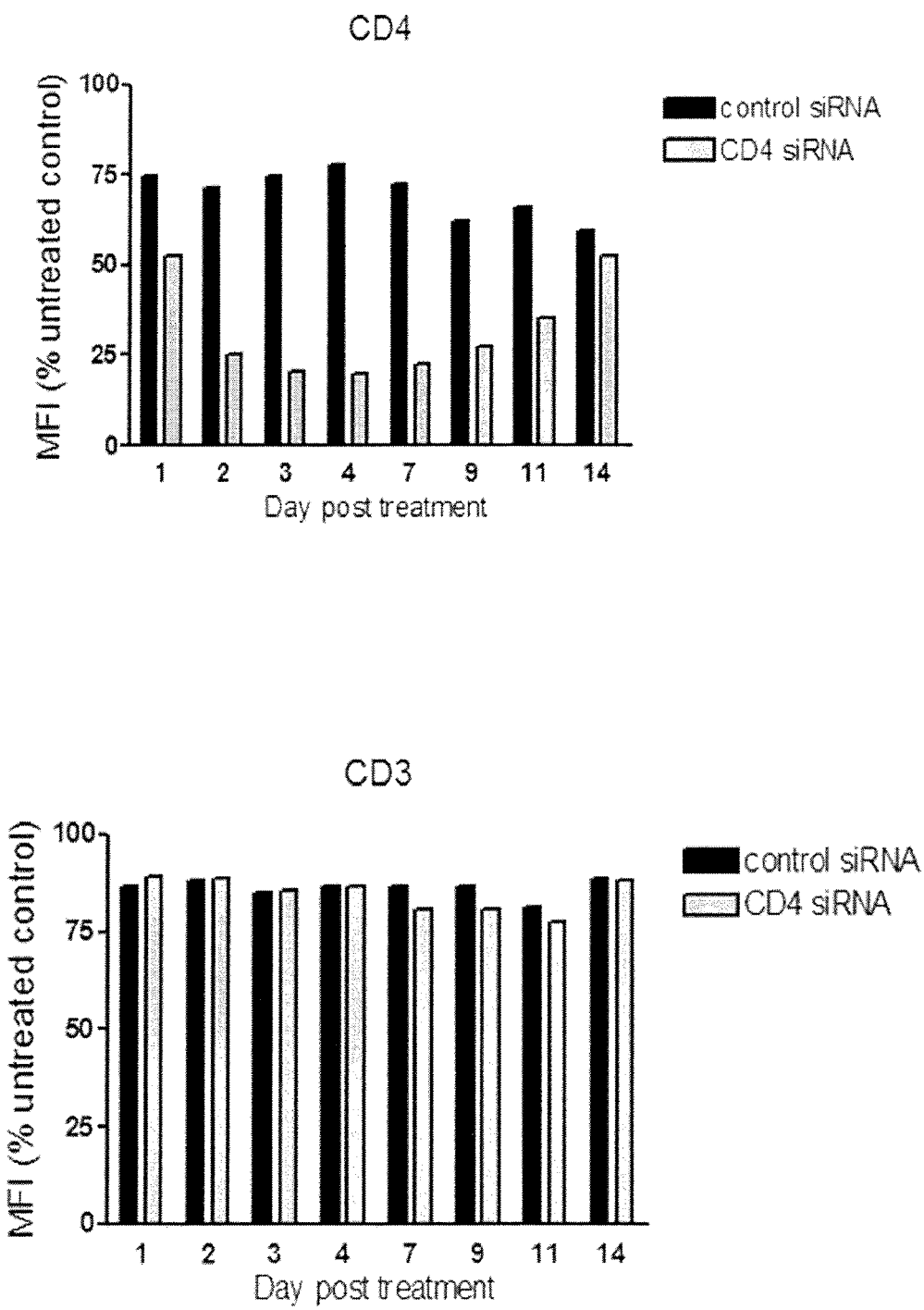
FIG. 15 is a series of bar graphs showing expression levels of CD4 in CD4+ human T cells over 2 weeks post-treatment as measured by flow cytometry. CD3 levels were also measured as a control gene.
Figure 16:
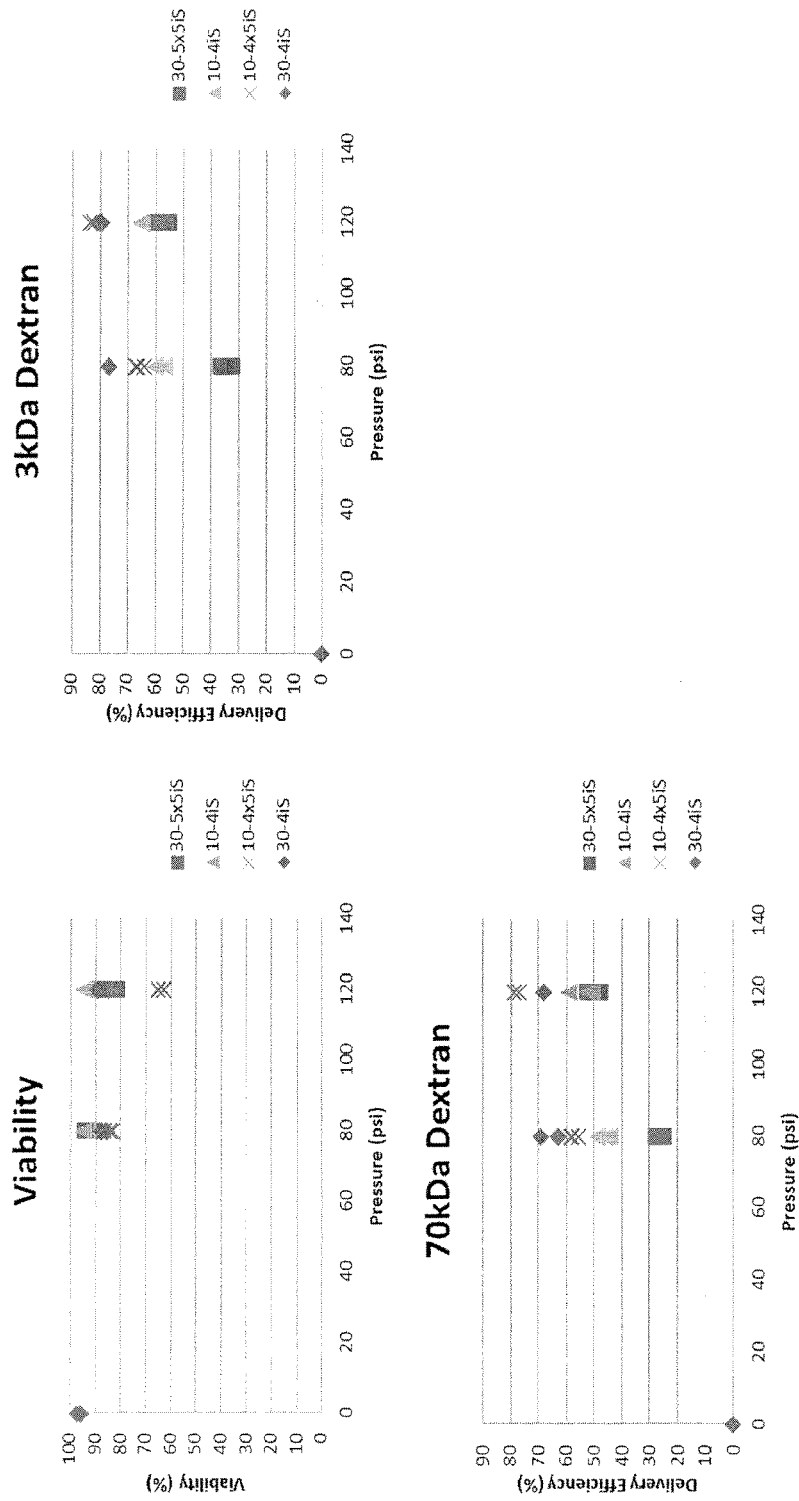
FIG. 16 is a series of graphs showing delivery of model cargo, dextran, to human monocytes. Monocytes were derived from human blood. Cascade blue labeled 3 kDa dextran, and fluorescein labeled 70 kDa dextran were delivered using four different device designs at two different operating pressures. The Opsi case corresponds to controls that were only exposed to dextran but not treated by the device. Viability was measured by propidium iodide staining.
Figure 17:
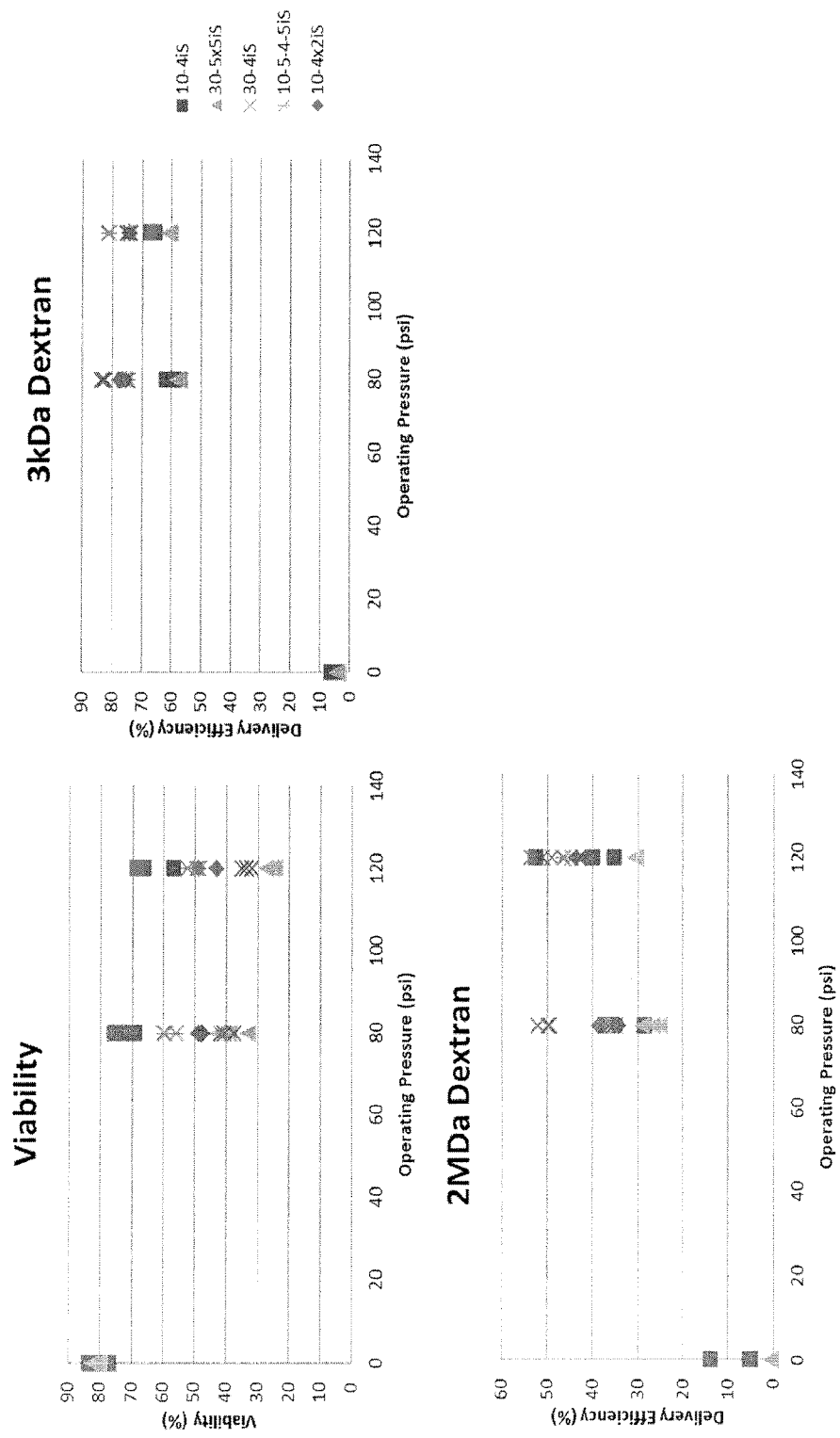
FIG. 17 is a series of graphs showing delivery of dextran to human B cells. B cells were derived from human blood. Cascade blue labeled 3 kDa dextran, and fluorescein labeled 2 MDa dextran were delivered using five different device designs at two different operating pressures. The Opsi case corresponds to controls that were only exposed to dextran but not treated by the device. Viability was measured by propidium iodide staining.
Figure 18:
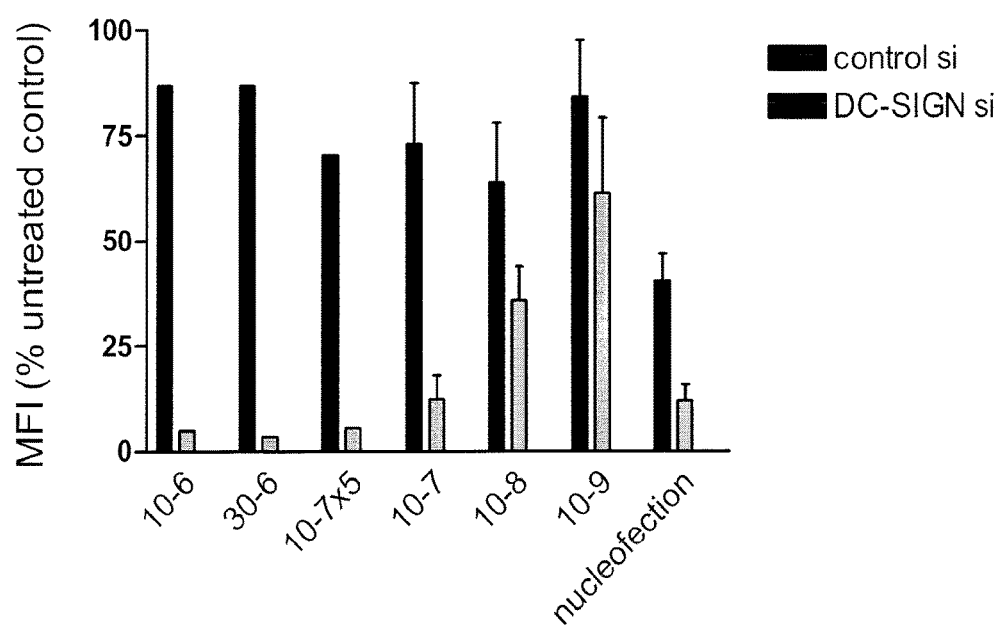
FIG. 18 is a bar graph showing measured protein levels of DC-Sign 72 hrs after treatment. Protein knockdown was measured across 6 different device designs and compared to nucleofection. Note that nucleofection appears to cause ~50% non-specific knockdown of DC-Sign even in the case of control siRNA delivery. This may indicate off-target effects due to the electroporation treatment. i.e. exposure of cells to the electric fields resulted in damage to the cells, specifically the target proteins, resulting in a measured reduction in expression levels in the absence of siRNA targeting the protein. These results indicate that the membrane deformation method is more specific compared to electroporation/nucleofection methods, which are associated with non-specific (off-target) effects.

To test protein knockdown, siRNA against human CD4 or CD45RA was delivered to blood derived T cells and observed dose-dependent knockdown of protein levels 72 hours post-treatment using 5, 1 and 0.2 µM siRNA, while control siRNA had not significant effect (FIG. 3B, FIGS. 12, 13). CD4 mRNA was also reduced when measured by qRT-PCR 48 hrs post treatment (FIG. 14). The durability of CD4 knock-down in T cells treated with 5 µM CD4 siRNA was also tested. Knockdown lasted ~10 days (FIG. 14). The delivery of siRNAs targeting the dendritic cell marker DC-SIGN also resulted in significant, sequence-specific, knockdown of DC-SIGN protein expression in MDDCs using different device designs. The level of knock-down in different device designs correlated with dextran/Ab delivery efficiency. Representative histograms of protein expression and compiled knockdown data from independent experiments for CD4 T cells and MDDCs are shown in FIG. 3B. The approach was also found to be applicable to human regulatory T cells (FIG. 3C), B cells and monocytes (FIGS. 16, 17, 18).

Figure 19:
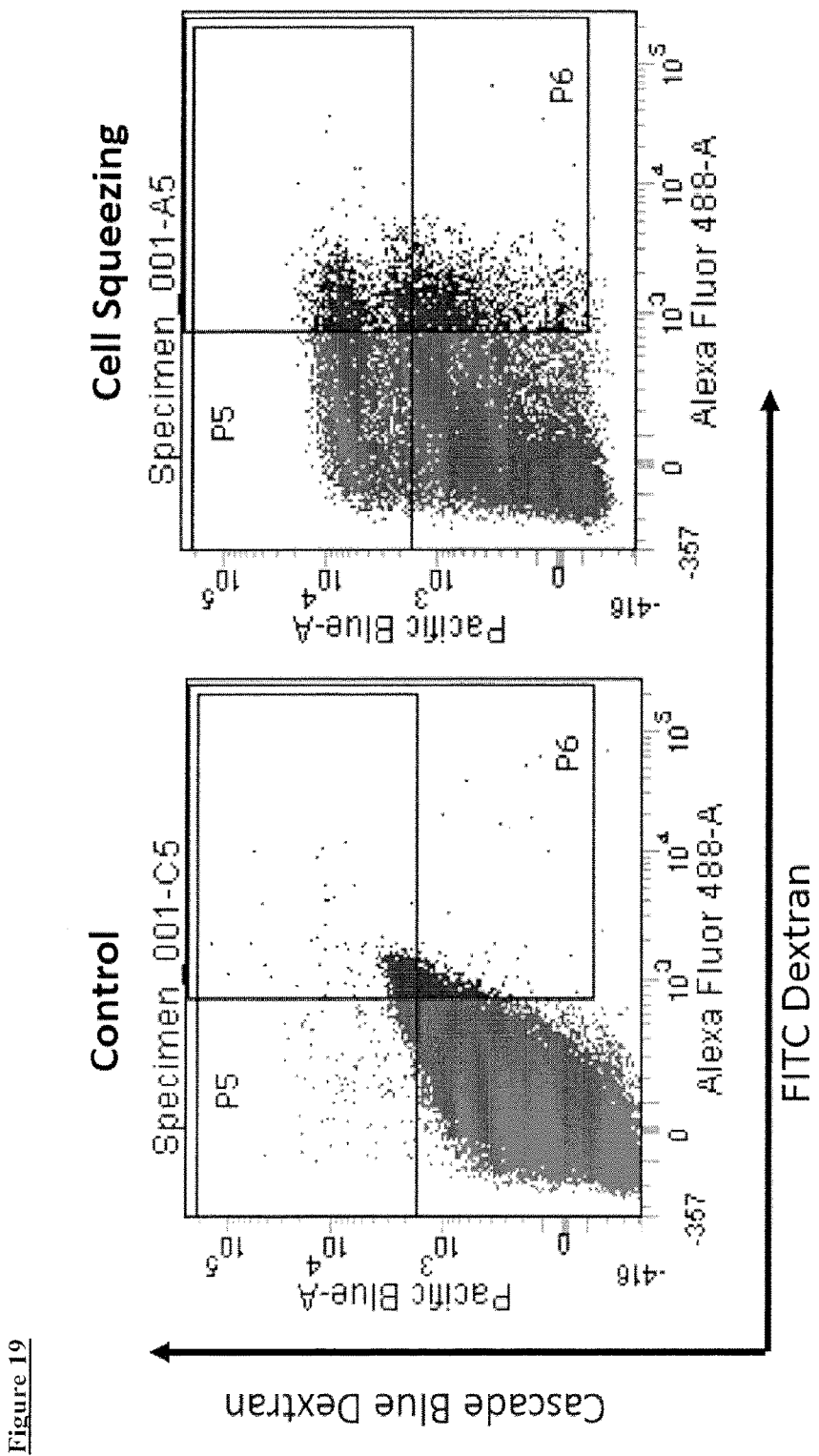
FIG. 19 is a series of graphs showing data pertaining to the delivery of impermeable alexa-488 labeled 10 kDa dextran dyes to cells in whole blood. Fluorescently labeled dyes were mixed with whole blood, and the mixture of whole blood+labeled dye ran through the device, and then measured for delivery to the blood cells by FACS after RBC lysis. The results demonstrate that the dyes were successfully delivered into the cells and that cargo compounds that have been characterized as "cell impermeable" are effectively delivered to immune cells using cell squeezing. It is surprising that the delivery process works in whole blood. Whole blood is very hard to manipulate without purification, e.g., fractionation or separation of peripheral blood mononuclear cells from red blood cells yet devices disclosed herein are capable of delivering compounds into immune cells in whole blood well. For a non-limiting example, see FIGS. 33 and 34.
Figure 20:
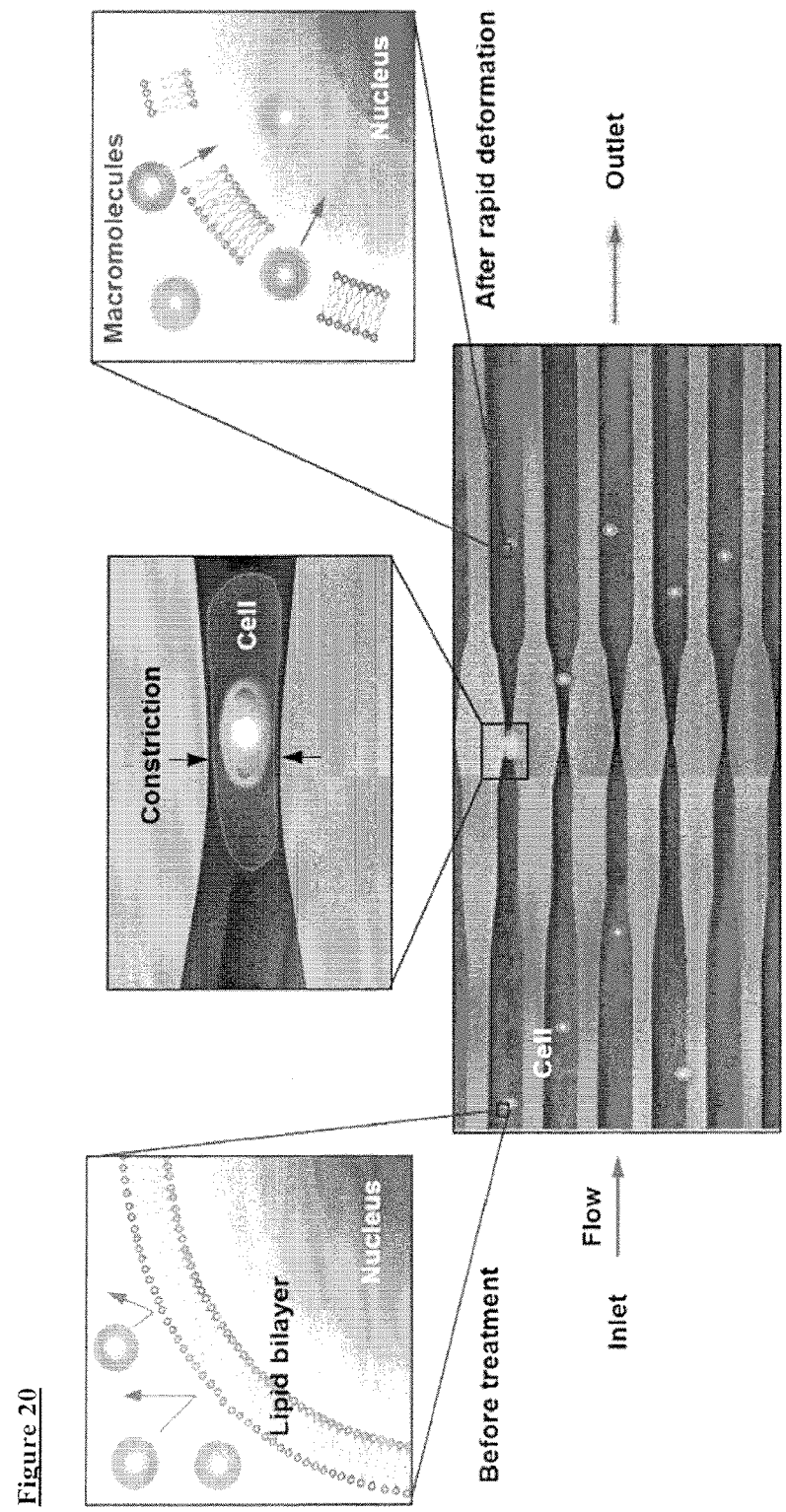
FIG. 20 is a diagram of the microfluidic membrane disruption system.
Figure 21A:
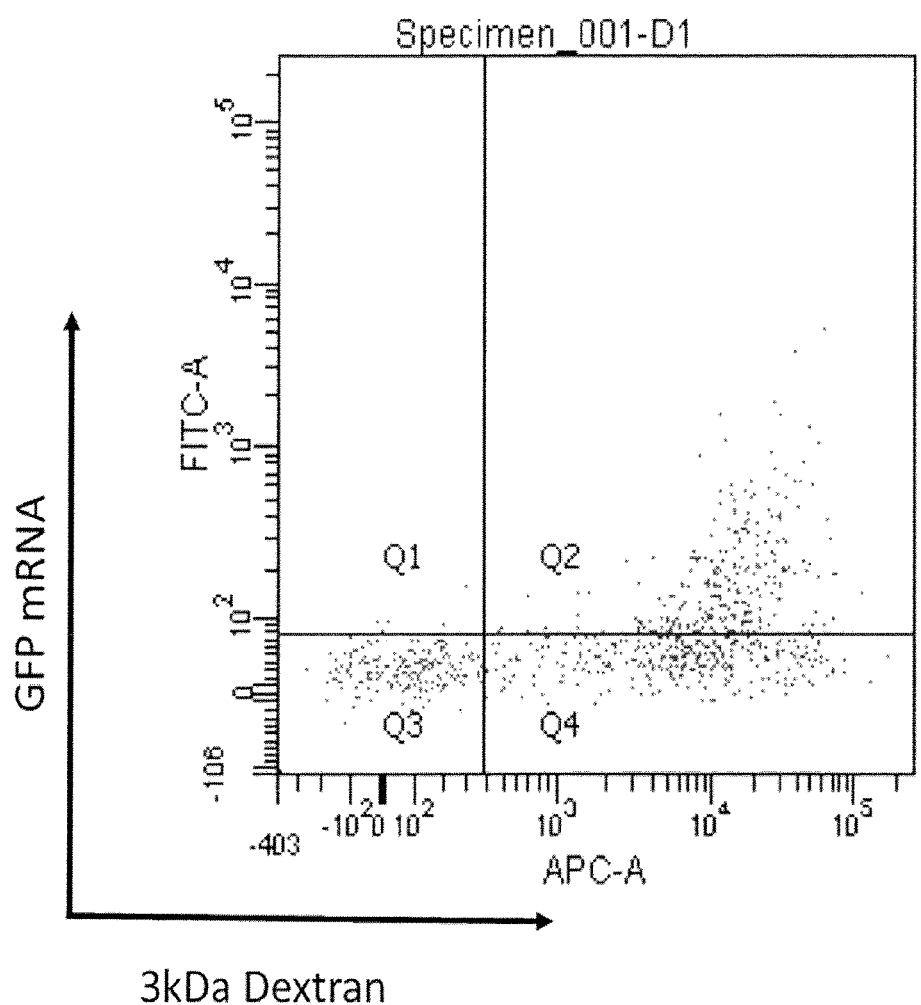
FIGS. 21A-B are dot plots showing mRNA expression one day after delivery with a 10-4 chip at 120 psi in Optimem buffer.
Figure 21B:
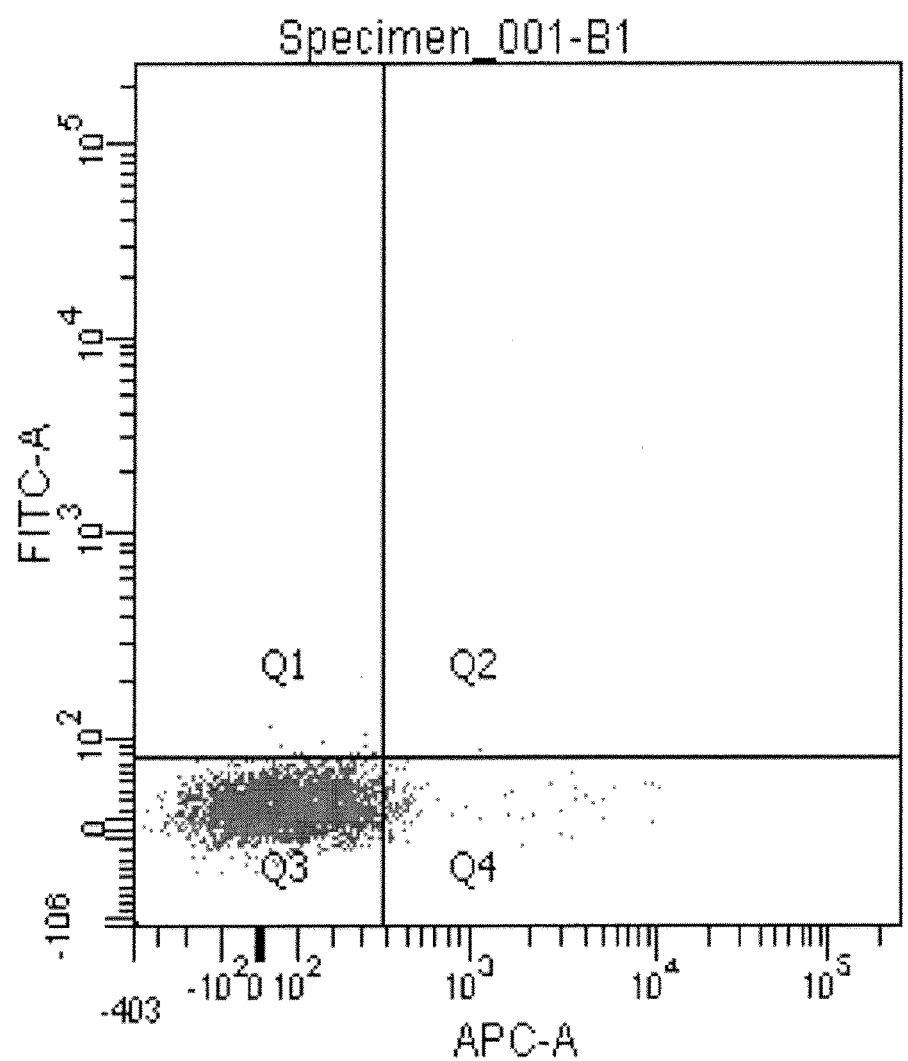
Figure 22A:
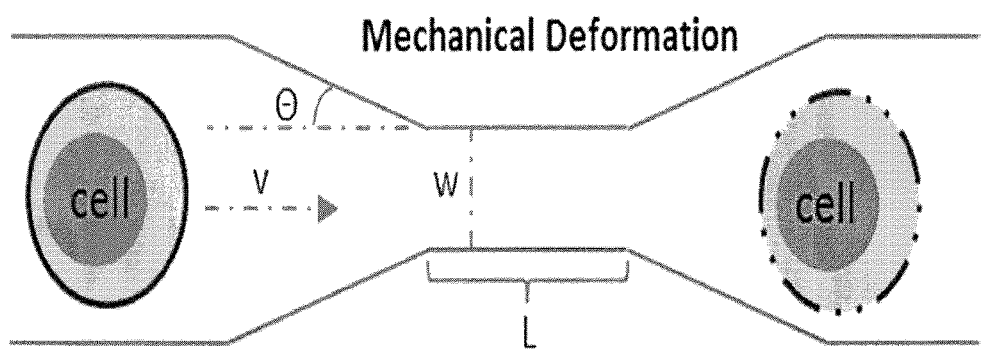
FIG. 22A is a diagram and FIG. 22 B is a bar graph showing delivery of 10 kDa alexa 488-labeled dextran at different pressures with different chip angles. The number in parenthesis is the constriction angle. Chip angle range from 0-180 degrees, e.g., 11-105 degrees. The schematic indicates chip angle. Depth parameter ranges from 2 μm to 1 mm, e.g., ~20 pm and is further described in U.S. Patent Pub. No. 20140287509 (hereby incorporated by reference). Exemplary parameters include 0-30 μm length/3-4 μm width/20 μm depth/11 degree angle fot naïve T and B cells.
Figure 22B:
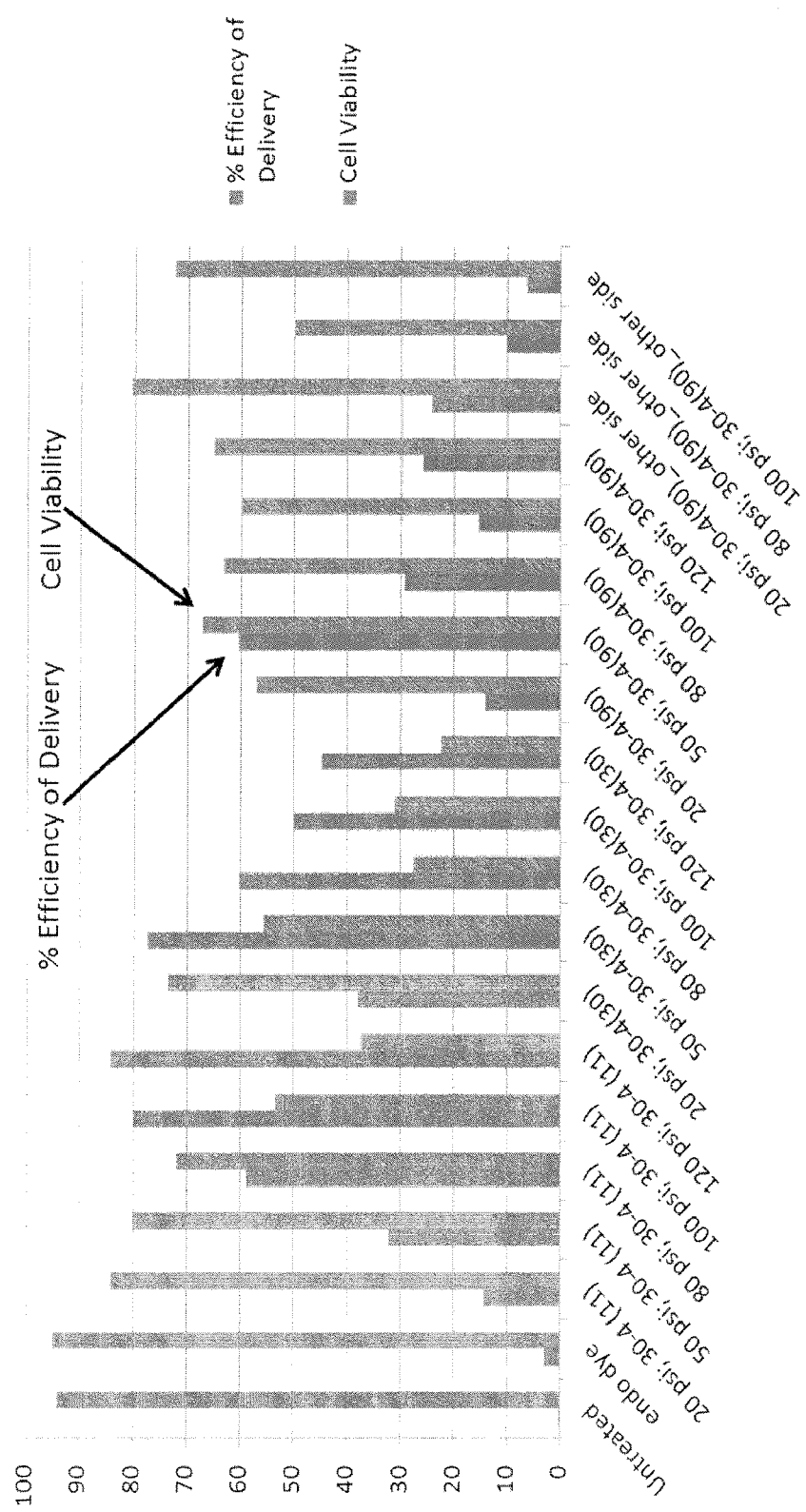
Figure 23:
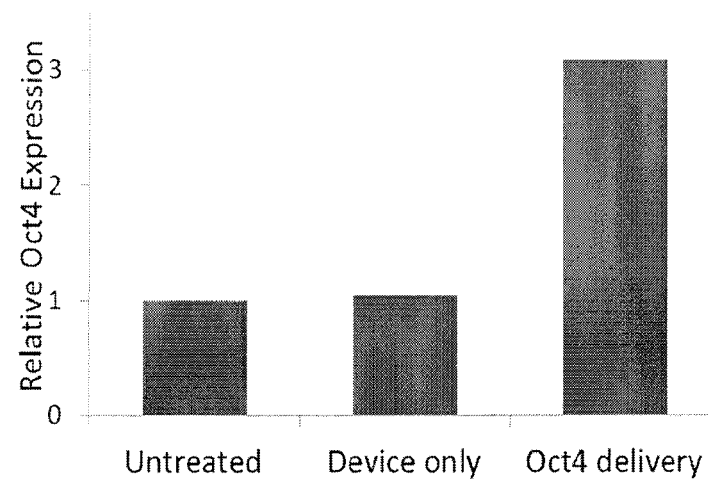
FIG. 23 is a line graph showing transcription factor delivery to NK cells and pDCs. A Oct4 mRNA expression was measured 4 hours after delivery of Oct4 recombinant protein to splenic mouse NK cells. These data indicate that the transcription factor is active and capable of inducing expression of endogenous Oct4. The Oct4 transcription factor is one of the four factors required for iPS generation (Oct4, Klf4, cMyc, Sox2) and exercises positive feedback control on itself. Delivery of active Oct4 protein yields increased Oct4 mRNA expression. Delivery of active transcription factors is a critical step in the reprogramming process for protein-based methods. These methods have many advantages over viral and DNA based systems as they minimize the risk of integration.
Figure 24A:
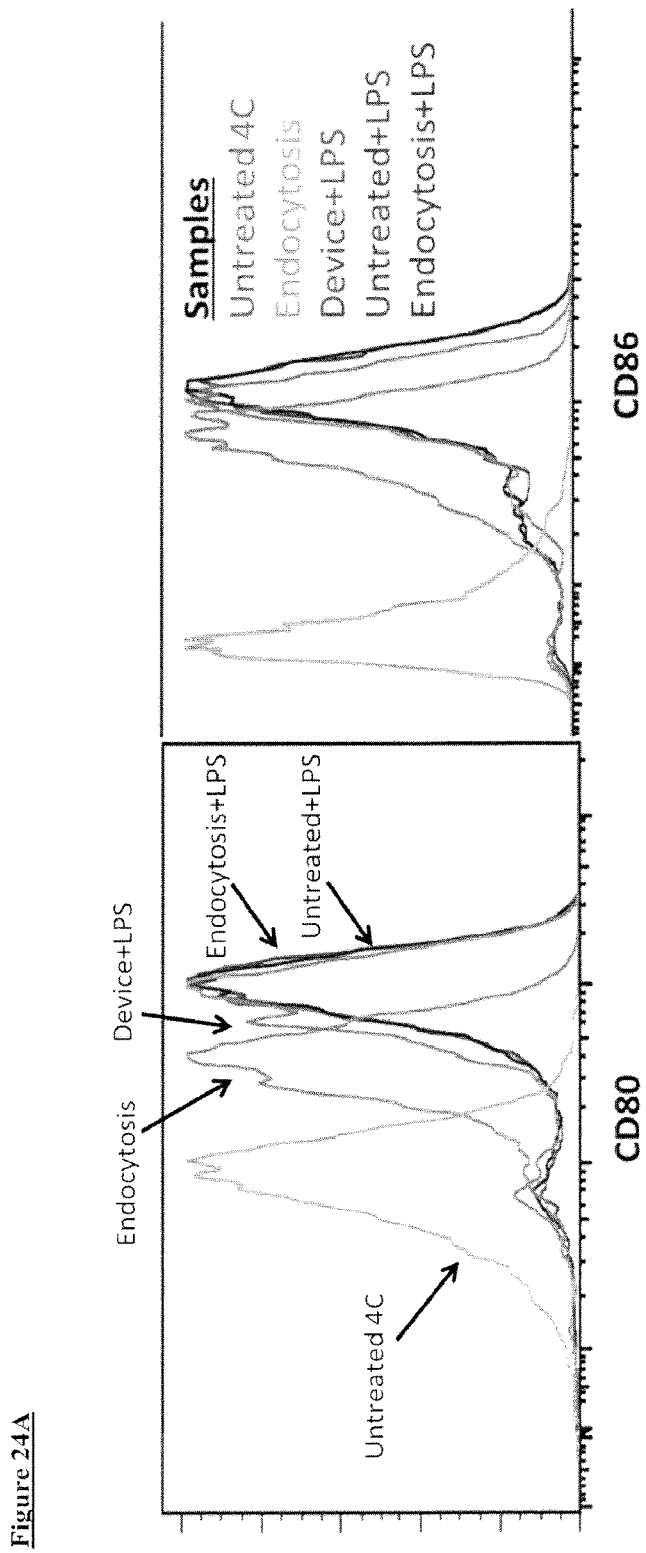
FIGS. 24A-B are line graphs showing that no detected inhibition of normal DC function was observed in response to squeezing.
Figure 24B:
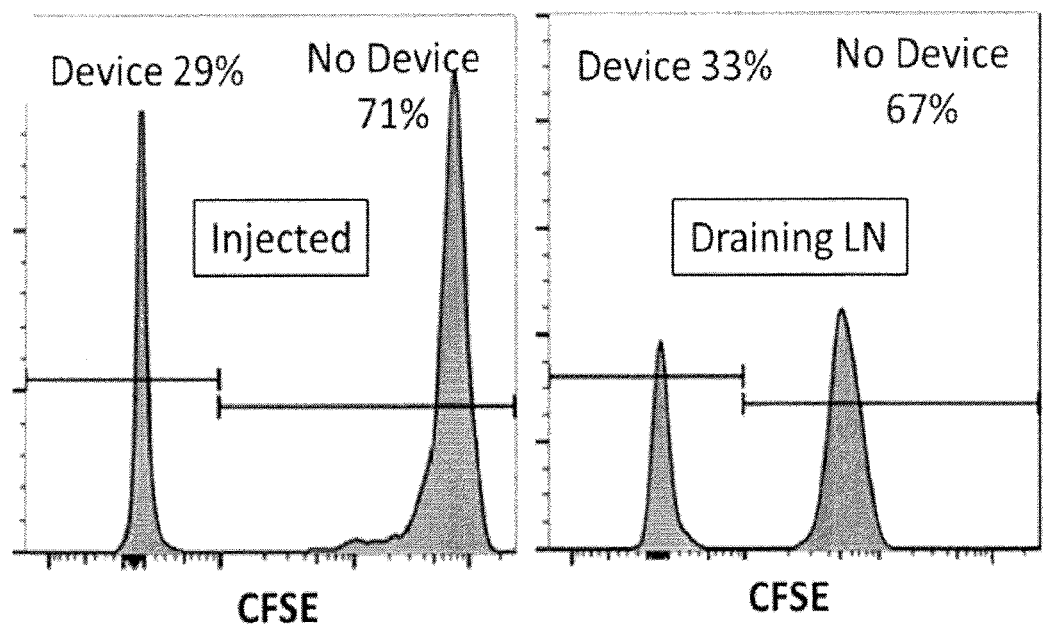
Figure 25A:
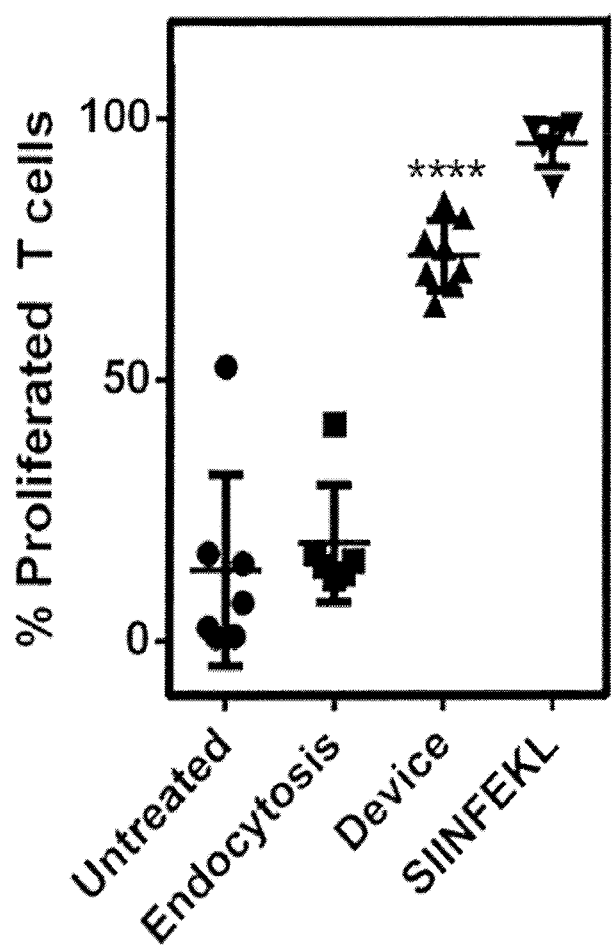
FIGS. 25A-D are graphs showing that use of the membrane deformation device system and methods lead to more effective antigen presentation compared to other antigen delivery approaches.
Figure 25B:
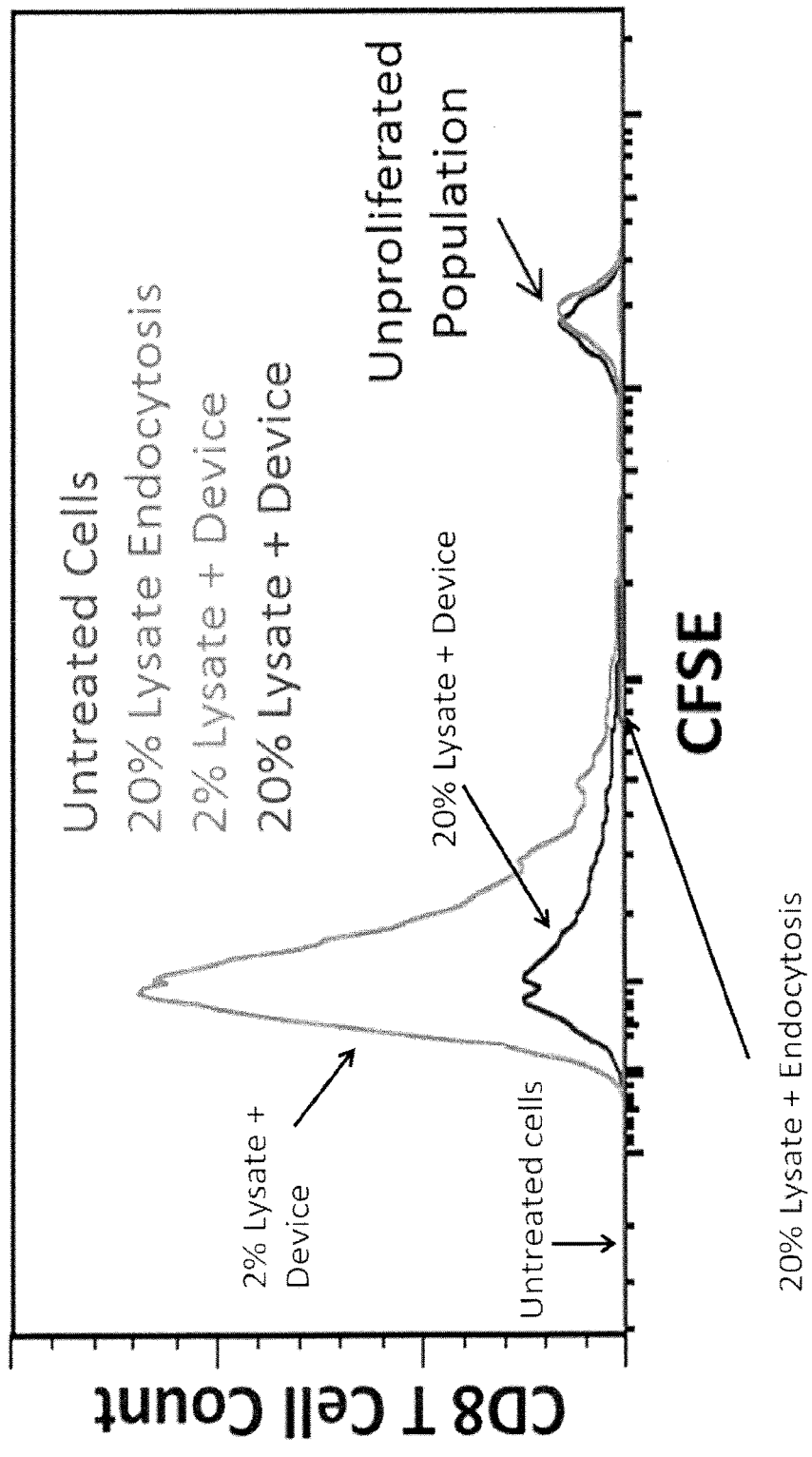
Figure 25C:
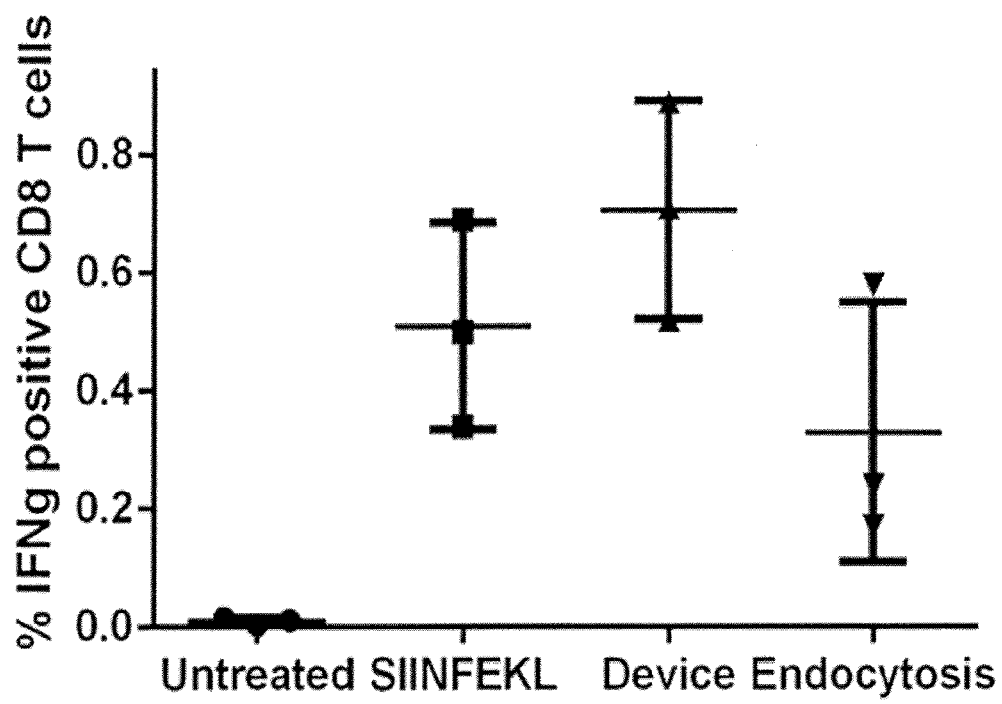
Figure 25D:
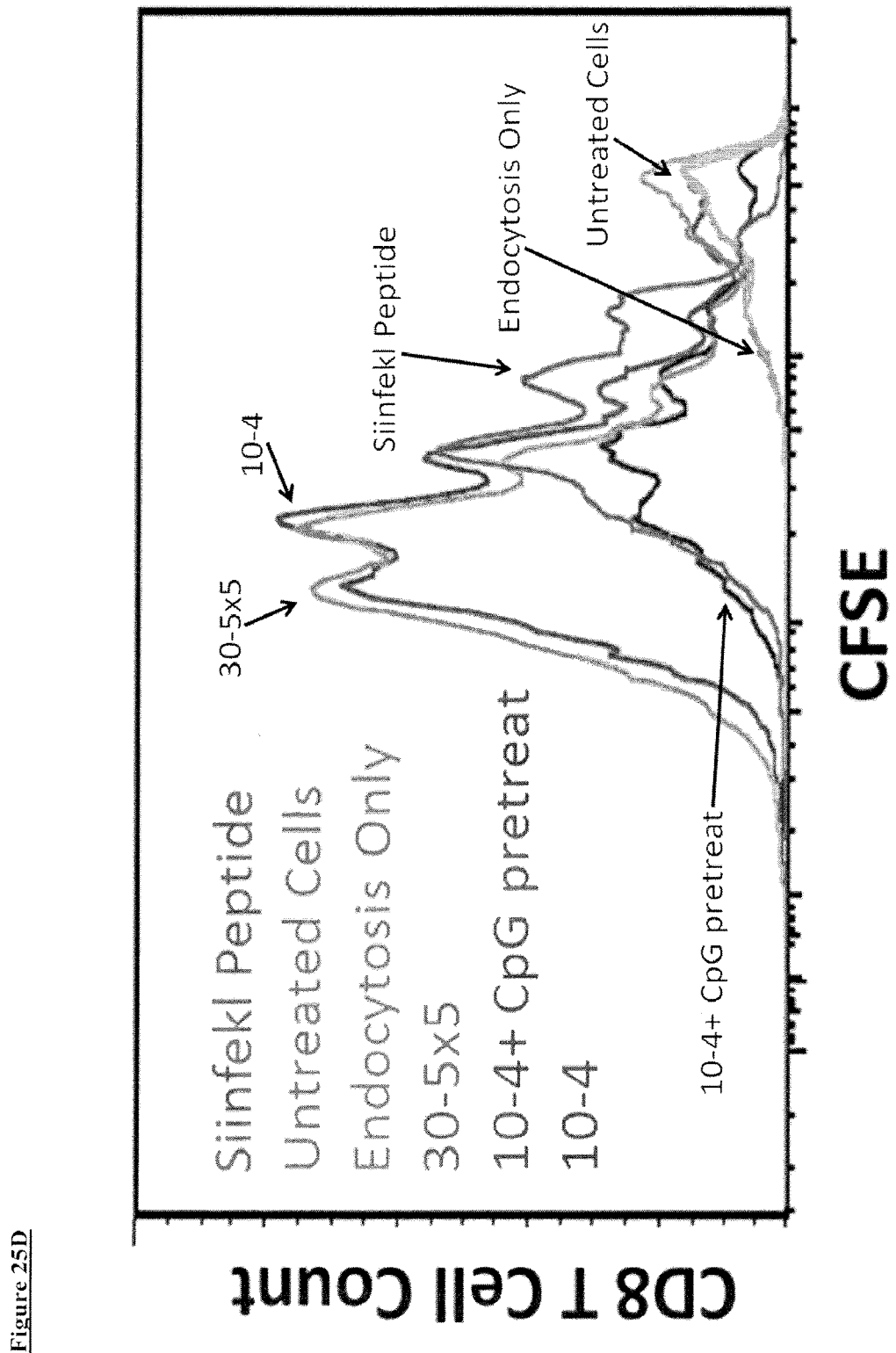

To compare the performance of the microfluidic device to nucleofection (an electroporation-based approach to nucleic acid delivery) human CD4 T cells were treated with siRNAs in parallel by the CellSqueeze platform or a nucleofection machine, and protein knockdown was measured 72 hrs later by flow cytometry. Although the extent of CD4 knockdown was similar between the two (FIG. 3D), T cell viability post-nucleofection, was significantly worse than in cells treated by the microfluidic device (P<0.05). The efficiency of the two platforms for delivery of labeled dextrans and proteins was compared. Comparison of the performance of the deformation device to nucleofection, in the context of MDDCs, yielded similar results to T cells. Specifically the best microfluidic device (30-4 for T cells, 10-6 for MDDCs) displayed advantages in cell viability and delivery (FIG. 18). Comparisons of siRNA knockdown efficiency between the two techniques also indicated that cell squeezing causes less off-target effects (FIG. 19) and improves long-term viability.

Inhibition of HIV-1 Infection in Primary Human T Cells

Figure 4:
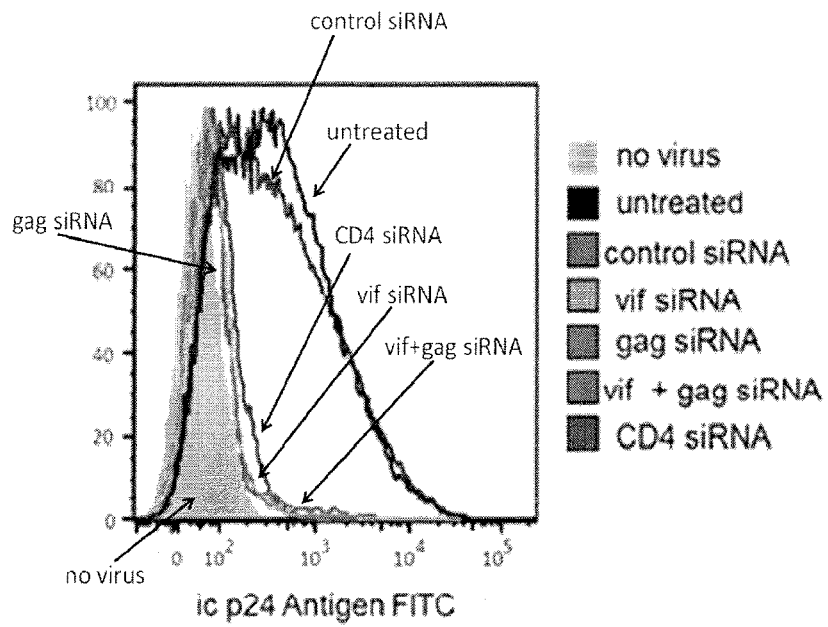
FIGS. 4A-B are graphs showing inhibition of HIV infection by targeted knockdown of endogenous and viral genes. In Figure A, intracellular staining for the p24 antigen was used as an indicator of HIV infection level in treated human CD4+ T cells 24 hrs after infection. In these studies, vif and/or gag, siRNA was delivered 24 hrs prior to infection while CD4 siRNA was delivered 48 hrs prior to infection.
FIG. 4N shows median fluorescence intensity of the p24 antigen stain across repeats (min. N=4) of the experimental conditions. Data is represented as mean+1 standard error.
Figure 4:
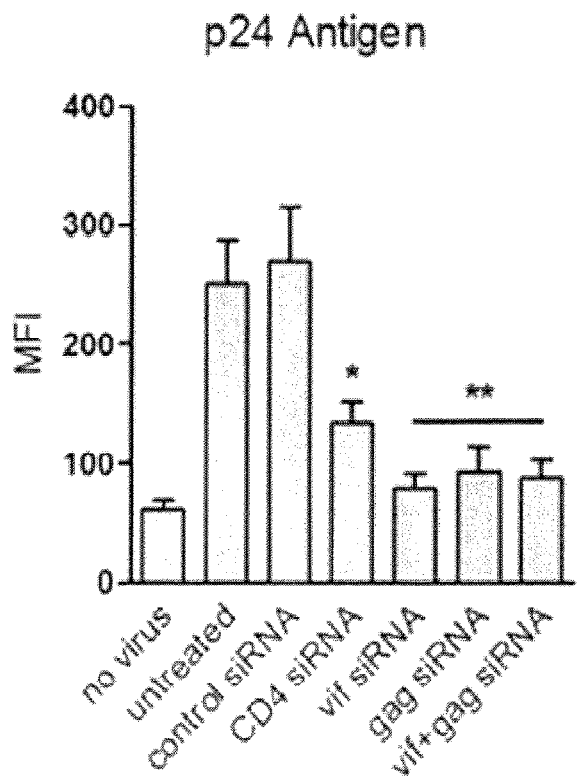

Studies were carried out to determine whether the microfluidics approach was useful to inhibit HIV infection and replication in human primary CD4+ T cells by delivering siRNA targeting viral genes. siRNA against vif and gag, which were previously shown to suppress viral replication, was delivered to cells 24 hrs prior to infection with HIV. As a positive control, siRNA targeting the HIV receptor CD4 was used. The CD4 siRNA was delivered 48 hrs prior to infection to ensure reduction of surface CD4 levels, thus inhibiting infection. HIV replication was determined by staining for intracellular p24 antigen and measured by flow cytometry. Representative histograms and compiled results from independent infection experiments are shown in FIGS. 4A-B. A significant reduction of p24 antigen was observed in T cells treated with vif and gag targeted siRNA, both separately and in combination (p<0.01). The inhibitory effect was greater than that induced by CD4 knock-down (p<0.05) (FIGS. 4A-B).

Ex Vivo Cytostolic Delivery of Compounds to Immune Cells Using Cell Shaped Alteration Device Intracellular delivery of macromolecules to immune cells was a significant challenge prior to the invention. Results shown here demonstrate the utility of a vector-free membrane disruption technique to deliver small molecules as well as large macromolecules to eukaryotic cells such as mouse and human immune cells. The results are surprising and particularly relevant to clinical use, because immune cells are recalcitrant to other techniques of delivering compositions to the cytoplasm of these cells. The data described herein demonstrates: (i) the ability to deliver a diversity of biologically relevant macromolecules (polysaccharides, proteins, and nucleic acids); (ii) efficacy in the most clinically-relevant immune cell subsets (T cells, B cells, DCs, monocytes/macrophages) (FIGS. 2A-C and FIGS. 3A-D); (iii) independence from vector material and electrical fields, thus overcoming some of the challenges associated with endocytic entrapment and electroporation-level toxicity; and (iv) the simultaneous delivery of multiple classes of macromolecules to target cells (FIGS. 2C, 9, 12, 13).

These surprising and significant advantages enable previously unforeseen immune cell manipulations and clinical applications. For example, this system serves as a platform for delivery of peptide or protein-based therapeutics to lymphocytes, materials in which existing methods, e.g. electroporation, have shown limited efficacy. The simultaneous delivery feature of the system is also useful to screen multiple therapeutic candidates in parallel to accelerate the screening process and potentially identify complementary effects. Additionally, the use of similarly sized, labeled, molecules as tracers allows one to monitor delivery efficiency of an unlabeled target material independently. Other imaging agents, such as quantum dots, may also be delivered using this system, thus facilitating direct observation of molecular interactions in live cells to gain a deeper understanding of biological processes.

In a non-limiting example, a quantum dot or a magnetic nanoparticle is delivered to facilitate in vivo imaging of transferred immune cells. For example, an MM could detect localization of adoptively transferred T cells loaded with magnetic particles.

The dependence of delivery performance on system parameters, such as constriction geometry, temperature, operating pressure and buffer composition are tailored for delivery of compounds/compositions to immune cells or mixtures of immune cells, e.g., cells in whole blood. For example, exemplary device parameters for immune cells include (T cell, 30-4 resting, 10-4 activated), B cell (30-4 resting, 10-4 activated), macrophage (10-6), dendritic cell (10-6) as well as mixture such as white cell fraction/buffy coat cells or whole blood cells. The range of constriction designs for all is 2-10 µm width, 0.1-90 µm length). Thus, one could optimize performance of the platform in target lymphocyte and myeloid cell populations by developing device architectures and operating protocols using design rules established for other cell types. For example, one could increase delivery efficiency by fabricating devices with longer, narrower constrictions. Throughput of the system, currently at 100,000-1,000,000 cells/second, can also be increased by including more parallel channels per device or increasing operating pressure. In some embodiments, channel depth is increased or additional channels are added in parallel to increase throughput. Operating pressure may vary depending on the device's design. In certain embodiments, the pressure is 1 psi to 1000 psi.

The vif and gag knockdown studies demonstrate the potential of this approach to alter cell phenotype and influence disease-relevant biological processes, such as viral (e.g., HIV) replication (FIGS. 4A,B). This result not only demonstrates the utility of this approach disease treatment and in studying disease mechanisms (e.g. the dependence of viral replication on specific genes), but also demonstrates engineering of immune cells for clinical use by targeting specific host cell functions/pathways without the use of potentially toxic delivery vectors. Protein transcription factors delivered by squeezing, e.g., IRF5, can be used to increase IFN-α production in human pDCs, thus demonstrating that proteins delivered by squeezing are also functional and able to influence cell phenotype. This intracellular delivery system is therefore useful for immune cell engineering with capabilities beyond that of extracellular antibody and cytokine-based approaches.

The data described herein show the surprising efficacy of the viral vector-free, microfluidic approach to cytosolic delivery for immune cells, which (prior to the invention) were difficult to engineer and difficult to achieve cytosolic delivery of compounds/compositions. The data further demonstrates the ability of this approach to facilitate the delivery of a variety of macromolecules, including polysaccharides, proteins and nucleic acids, to T cells, B cells, myeloid cells (CD11b+), and dendritic cells. The functionality of the delivered material was verified in siRNA-based knockdown studies targeting five different genes. Finally, the HIV infection studies underscore the utility of this approach to alter cell phenotype and influence viral replication for inhibition of infectious diseases. The vector-free delivery system described herein provides a safe, reliable, and effective method for engineering the function of immune cells and/or altering their phenotype, function, state of activation.

Rapid Response Vaccine System for Unidentified Pathogens

Infectious pathogens pose a serious threat to soldiers and civilians alike. To protect against potential biological attacks and the evolution of pandemic viruses, one must develop robust, rapid-response vaccination capabilities. With state-of-the-art technologies, even if a virulent strain can be isolated and characterized by scientists, it can take years and billions of dollars to develop effective vaccines. Many deadly pathogens, such as Ebola and HIV, still cannot be addressed by contemporary vaccination methodologies despite decades of study. The invention provides methods and devices for rapid-response, multi-targeted, personalized protection against pathogens by directly engineering an individual's immune cells using the vector-free intracellular delivery platform described herein. The method enables effective vaccination of a local at-risk population within hours of identifying newly infected individuals and has several advantages over previous approaches as shown below in Table 3.

TABLE 3

| Vaccine Characteristics | Attenuated Virus Vaccines | Recombinant Antigen + Adjuvant | Adoptive Transfer | Rapid Response Vaccination Platform |
|---|---|---|---|---|
| Efficacy | High | Moderate | Moderate/Low | High |
| Development Time (per indication) | Years | Months | Months | Hours |
| Development Cost (per indication) | High | Moderate | High | Low/None |
| Treatment Cost | Low | Moderate | High | Low |
| Field-deployable | Yes | Yes | No | Yes |

Direct delivery of antigenic proteins to the cytoplasm of an individual's APCs (e.g., B cells, DCs, and re-programmed T cells) obviates the need for identification and development of attenuated viral vectors while providing more effective protection through inducing multi-targeted immune responses necessary to counter-act viral escape. The field-deployable vaccination platform addresses an outbreak within hours, not months/years.

Figure 5:
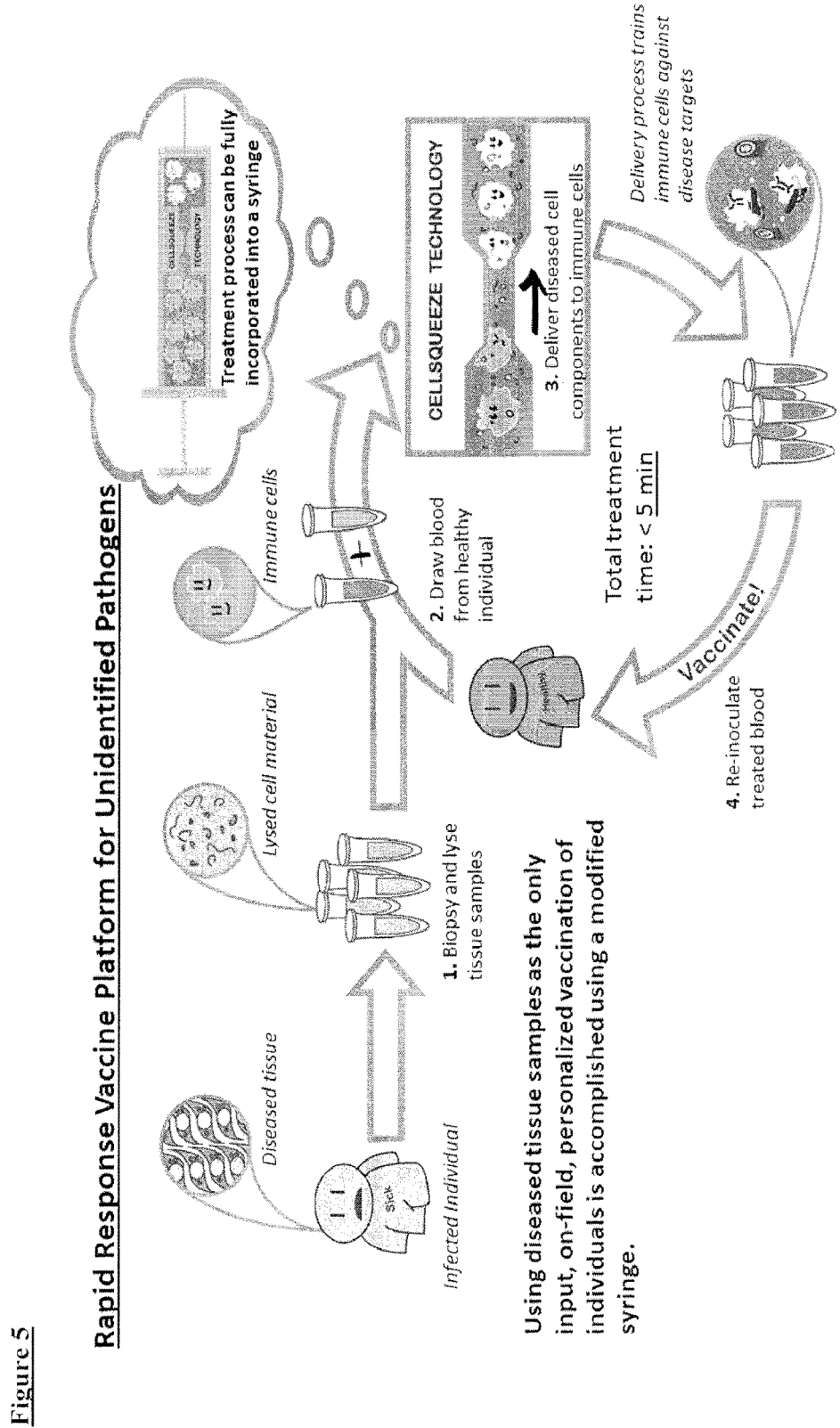
FIG. 5 is a diagram of a vaccination method.
Figure 6:
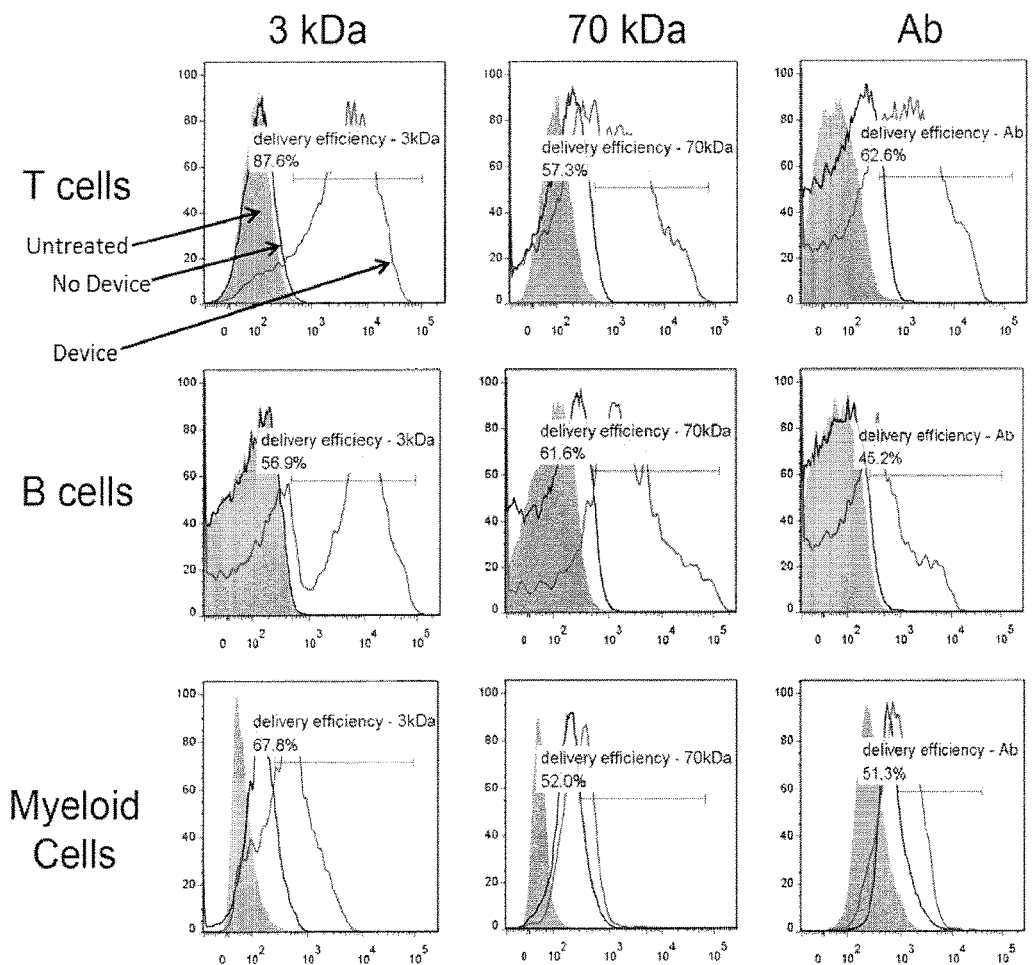
FIG. 6 is a series of line graphs showing uptake of 3 kDa and 70 kDa dextran and antibody to murine primary immune cells. The gating used to calculate delivery efficiency values is shown. These data correspond to experiments presented in FIG. 2. Grey histograms represent untreated cells, black represents cells that were exposed to the materials but not treated by the device, red represents cells that were treated by the device in the presence of the target biomolecules.

When a pathogen is suspected in an individual, one first takes a biopsy the infected tissue. This tissue, which contains the pathogen, is lysed such that the molecular components (i.e. the antigens) remain intact, while, the pathogen is deactivated due to the lysis process. This antigen mixture is then delivered to the immune cells of a healthy individual by drawing their blood and driving their cells through the microfluidic intracellular delivery device (3), before re-entering the blood stream. This delivery process introduces the pathogen associated antigens into the cytoplasm of resident APCs in the blood, which includes T cells, B cells, dendritic cells and monocytes. The antigen fragments are then presented by the MHC-I and drive the activation of disease-specific cytotoxic T cells CTLs to provide protection. Lysis can be completed within 1-2 hours of obtaining an infected biopsy (generating doses for multiple healthy patients from a single biopsy) and the subsequent inoculation of healthy patients would require <5 min per person. (FIG. 5) Moreover, if a pathogen has been characterized, e.g. in the case of HIV or Ebola, one can substitute the use of cell lysate with chemically defined synthetic peptides as the antigen source, thus eliminating potential safety concerns surrounding the use of lysates.

The rapid response vaccine platform provides a first-line defense against a variety of biological threats when a conventional, expensive multi-year development process can lead to substantial loss of life. This approach to vaccination is also applicable to oncology and infectious disease treatments.

Microfluidic Squeezing for Intracellular Antigen Loading in B Cells

Antigen presenting cells (APCs) are a diverse subset of immune cells (including dendritic cells, macrophages, B-cells) that capture foreign or self proteins and peptides from tissues, and activate adaptive immune cells to generate either an inflammatory or tolerogenic immune response against these antigens. Proteins are ingested by APCs in vivo via fluid-phase sampling of their surroundings or receptor-mediated ingestion of foreign microbes or dead cell debris. Ingested proteins are degraded into peptide fragments (antigens) which are processed and presented to T-cells together with costimulatory signals, instructing naïve T-cell activation based on the specific signals received by the APC and the antigens presented. Because of this critical role in T-cell activation, purified APCs loaded with antigen and activated ex vivo can be used to expand functional T-cells in culture (e.g., for adoptive T-cell therapy) or as effective cellular vaccines in vivo. Using the microfluidic system, ex vivo manipulation of APCs was shown to be effective as an alternative approach for generating specific types of immunity, particularly cytotoxic T lymphocytes (CTLs) in diseases such as cancer and HIV, where targeted killing of pathogenic cells is critical and endogenous APC function is actively suppressed. Despite promising preclinical studies, clinical translation of cell-based vaccines has been hampered by multiple limitations. The microfluidic device and associated methods for delivery of antigen to the cytosol of immune cells solves many problems and drawbacks of earlier approaches.

Previous clinical research on cell-based vaccines has focused on dendritic cells (DCs), the so-called—professional—APCs because of their efficiency in priming CTLs, and their highly active extracellular protein uptake and antigen-processing capability. However, as a platform for clinical use, DCs are limited by their relative paucity in human blood, complex subset heterogeneity, short lifespan, and inability to proliferate. These challenges have led other cell types to also be considered for cell-based APC vaccines, including macrophages and B-cells. B-cells are a desirable population of cells for this purpose, because of their unique properties as lymphocytes and their potential to overcome many limitations of DCs. For example, B-cells are abundant in circulation (up to 0.5 million cells per mL of blood), can proliferate upon cellular activation, and efficiently home to secondary lymphoid organs when administered intravenously.

These advantages of B-cells as APCs are offset by limitations in the ability of B-cells to acquire and process antigen for priming of T-cells. B-cells express genetically rearranged B-cell receptors (BCR), which on binding to their target antigen, promote antigen uptake and B-cell activation. While B-cells are able to internalize antigens via their BCRs and prime primary T-cell responses, their uptake of non-specific antigens (i.e. antigens not recognized by their BCR) is poor compared to macrophages and DCs, which efficiently pinocytose and phagocytose antigens from their surroundings. Furthermore, priming of CTLs occurs through presentation of peptide by class I MHC molecules, which are normally only loaded with antigens located in the cytosol (where the class I MHC processing machinery primarily resides). By contrast, proteins taken up via the BCR into endolysosomes tend to be directed to the MHC class II presentation pathway for presentation to CD4+ T-cells. Alternatively, B-cells and other professional APCs can load class I MHC molecules with peptides via cross presentation, a process whereby class I peptide-MHC complexes are produced from endocytosed antigens via proteasomal processing or vacuolar protein degradation, but this process is generally very inefficient.

Although methods have been developed to increase antigen uptake and cross-presentation in B-cells, these strategies largely rely on targeting specific receptors for endocytic uptake, activating B-cells combined with fluid-phase protein exposure to increase non-specific endocytosis, delivering antigen as immune-stimulating complexes, or generating fusion proteins to direct B-cell function. These approaches are limited by the fact that antigen uptake is coupled to other changes in B-cell state mediated by signalling through the targeted receptor, meaning that antigen loading and B-cell activation cannot be separately tuned. For example, resting B-cells have been shown to be tolerogenic to naïve CD8+ T-cells, a potentially useful property in treating autoimmunity, and activation of the B-cell would be problematic in such an application. Transfection of B-cells with DNA, RNA33, or viral vectors encoding antigens has also shown promise, but has been limited by a host of issues such as toxicity of electroporation, viral vector packaging capacity, transduction efficiency, stability, and anti-vector immunity. The methods described herein provide a solution to these drawbacks of earlier approaches.

Direct cytosolic delivery of whole proteins, i.e., unprocessed antigen, into live B-cells by transient plasma membrane disruption/perturbation, is accomplished as B-cells are passed through constrictions in microscale channels of a microfluidic device (mechano-disruption. Using the well-defined and art-recognized model antigen ovalbumin (OVA), delivery of whole protein via this method enabled even resting B-cells to elicit robust priming of effector CTLs both in vitro and in vivo. This method for whole protein delivery and antigen presentation by MHC class I is the first antigen delivery method in B-cells that decouples antigen loading from the process of B-cell activation, allowing these two processes to be separately tailored for immunogenic or tolerogenic vaccines. Cell squeezing provides an alternative modular platform that primes autologous B-cells for in vitro CTL expansion as well as facilitate the development of B-cell-based vaccines.

The following materials and methods were used to generate data pertaining to antigen presentation.

Reagents. TRITC- and Cascade Blue-labelled 3 kDa dextrans were purchased from Life Technologies. FITC-labelled 40 kDa dextran was purchased from Chondrex. Model antigen, Low endotoxin ovalbumin protein was purchased from Worthington Biochemical Corporation. CpG ODN 1826 (CpG B), CpG ODN 2395 (CpG C), and LPS *Escherichia coli* K12 (LPS) were all purchased from Invivogen. Multimeric/megaCD40L was purchased from Adipogen and Enzo Life Sciences.

Cell isolation. Methods and procedures for isolating/purifying or enriching for immune cells or subsets of immune cells are well known in the art. For example for humans, peripheral blood mononuclear cells are obtained from whole blood taken by venipuncture and subsets of immune cells, e.g., B cells, T cells, dendritic cells, macrophages, separated using standard protocols. Bone marrow is also used as a source of immune cells.

For B-cell isolation in the examples described herein, spleens were harvested from mice and mashed through a 70 μm cell strainer. Red blood cells were lysed and resting B-cells were isolated from the cell suspension with the B-Cell Isolation Kit, mouse (Miltenyi Biotec) following the manufacturer's instructions. After isolation, B-cell suspensions were >95% B220+, as measured by flow cytometry. For CD8+T-cell isolation, spleens and inguinal lymph nodes were harvested and mashed. Following red blood cell lysis, CD8a+T-cells were isolated with the CD8a+T-cell Isolation Kit, mouse (Millenyi Biotec) according to the manufacturer's instructions. CD4+T-cell isolation was performed with the CD4+T-cell Isolation Kit, mouse (Millenyi Biotec) on spleen and inguinal lymph node suspensions. T-cells were consistently >90% pure, as measured by CD8a or CD4 staining and flow cytometry. All cell culture was performed in T-cell media (RPMI with 10% FBS, penicillin-streptomycin, 1× sodium pyruvate) supplemented with 1 μL/mL of 55 mM β-mercaptoethanol.

Protein delivery by cell squeezing. Delivery of whole protein antigen to resting B-cells was performed using CellSqueeze, a microfluidics device and pressure system (SQZ Biotech); chip designs used included 30-4×1, 10-4×1, and 30-5×5 where X-Y×Z denotes Z sequential constriction channels of dimensions X μm long and Y μm diameter. B-cells were suspended at $5 \times 10^6$ cells/mL in media with 100 μg/mL of ovalbumin, 0.3 mg/mL TRITC- or Pacific Blue-labelled 3 kDa dextran, or 0.3 mg/mL FITC-labelled 40 kDa dextran, and placed on ice. The microfluidics chips and holder set were also placed in an ice water bath until cold. The cell suspension was sent through the device in 200 μL aliquots at 120 psi. Endocytosis control B-cells were prepared identically in medium with OVA, but did not go through the microfluidics device. After antigen loading, cells were allowed to rest at room temperature for 5 minutes and washed twice with PBS. To assess delivery efficiency, uptake of antigens or other delivered was measured by flow cytometry (detection of fluorescently-labeled compositions).

In vitro cell culture, activation & proliferation assays. To characterize in vitro activation of mechano-porated B-cells, cells that went through the SQZ device and endocytosis control cells were incubated in a 96-well U-bottom plate at $5 \times 10^5$ cells/mL with 5 μM CpG B, 5 μM CpG C, or 100 ng/mL LPS. Flow cytometry was performed at 24 and 48 hours to measure cell-surface levels of CD86, CD40, CD69, MHC class I, and MHC class II. For in vitro proliferation assays, purified SIINFEKL ovalbumin peptide—specific OT-I CD8+(MHC class 1 restricted) or OT-II CD4+ T-cells (MHC class II restricted) were suspended at 107 cells/mL and labelled with CFSE (5 µM, Life Technologies) for 10 min. After one wash, T-cells and B-cells were plated at a 1:0.8 ratio in 200 µL of T-cell media in a 96-well U-bottom plate. CpG B, CpG C, or LPS was added to the appropriate wells, and anti-CD3/CD28 Dynabeads (Life Technologies) were added to positive control wells at 1 bead/T-cell. Supernatant collection for cytokine analysis and flow cytometry to assess T-cell proliferation were performed on day 2 and day 4.

In vivo proliferation assay. On day −1, 106 OT-I Thy1.1 CD8+resting T-cells labelled with CFSE (5 µM) were injected retro-orbitally (r.o.) into C57BL/6 mice. The next day (day 0), animals were injected r.o. with 1-3 million CD45.1+B-cells that had been loaded with OVA using the microfluidics SQZ device the previous day and incubated overnight with 5 µM CpG B, or were loaded with OVA by mechano-disruption just prior to injection and not exposed to any TLR ligand. Animals were necropsied on day 4 and their spleens, inguinal lymph nodes, and cervical lymph nodes were harvested. The organs were mashed through a cell strainer. Single-cell suspensions were incubated with mouse anti-CD16/CD32 (eBioscience) to reduce nonspecific antibody binding, and were stained with anti-CD8-APC, anti-B220-PE-Cy7, anti-CD45.1-PerCP-Cy5.5, and anti-Thy1.1-APC-Cy7. Flow cytometry to determine cell numbers and/or CFSE dilution was performed using known methods.

Mechano-Disruption (Microfluidic Cell Squeezing) Enables Rapid and Efficient Delivery of Macromolecules The process of mechano-disruption for loading B-cells with antigen was accomplished using the device described herein. Live cells were passed through parallel microfluidic channels in a silicon device; in each channel, 1 or more constrictions create transient pores or perturbations in the membranes of cells passing through the device. Macromolecular cargos present in the surrounding fluid diffuse into the cell during this transient perturbation/membrane disruption, leading to intracellular loading. Mechano-disruption is effective for promoting cytosolic delivery of macromolecules into a wide variety of cell types including primary murine B-cells; efficient delivery was achieved with 5 sequential constrictions with dimensions 30 µm length and 5 µm width. Device design can be altered (increased number of parallel constriction channels to 75, longer entry region, reversibility, etc.) prompted to customize mechano-disruption parameters for protein delivery into B-cells and subsequent antigen presentation. Pilot optimization experiments showed that 30-4×1 microfluidics chips (1 constriction per channel that is 30 µm long and 4 µm in diameter) run at 120 psi were effective chip design for mechano-disruption of murine B-cells with both efficient delivery and high cell viability at concentrate ions of $5 \times 10^6$ B-cells/mL. Other configurations are described herein, e.g., 30-5×5 vs. 30-4×1. Cells at this pressure ran through a device at a rate of approximately 1 million cells per second. Microfluidic squeezing promoted greatly enhanced dextran uptake compared to endocytosis, with internalization increased ~65-fold and ~25-fold for 3 and 40 kDa dextrans, respectively. This represented delivery to 75-90% of all cells for both dextrans; by comparison less than 10% of resting B-cells endocytosed detectable amounts of cargo. Viability of recovered cells after mechano-disruption was ~95%, similar to endocytosis controls. The capacity for the maximum number of cells that can be passed through these disposable microfluidic chips ranged from 1-5 million cells per device; however, devices were run with multiple aliquots of cells (1 million cells per run) until clogged, and the maximum number of cells run through each individual device in a given experiment was often in significant excess of 5 million cells. There was low variability in percentage of delivered cells from first run to clogging of devices, indicating that intra-device variability was minimal. Delivery performance of multiple devices within the same experimental session (inter-device variability) was very consistent. Recognizing that some applications may require higher numbers of B-cells, the efficacy of the microfluidic devices at different cell densities. The efficiency of intracellular dextran delivery was largely independent from cell concentration up to at least $50 \times 10^6$ cells per mL, indicating potential for robust scalability.

Figure 30:
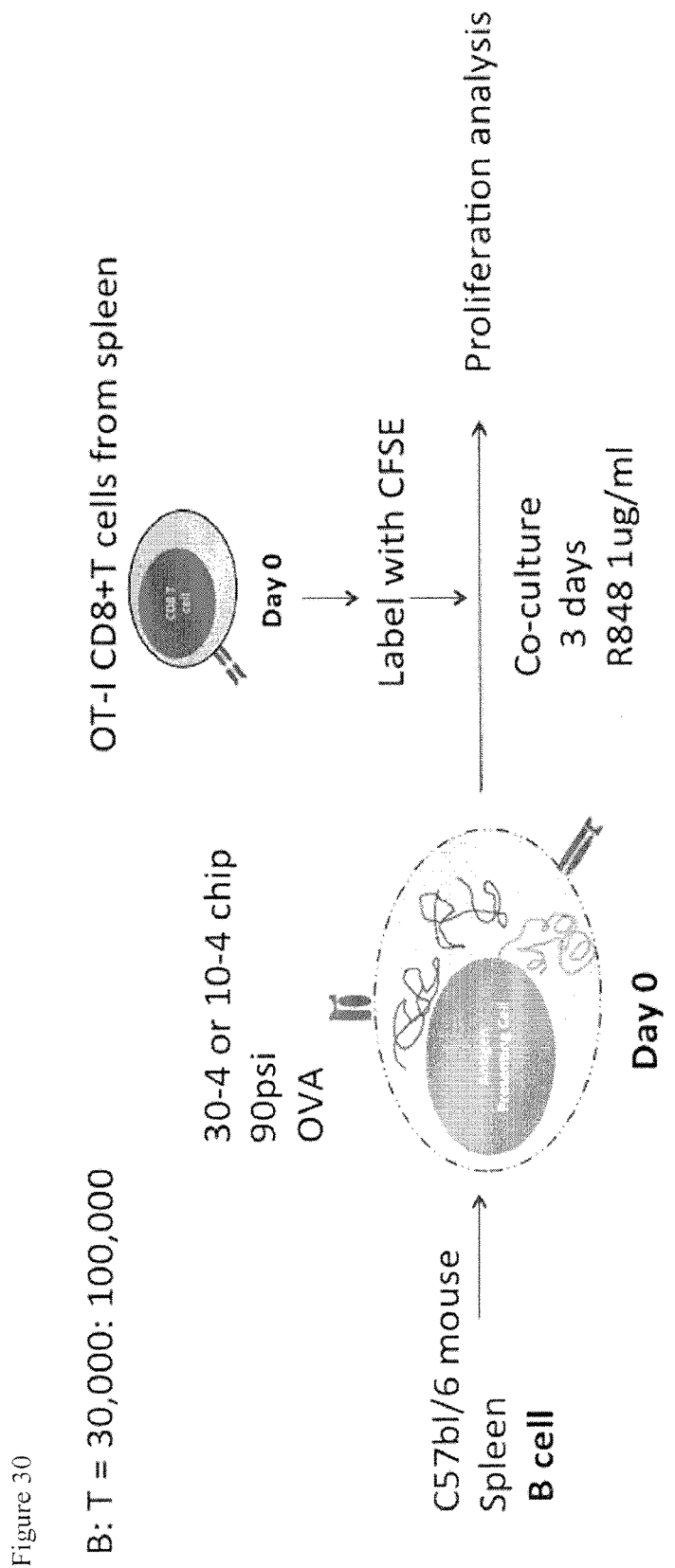
FIG. 30 is a schematic of an exemplary procedure for making and characterizing squeeze-mediated production of B cells as antigen presenting cells.
Figure 31:
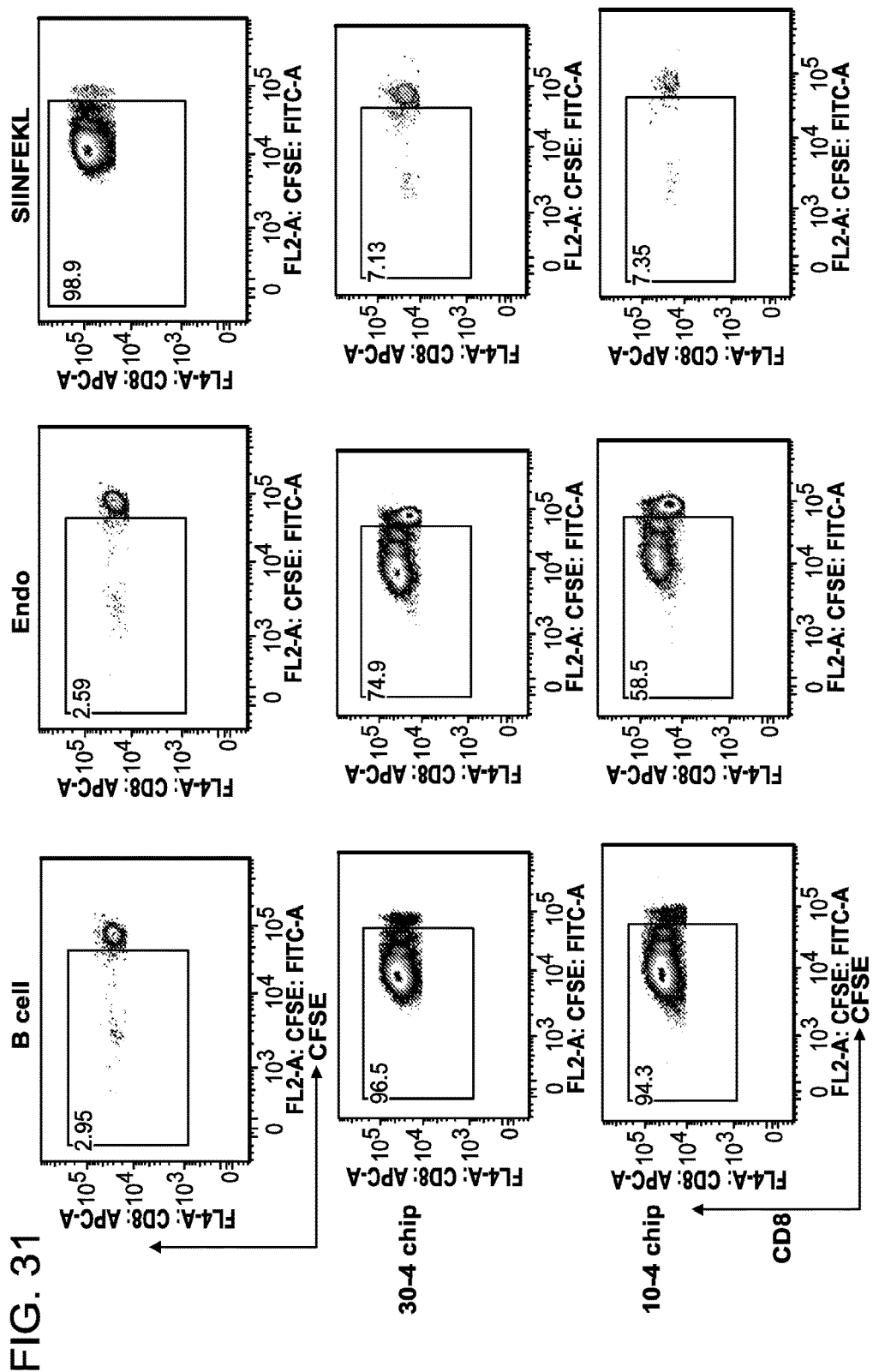
FIG. 31 is a series of histograms showing that cell-squeezed B cells induced potent CD8+ T cell proliferation.
Figure 32:
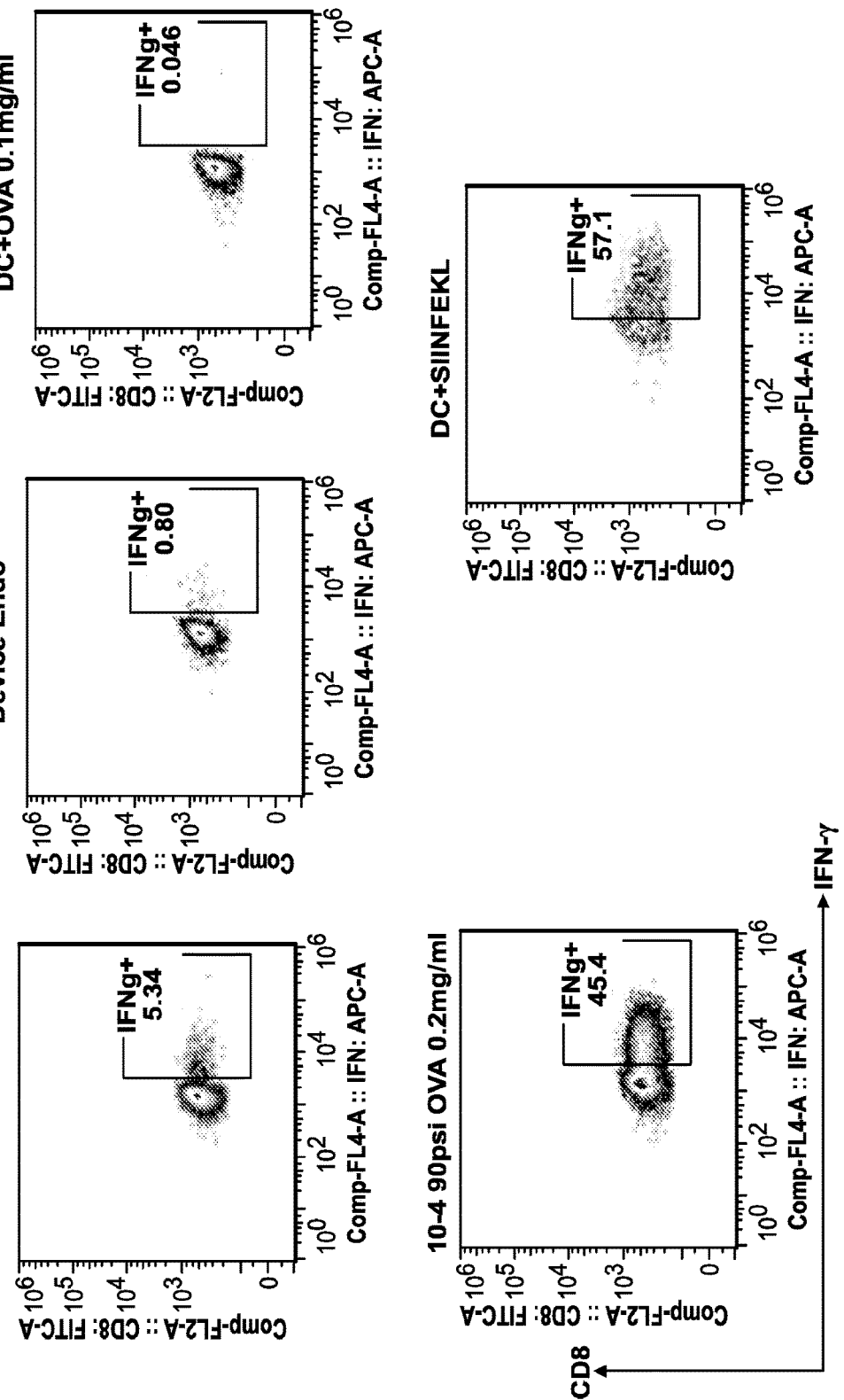
FIG. 32 is a series of histograms showing that cell-squeezed dendritic cells (OVA delivered) secrete gamma interferon.

A schematic showing B cells treated to function as enhanced antigen presenting cells is shown in FIG. 30.

Polyclonal B-Cells Squeezed with Whole Protein Expand Antigen-Specific CD8+ T-Cells that Secrete Effector Cytokines In Vitro To determine whether mechano-disruption can facilitate protein delivery to the cytosolic class 1 MHC antigen processing and presentation machinery, we utilized the optimal conditions described above to deliver the model protein ovalbumin (OVA) into resting, purified polyclonal B-cells, by passing cells through microfluidic device in the presence of excess OVA in the surrounding medium. Squeezed B-cells were then co-cultured with CFSE-labelled OT-I CD8+ T-cells, which bear a transgenic T-cell receptor specific for the MHC class I-restricted OVA peptide SIINFEKL, in the presence or absence of CpG as a B-cell-activating stimulus. CFSE dilution in OT-I T-cells was analysed by flow cytometry to assess proliferation/expansion of the T-cells in response to B-cell-presented antigen. Whole protein delivery to B-cells by cell squeezing was found to enable robust MHC class I antigen presentation and antigen-specific CD8+ T-cell priming in vitro. Cell squeezing as described herein primarily directs antigen to the cytosol and not endosomal compartments where MHC class II loading occurs. Consistent with this, the data indicated that neither resting nor CpG-activated mechano-porated B-cells were able to expand OVA-specific OT-II CD4+ T-cells after 4 days of co-culture. The functionality of B-cell-primed CD8+ T-cell populations was assayed by measuring secretion of effector molecules at days 2 and 4 of co-cultures. B-cells loaded with antigen by squeezing, whether resting or activated, primed T-cells to secrete substantial quantities of granzyme B, IFN-γ, and TNF-α, while B-cells loaded with antigen by endocytosis produced basal levels of cytokines.

Squeezed B-Cells Prime Antigen-Specific CD8+ T-Cells In Vivo

In addition an in vitro antigen-specific T-cell expansion platform, B-cells processed as described are useful as an alternative to dendritic cells for use as cellular vaccines. To evaluate in vivo performance, CFSE-labelled OT-I CD8+ T-cells expressing Thy1.1 as a congenic marker were adoptively transferred into recipient mice as reporters of antigen presentation. One day later, resting B-cells were injected immediately after mechano-disruption-mediated antigen loading, or mechano-disruption-loaded B-cells that were subsequently activated for 24 h with CpG in vitro were injected. Resting B-cells loaded with antigen by endocytosis were used as controls, either immediately or after 24 h of activation with CpG. Four days after B-cell transfer, mice were sacrificed and spleens and inguinal lymph nodes were analysed for OT-I proliferation by flow cytometry. Consistent with in vitro results, mechano-porated B-cells were able to elicit division of adoptively transferred OT-I T-cells while endocytosis controls showed only basal division. Both CpG-activated and resting squeezed B-cells caused OT-I proliferation in spleens (~45% and ~35% divided of injected OT-I T-cells with p<0.001 and p=0.001 comparing SQZ vs. endocytosis, respectively). CpG-activated and resting squeezed B-cells also elicited similarly enhanced OT-I proliferation in lymph nodes compared to endocytosis B-cells (~40% and ~35% divided of injected OT-I T-cells by CpG B and resting squeezed B-cells, respectively; p<0.001 comparing SQZ vs. endocytosis for both resting and CpG). Endocytosis controls showed ~4% baseline division in lymph nodes. These results indicated that B-cells loaded by microfluidic mechano-disruption are useful in cellular vaccines.

Figure 29:
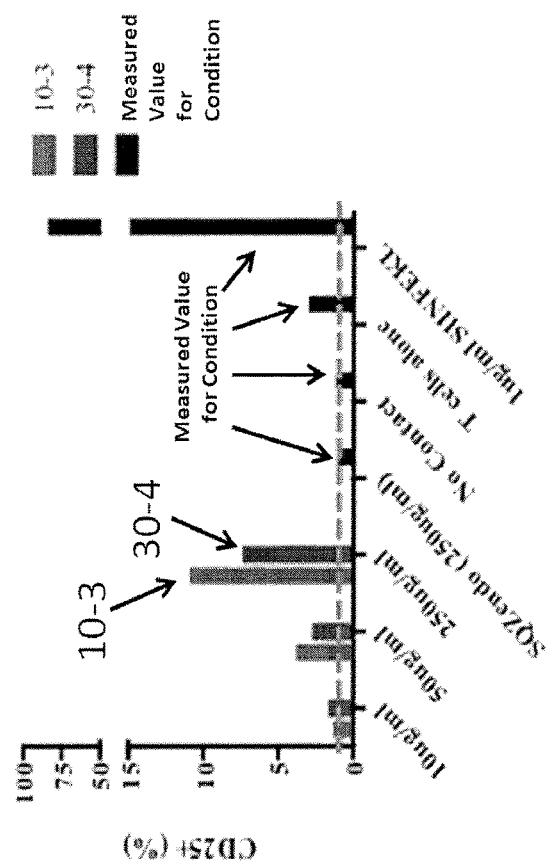
FIG. 29 is a bar graph demonstrating the use of mouse T cells as antigen presenting cells. The T cells, which were treated by cell squeezing to load unprocessed ovalbumin antigen, were cultured with OT-1 (SIINFEKL-specific T cell line) and activation markers, CD25 and CD69 evaluated.
Figure 29:
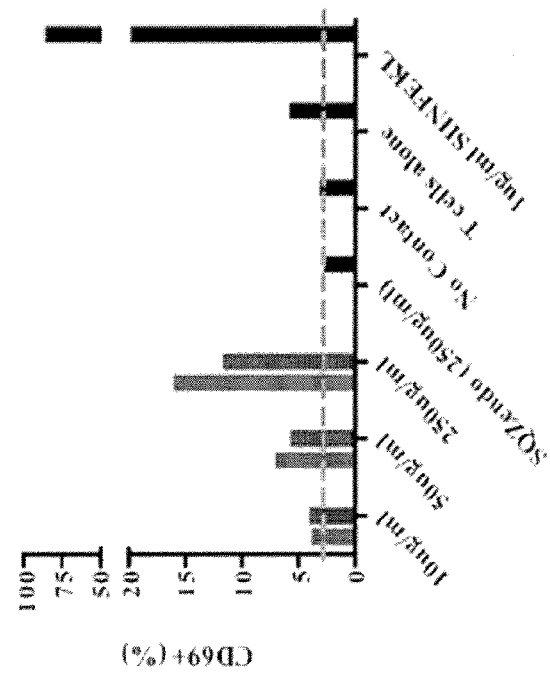

The results were further confirmed by experiments evaluating the activation status of responding CD8+ T cells (FIG. 29).

B-cells loaded with specific antigens as described here are therefore useful as APCs for cell-based vaccines and as autologous reagents for expansion of antigen-specific T-cells, with significant advantages over dendritic cells, especially with respect to their ready availability in large numbers from peripheral blood and their ability to be further expanded substantially in culture. Prior to the invention, methods for efficient antigen loading in B-cells, especially for class I MEW presentation, have been a major barrier to development of polyclonal B-cells as APCs for in vitro or in vivo use. The devices and methods described herein represent a simple approach using microfluidic-based mechanical deformation and passive diffusion leading to robust loading of protein antigens directly to the cytosol of resting or activated B-cells and to MHC class I presentation of peptides derived from native whole protein. The advantages conferred by mechano-disruption are numerous, including delivery of native proteins without processing, engineering, or modification, the rapid nature of the process, the relatively high efficiency of delivery and functional outcomes, and the ability to deliver material to resting cells decoupled from cellular biology such as programming stimulus or receptor targeting.

The ability to deliver whole native protein or polypeptides directly to the cytosol for processing and MHC class I presentation enables unbiased presentation of multiple peptides following native antigen processing. The microfluidic cell squeezing device also enables delivery of mixtures of proteins, including tumor lysates, e.g., tumor biopsy lysates, or other complex protein sources. The foregoing demonstration that proteins were delivered for MHC class I processing independently of cell activation status is a major advantage of this approach, and the approach enables decoupling of protein loading and cellular programming, facilitating independent modulation of each component.

An exemplary design contains 75 parallel constriction channels; however, increases in the number of channels or operating multiple devices in parallel dramatically improves throughput. The ease of use and rapid processing enabled by this approach (e.g., ~1×10$^6$ cells/s rate flow through device, <2 h for total experiment time) provides benefits for clinical translation such as reduction in time and resources required for preparation of cell-based therapeutics.

Using B-cells as APCs, the amount of patient blood required to prepare a single-dose cellular vaccine is vastly reduced compared to DC-based approaches. Time required for protein loading by cellular uptake processes such as endocytosis or pinocytosis is avoided. The results in vitro demonstrated significant potential for B-APCs as an alternative platform for expansion of effector CTLs and the squeezed B-cells also functioned as effective APCs in vivo. The methods are also useful to co-load both MHC class I and class II antigen presentation pathways to generate CD4+ T-cell help.

Class I-Restricted Antigen Processing and Presentation by B Cells

Thus, B-cells were processed by cell squeezing to yield autologous antigen-presenting cells (APCs) to prime antigen-specific T-cells both in vitro and in vivo. This microscale cell squeezing process creates transient perturbations or pores in the plasma membrane, enabling intracellular delivery of whole proteins from the surrounding medium into B-cells via mechano-disruption. Both resting and activated B-cells process and present antigens delivered via mechano-disruption exclusively to antigen-specific CD8+ T-cells, and not CD4+ T-cells. Squeezed B-cells primed and expanded large numbers of effector CD8+ T-cells in vitro that produced effector cytokines critical to cytolytic function, including granzyme B and interferon-γ. The squeezed antigen-loaded B-cells were also able to prime antigen-specific CD8+ T-cells in vivo when adoptively transferred into mice. These data demonstrate that mechano-disruption/membrane perturbation is a useful and highly efficient method for B-cell antigen loading, priming of antigen-specific CD8+ T-cells, and decoupling of antigen uptake from B-cell activation.

T Cells as Antigen Presenting Cells for Immune Stimulation or Tolerance

Prior to the invention, antigen presentation for the purposes of immune stimulation or tolerance was generally assumed to be the purview of a select subset of cells referred to as antigen presenting cells, e.g., B cells, dendritic cells and macrophages, and did not include T cells, because they were assumed to lack the necessary machinery to process and present antigens in a context that would facilitate immune stimulation or tolerance. The devices and squeeze-mediated antigen loading of cells led to a surprising discovery that delivering antigenic proteins directly to the cytosol of T cells confers onto such processed cells an antigen presentation phenotype.

The methods modulate T cell immune responses in vivo in a manner that had not been reported previously. A model antigen, ovalbumin, was delivered to murine primary T cells using the Cellsqueeze device platform, and the cells were injected into hosts to measure CD8+ T cell responses. The antigen loaded T cells were capable of generating a substantial CD8+ T cell responses as measured by flow cytometry, indicating that T cells loaded with antigens by an external mechanism, e.g., cell squeezing, can indeed present epitopes on their surface, communicate with other T cells, and generate a measurable immune response. This response was significantly greater than controls and was comparable to responses observed in experiments using professional APCs such as dendritic cells.

This finding was unexpected and is of great significance to the field of immunology and immunotherapy as it demonstrates the use of T cells as effective antigen presenters for therapeutic and research applications. Prior to the invention, DCs were the only cell widely accepted for this use, and as is described above, the cell-squeeze approach is useful for rapid, efficient, and greatly-enhance production of B cells for this purpose. Because T cells are more abundant and accessible than DCs, they provide greater clinical efficacy and facilitate broader impact for currently expensive, difficult to produce cellular vaccine applications. Thus, a T cell can now be used as an antigen presenting cell for presentation for any type of antigen, purpose (tolerogenic vs. immunostimulatory), routes of injection, for clinical as well as research applications.

Mouse T cells treated with whole, unprocessed antigen using the cell-squeeze method function as antigen presenting cells (FIG. 29). Murine T cells were isolated from mouse spleens and OVA was delivered to the T cells in RPMI at OVA concentrations of (250, 50, 10 ug/ml OVA) using the exemplary 10-3 and 30-4 device configurations. These T cells were then cultured with OT-1 T cells (SIINFEKL peptide epitope-specific) and activation markers CD25 and CD69 were assessed. The results demonstrate that T cells into which whole, unprocessed antigen, e.g., full-length ovalbumin, was cytosolically delivered using cell-squeezing surprisingly and effective function to present antigen to and activate epitope-specific effector CD8+ T cells.

Figure 28A:
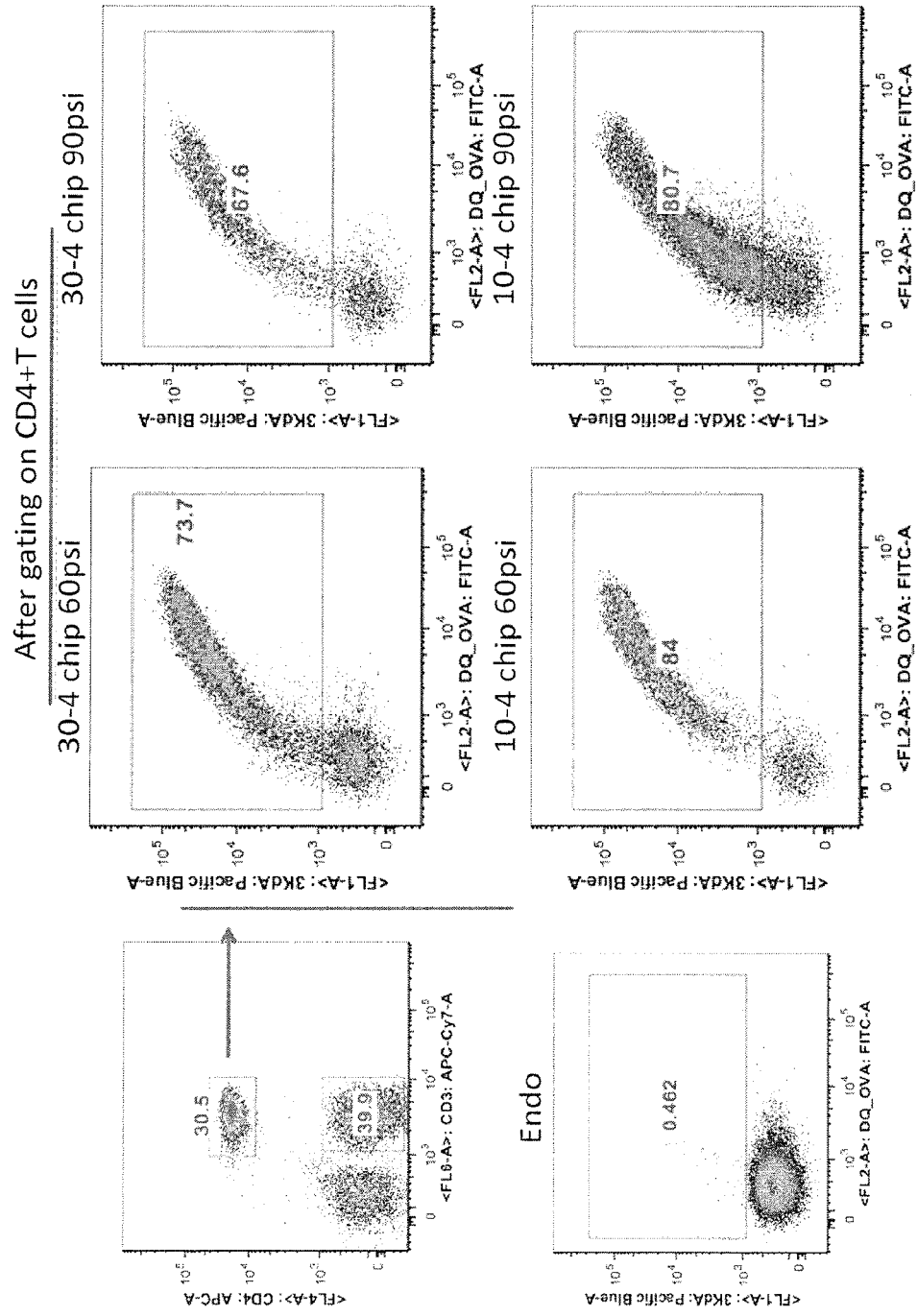
FIGS. 28A-B are histograms showing gating on both of DQ-OVA+3 kDa-Dextran+ T cells.
Figure 28B:
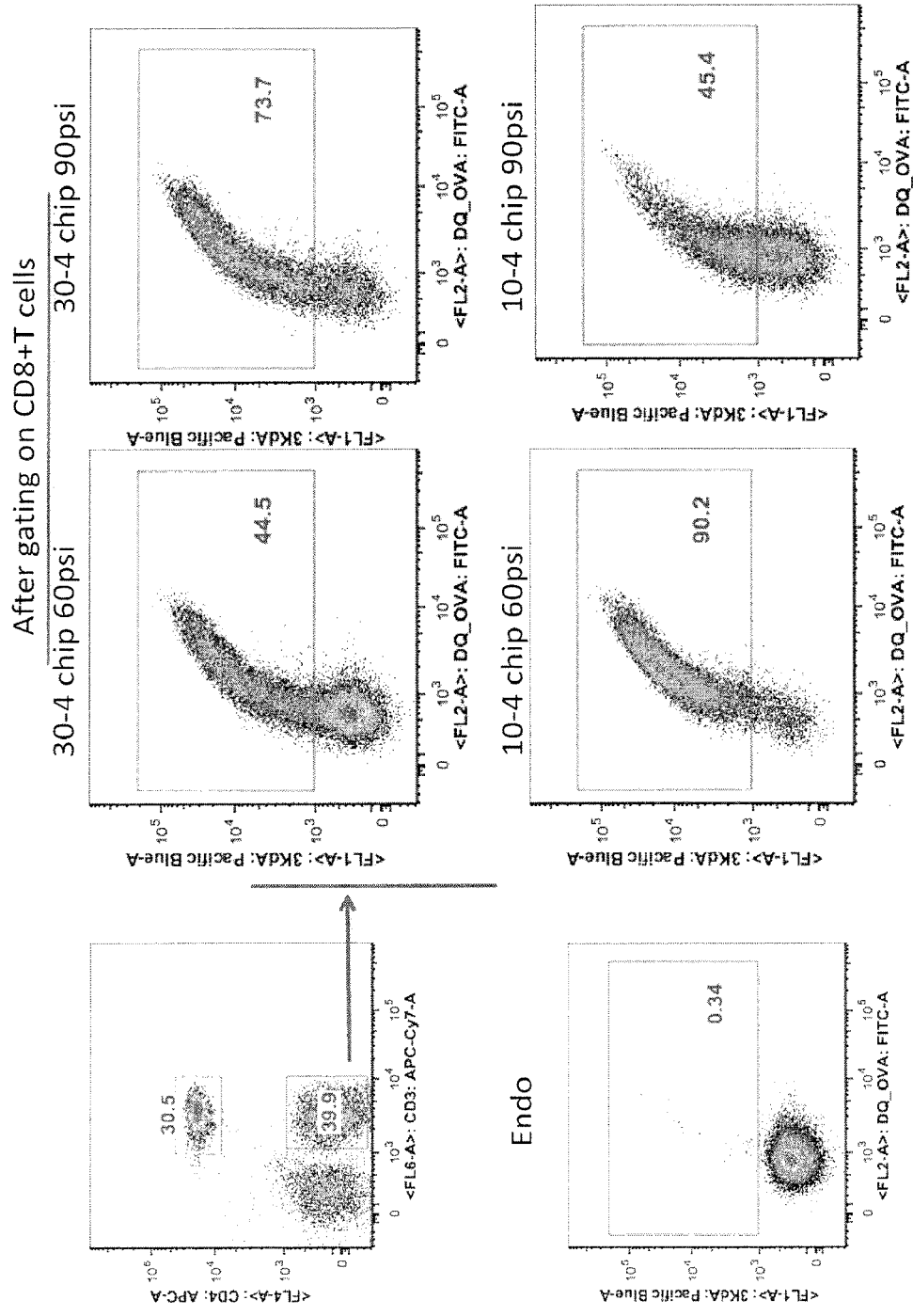

Additional data demonstrate the delivery of DQ-Ova (DQ™ ovalbumin, Catalog # D-12053, Molecular Probes, Inc.) to primary human T cells isolated from blood (FIGS. 28A and B). The DQ ova is a chemically conjugated version of ovalbumin protein that fluoresces on the FITC channel if the protein is processed but will not fluoresce if the protein was not processed by the cell. Thus, the appearance of a FITC signal for the device-treated cases indicates that the cells were processed the DQ-Ova antigen, further supporting the observation that the manufacturing antigen-presenting T cells (T cells as APCs) function in a human system in addition to mouse system described above. In some experiments, 3 kDa Dextran dye that fluoresces on the pacific blue channel was co-delivered. Results show differences in Ova processing between CD4 and CD8 T cells and a dramatic improvement relative to the endocytosis control. These data indicate that antigen processing is carried out by human T cells when the antigen is delivered directly to the cytosol of the Tcell. Data showing that the DQ¬Ova antigen changes its fluorescence properties show that the antigen is being processed in human T cells and therefore presented by histocompatibility antigens to T effector cells.

Figure 26:
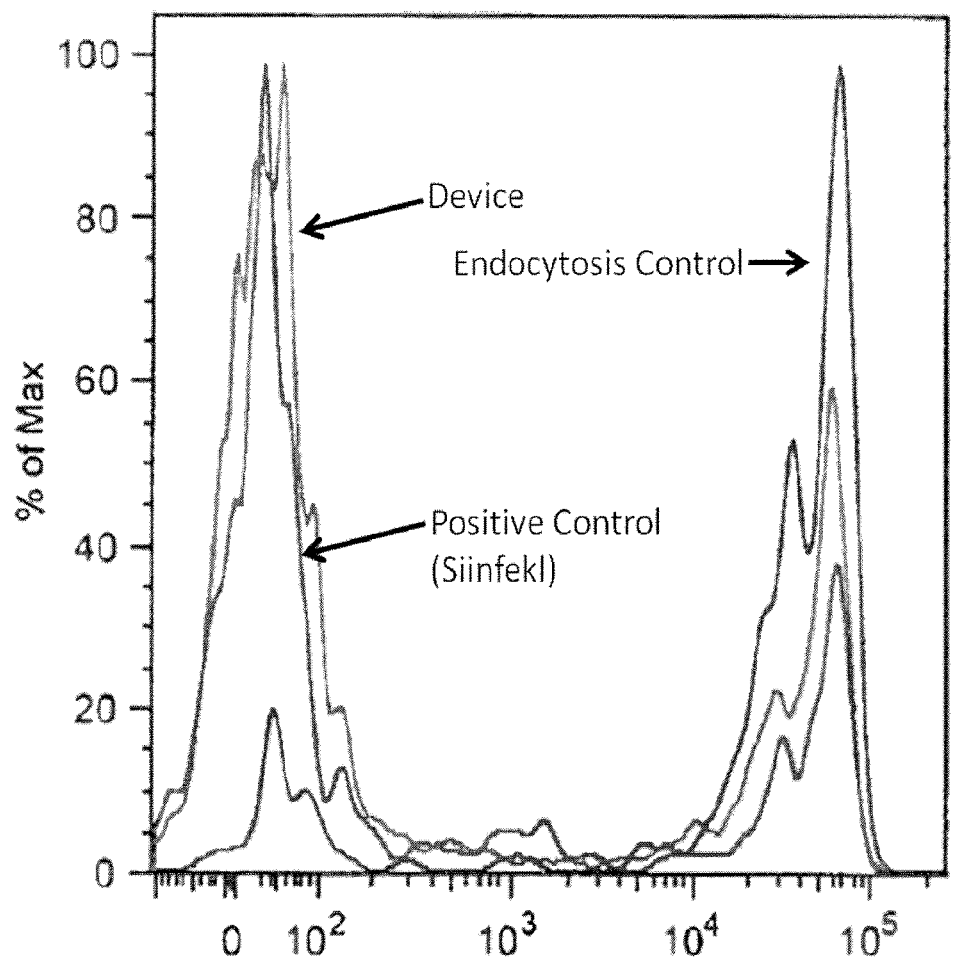
FIG. 26 is a graph showing the results of a CFSE proliferation assay in vivo: This graph is measuring the proliferation of antigen specific CD8 T cells. As the CD8T cells are activated and proliferate in the mouse they dilute the CFSE dye and have a lower fluorescence intensity. In this case, donor T cells treated by the device or the positive control yielded much greater activation and proliferation of CD8 T cells in the recipient mouse. Endocytosis controls by contrast show minimal effect.

Activation of epitope-specific T cells was also demonstrated in vivo. FIG. 26 shows the results of a CFSE proliferation assay in vivo (the proliferation of antigen specific CD8+ T cells). As the CD8T cells are activated and proliferate in the mouse, they dilute the CFSE dye and have a lower fluorescence intensity. In this case, donor T cells treated by the device or the positive control yielded significantly greater activation and proliferation of CD8 T cells in the recipient mouse. Endocytosis controls by contrast show minimal effect.

Figure 27:
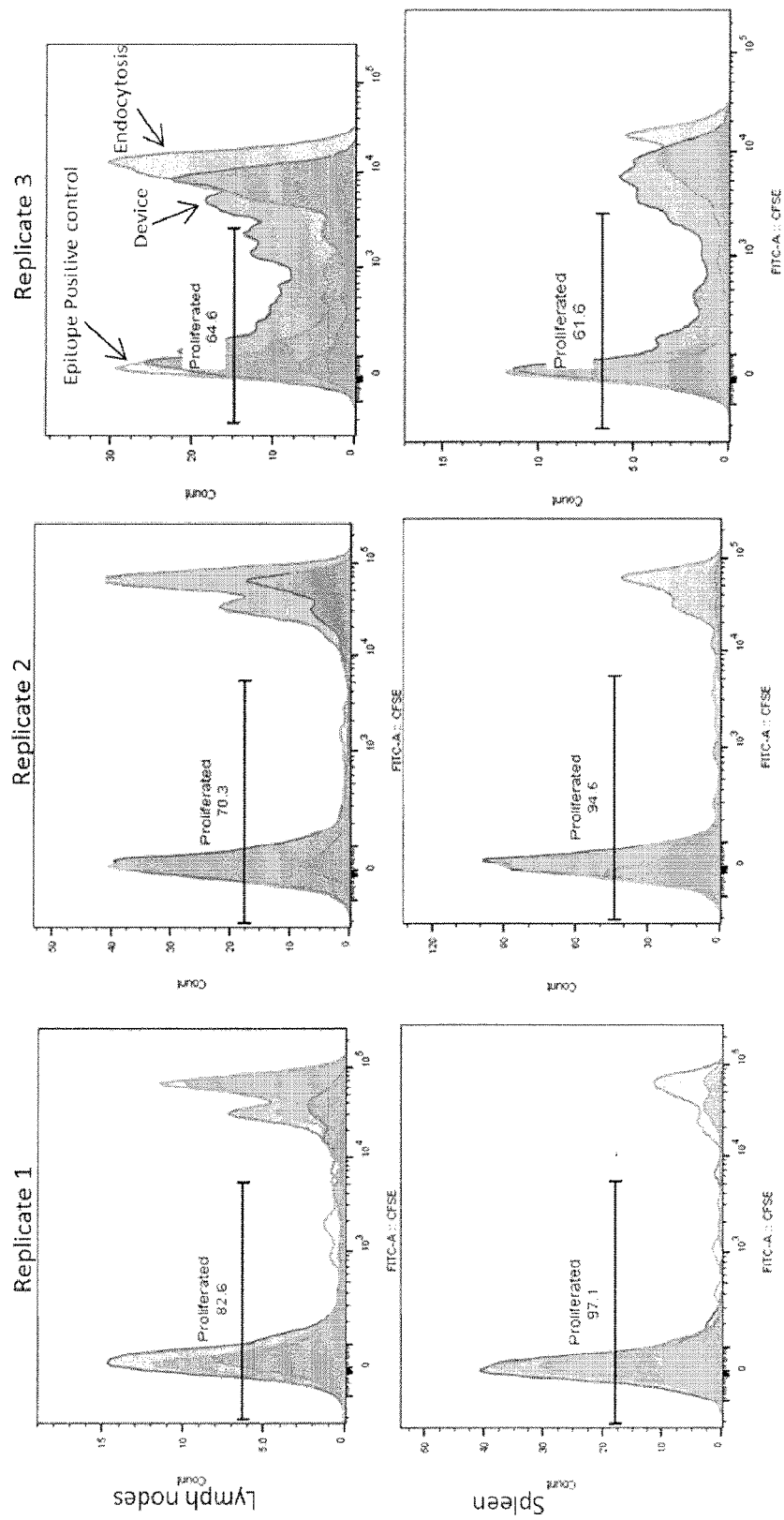
FIG. 27 is a series of histograms showing proliferation of antigen specific OT-I T cells in mice in response to vaccination with antigen treated wild type T cells. T cell proliferation responses are measured by CFSE staining, the stain is diluted as the cells proliferate. Lower intensities indicate greater responses, higher intensity peaks indicate no/less response. Each column represents a replicate of the experiment with the lymph nodes and spleen derived from the same mouse. Each column of experiments involved 3 mice (9 mice in total).

Proliferation of antigen specific OT-I T cells in mice in response to vaccination with antigen treated wild type T cells was also demonstrated in vivo (FIG. 27). T cell proliferation responses were measured by CFSE staining. The stain is diluted as the cells proliferate; thus, lower intensities indicate greater responses, higher intensity peaks indicate no/less response. Each column represents a replicate of the experiment with the lymph nodes and spleen derived from the same mouse. Each column of experiments involved 3 mice (n=9 mice in total).

The materials and methods described below were used to generate data pertaining to T cells as Antigen Presenting Cells for Immune Stimulation or Tolerance described above. Experimental Timeline. The following experimental timeline was used:

Day 0: Inject CFSE/CellTraceViolet labeled OT-1 CD45.1 T cells into naïve B6 hosts
Day 1: Deliver antigen to T cell APCS (Tc-APCs), inject Tc-APCs and control APCs into B6 hosts
Day 5/6: Harvest spleens and lymph nodes from immunized mice, analyze T cell proliferation via flow cytometry T cell isolation (for adoptive transfer). Materials: 100 urn Falcon cell strainer; 70 µm Falcon cell strainer; Ammonium-Chloride-Potassium (ACK) lysis buffer; CD8a+ T cell isolation kit (Miltenyi Biotec); MACS cell separation column. T cell media (RPMI with 10% FBS, pen strep, 1× sodium pyruvate, 50 uM b-mercaptoethanol); MACS buffer (0.5% BSA, 2 mM EDTA in PBS). Methods: Spleens and skin draining lymph nodes were harvested from OT-1 CD45.1 Rag 2-/- mice on a C57BL/6J background and mashed through a wet 100 µm cell strainer into a 50 mL Falcon tube. Filters were washed with MACS buffer, then spun down at 500 rcf for 4 minutes. Supernatants were aspirated, followed by the addition of 3 mL of ACK lysis buffer to lyse red blood cells. Reactions were quenched with 12 mL of MACS buffer, then spun down at 500 ref for 4 minutes. Cell pellet was resuspended in 40 uL MACS buffer per $1 \times 10^7$ cells, then filtered through a 70 µm cell strainer into a 50 mL Falcon tube. 10 uL of CD8a+ T cell antibody cocktail were added per $1 \times 10^7$ cells and incubated for 10 minutes over ice. 30 uL MACS buffer per $1 \times 10^7$ cells were added, then 20 uL of streptavidin beads were added per $1 \times 10^7$ cells and incubated over ice for 15 minutes. Cells were spun down at 800 rcf for 5 minutes and supernatant was aspirated, then resuspended in 3 mL MACS buffer. Cell separation column was prepared by passing through 3 mL of MACS buffer, followed by 3 mL of cell suspension over a 70 µm cell strainer, into a 15 mL Falcon tube. Column was washed 3× with 3 mL MACS buffer, pooled flowthrough was spun down at 500 rcf for 4 minutes. Supernatant was aspirated and enriched CD8+ T cells were suspended in T cell media. >90% purity was checked by staining for CD8a and analysis on flow cytometry.

CellTrace Violet/CFSE Labeling. Materials: CFSE in DMSO (Life Technologies, Grand Island, N.Y.); CellTrace Violet in DMSO (Life Technologies, Grand Island, N.Y.); Purified OT-I CD45.1 CD8+ T cells; Sterile PBS; Sterile fetal bovine serum. Methods: OT-1 CD45.1 CD8+ T cells were enriched as described above and suspended in 2.5 mL of warm PBS in a 15 mL Falcon tube. CellTrace Violet or CFSE in DMSO was dissolved in warm PBS at 10 uM, then 2.5 mL was added to cell suspension (5 uM final concentration). Cells were left in a 37° C. warm water bath for 10 minutes, then 7 mL of PBS was added to quench reaction. 2 mL of FBS was layered to the bottom using a sterile glass pipette, then spun down at 500 ref for 4 minutes. Supernatent was aspirated and cells were washed again in 10 mL of PBS, then spun down at 500 rcf and resuspended at $2 \times 10^7$ cells per 100 ul PBS.

T cell isolation (as Tc-APCs). Materials: 100 um Falcon cell strainer; 70 um Falcon cell strainer; ACK lysis buffer; Pan T cell isolation kit (Miltenyi Biotec, San Diego, Calif.); MACS cell separation column; T cell media (RPMI with 10% FBS, pen-strep, lx sodium pyruvate, 50 uM b-mercaptoethanol); MACS buffer (0.5% BSA, 2 mM EDTA in PBS). Methods: Spleens and skin draining lymph nodes were harvested from C57BL/61 mice and mashed through a wet 100 µm cell strainer into a 50 mL Falcon tube. Filters were washed with MACS buffer, then spun down at 500 rcf for 4 minutes. Supernatants were aspirated, followed by the addition of 3 mL of ACK lysis buffer to lyse red blood cells. Reactions were quenched with 12 mL of MACS buffer, then spun down at 500 rcf for 4 minutes. Cell pellet was resuspended in 40 uL MACS buffer per $1\times10^7$ cells, then filtered through a 70 urn cell strainer into a 50 mL Falcon tube. 20 uL of Pan T cell antibody cocktail were added per $1\times10^7$ cells and incubated for 10 minutes over ice. 30 uL MACS buffer per $1\times10^7$ cells were added, then 20 uL of streptavidin beads were added per $1\times10^7$ cells and incubated over ice for 15 minutes. Cells were spun down at 800 rcf for 5 minutes and supernatant was aspirated, then resuspended in 3 mL MACS buffer. Cell separation column was prepared by passing through 3 mL of MACS buffer, followed by 3 mL of cell suspension over a 70 μm cell strainer, into a 15 mL Falcon tube. Column was washed 3× with 3 mL MACS buffer, pooled flowthrough was spun down at 500 rcf for 4 minutes. Supernatant was aspirated and enriched T cells were suspended in T cell media. >90% purity was checked by staining for CD3e and analysis on flow cytometry.

T cell antigen delivery and activation in vitro. Materials: Purified T cells; CellSqueeze 30-4 chips; CellSqueeze device; Lipolysaccharide (LPS); T cell media (RPMI with 10% FBS, pen-strep, lx sodium pyruvate, 50 uM b-mercaptoethanol); OVA protein; SIINFEKL peptide. Methods: Purified T cells were incubated in T cell media with 1 ug/mL LPS for 30 minutes over ice. T cells were washed 2× in T cell media and spun down at 500 rcf for 4 minutes, then incubated with either 0.01 mg/mL-0.1 mg/ml OVA or 1 ug/mL SIINFEKL over ice. CellSqueeze apparatus was assembled according to standard protocol with the 30-4 chip, then 200 uL of T cell media was run through each chip at 100 PSI. Half of the T cells were passed through CellSqueeze device at 100 PSI and the other half were left over ice (endocytosis case). Flowthrough was collected in a 96 well plate and left over ice for 15 minutes for cell membranes to repair. Cells were spun down at 350 RCF for 10 minutes and supernatants were flicked. Cells were reactivated in 1 ug/mL LPS for 10 minutes prior to injection into hosts.

Enrichment of Patient Immune Cells

Cell squeezing is also useful to enrich or expand patient-derived immune cells ex vivo for subsequent transfer back into the patient. For example, antigen is delivered via mechano-disruption to the cytosol of antigen presenting cells (dendritic cells, B cells, T cells, macrophages). These antigen presenting cells process and present the processed antigen in the context of MHC/HLA heterodimers on their surface to stimulate and expand T cells. The expanded populations of T cells are then re-infused in the patient to augment a therapeutic immune response. For example, the antigen is a tumor antigen (or lysate) to augment an anti-tumor response. Alternatively, the antigen or a bacterial or viral antigen (or fragments thereof or attenuated or killed bacterial cells or viral particles) to augment microbial infectious diseases. In another example, the antigen is a self-antigen presented together with a tolerogen (as described) above) to tolerize and then expand a population of tolerized immune cells for re-infusion back into the patient to down-regulate an aberrant, e.g., auto-immune, response.

Use of T Cells as Antigen Presenting Cells

Cancer immunotherapy based on the activation of a patient's T cells using antibody therapeutics has shown success in those indications with high frequencies of mutations and with pre-existing T cell responses to tumor associated antigens (TAA)(Topalian et al., *Cancer Cell* 2015; 27: 450-461; Hodi et al., *N Engl J Med* 2010; 363: 711-723; Topalian et al., *Cell* 2015; 161: 185-186). Because many cancers have low frequencies of mutations and low rates of spontaneous T cell responses, the use of cancer vaccines may serve to boost T-cell responses to TAA (Melief et al., *J Clin Invest* 2015; 125: 3401-3412). Cancer vaccines have the potential to be used as a monotherapy (Ly et al., *Cancer Res* 2010; 70: 8339-8346; Kantoff et al., *N Engl J Med* 2010; 363: 411-422), in combination with checkpoint blockade therapy (Agarwalla et al. *J Immunother* 2012; 35: 385-389) or, in combination with adoptive T-cell therapy (Lou et al., *Cancer Res* 2004; 64: 6783-6790).

In the preclinical setting, strategies using professional antigen presenting cells (APC) for cancer vaccination have demonstrated that antigen-pulsed dendritic cells (DC) can generate protective immunity against tumors (Celluzzi et al., *J Exp Med* 1996; 183: 283-287; Mayordomo et al., *Nat Med* 1995; 1: 1297-1302; 7489412; Flamand et al., *Eur J Immunol* 1994; 24: 605-610). Clinical studies performed in various types of cancer (Nestle et al., *Nat Med* 1998; 4: 328-332; Hu et al., *Cancer Res* 1996; 56: 2479-2483; Hsu et al., *Nat Med* 1996; 2: 52-58; Reichardt et al., *Blood* 1999; 93: 2411-2419; Morse et al., *Clin Cancer Res* 1999; 5: 1331-1338; Yu et al., *Cancer Res* 2001; 61: 842-847) suggest that monocyte-derived DCs are capable of eliciting antigen-specific immunity in humans, however the clinical responses are low. For example, the first FDA approved DC-based cancer vaccine (Sipuleucel-T, Provenge, Dendreon, Seattle, Wash.) demonstrated four months prolonged survival in patients with hormone-refractory prostate cancer (Kantoff et al., *N Engl J Med* 2010; 363: 411-422; Higano et al., *Cancer* 2009; 115: 3670-3679). Among the hypotheses to explain why this vaccine has such low clinical benefit, the procedure used to load the Sipuleucel-T DCs with antigen, may have resulted primarily in MEW Class II antigen presentation as opposed to having both MHC Class I and II presentation. As such, low cytotoxic T cell activity may have had a role in the poor efficacy of this product.

Methods developed for delivery of TAA to DCs utilize the CellSqueeze platform for optimal antigen presentation on both MHC Class I and II histocompatibility molecules. By addressing the limitations of existing antigen loading techniques, the methods described herein lead to more powerful cytotoxic and helper T cell responses in vivo. The platform includes a microfluidic chip capable of rapidly deforming cells as they pass through a constriction to temporarily disrupt their membrane and enable transport of the target material to the cell cytoplasm. By eliminating the need for electrical fields or exogenous enhancers or carrier materials, the methods described minimizes the potential for cell toxicity and off-target effects.

Targeting Viral or Neo Antigens

Since central tolerance can be induced to self antigens, therapeutic vaccinations are now preferably targeting neo (Gubin et al., *J Clin Invest* 2015; 125: 3413-3421; Gubin et al., *Nature* 2014; 515: 577-581; Yadav et al., *Nature* 2014; 515: 572-576; Quakkelaar et al., *Adv Immunol* 2012; 114: 77-106; Castle et al., *Cancer Res* 2012; 72: 1081-1091) and viral antigens (Melief et al., *J Clin Invest* 2015; 125: 3401-3412; Quakkelaar et al., *Adv Immunol* 2012; 114: 77-106).

To identify and evaluate antigens, a cocktail of nine synthetic long overlapping peptides (SLP) of the oncogenes E6 and E7 of HPV16 (HPV16-SLP) that represents the entire length of these two oncoproteins, and has shown responses in preclinical models as well as in patients with premalignant are used to evaluate immune responses. The CellSqueeze platform is used to load DC with the HPV16-SLP cocktail, which allows peptides to be channeled into both MHC class I and II presentation pathways, and thus induces antigen-specific expansion of CD4 and CD8 T cells.

As such, this approach prompts a multi-epitope response that overcomes the limitations of HLA specific short peptides and enables more effective therapies.

CellSqueezing of HPV16-SLP to Human and Mouse DC.

Different CellSqueeze conditions are tested to deliver the HPV16-SLP cocktail to human and mouse DC. Chip designs having variations in constriction length, constriction width, the number of constrictions and the angle of approach to the constriction are evaluated. With regard to the process parameters, cell concentration, delivery medium, peptide concentration in the delivery medium, processing temperature, operating pressure and the number of passes through the chip are investigated. The experimental approach for the optimization process also includes fluorescent labeling of the HPV16-SLP peptide cocktail to account for the amount of peptide delivery into cells. Moreover, optimal processing and presentation of the peptides is accounted for in the context of class I and II by detecting the presented peptides with TCR specific tetramers by flow cytometry. This approach is compared to the loading of DC with HLA specific Class I short peptides for cross-presentation.

This study identifies chip designs and delivery conditions that efficiently load human and murine DC with the HPV16-SLP peptide antigens or mixtures of antigens, e.g., a cocktail of viral antigens, e.g., including conditions for efficient processing of long peptides and loading of antigens by APCs, e.g., dendritic cells.

In Vitro and In Vivo Assessment of the .otenc of HPV 6-SLP squeezed DC to Expand Antigen Specific T Cells.

The function of DC loaded with the peptide cocktail under several conditions for their ability to expand antigen specific T cells is tested. For example, antigen-specific T cells are induced by immunizing mice with HPV16-SLP and CpG. Eight days after boosting, T cells are isolated from spleens of immunized mice and are used to co-culture with HPV16-SLP loaded DC in order to determine the capability of loaded cells to trigger antigen-specific CD4 and CD8 T cell expansion and cytokine production. In order to test the human loaded DC, human T cell clones reactive to HPV16 are used to co-culture with human DC loaded with the HPV16-SLP cocktail under several conditions. Antigen-specific T cell expansion and cytokine production are assessed. Whether human and/or mouse loaded DC are functional and capable of expanding antigen-specific T cells is tested in vitro. DC loaded with HLA specific Class I short peptides are used as controls. HLA matching T cells are used as responders.

Thereafter and to test for the effectiveness of the CellSqueeze DC-based vaccine to generate anti-tumor responses against HPV-16 in vivo, mice are vaccinated with HPV16-SLP loaded DC and challenged with TC1 tumors (retrovirally transduced lung fibroblast of C57BL/6 mice with HPV E6 and E7, and c-H-ras oncogenes). Survival of the challenged mice is the readout.

These studies show that a DC-based vaccine generated with CellSqueeze technology triggers protective anti-tumor T cell and/or anti-viral responses in vivo.

OTHER EMBODIMENTS

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference. While this invention has been particularly shown and described with references to preferred embodiments thereof, it will be understood by those skilled in the art that various changes in form and details may be made therein without departing from the scope of the invention encompassed by the appended claims.

The invention claimed is:

1. A method for engineering of immune cell function in an immune cell comprising intracellular delivery of a compound by passing a suspension comprising said immune cell through a microfluidic device comprising a constriction and contacting the immune cell with said compound to deliver said compound into the cytosol of said immune cell, wherein the constriction has a diameter of 2 μm to 10 μm, and wherein said compound:
  a) comprises a differentiation factor, a self-amplifying RNA that encodes for continual production of an encoded protein, a chimeric antigen receptor, a nucleic acid encoding a chimeric antigen receptor, a tolerogenic factor, an adjuvant, a virus, a virus-like particle, a nucleic acid that is a plasmid, a nucleic acid that is a transposon, or a nucleic acid that encodes an MHC complex; or
  b) confers the expression of a homing phenotype to the immune cell; or
  c) induces the differentiation of the immune cell into a cell with a tolerogenic phenotype; or
  d) enhances immune cell function, wherein the immune cell is a T cell, and wherein the compound that enhances T cell function is an immune checkpoint pathway inhibitor.

2. The method of claim 1, wherein the compound comprises a differentiation factor.

3. The method of claim 1, wherein said membrane is disrupted by passing said immune cell through a constriction having a diameter of 3 μm to 6 μm.

4. The method of claim 1, wherein said immune cell is a T cell, B cell, dendritic cell, macrophage, NK cell, monocyte, neutrophil, granulocyte, or innate lymphoid cell.

5. The method of claim 1, wherein said compound confers the expression of a homing phenotype to the immune cell.

6. The method of claim 1, wherein said compound induces the differentiation of the immune cell into a cell with a tolerogenic phenotype.

7. The method of claim 1 wherein said compound comprises a self-amplifying RNA that encodes for continual production of an encoded protein.

8. The method of claim 1, further comprising contacting said immune cell with an effector T cell and activating a cytotoxic T cell immune response.

9. The method of claim 1, further comprising contacting said immune cell with an effector T cell and activating a helper T cell immune response.

10. The method of claim 1, further comprising contacting said immune cell with an effector T cell and activating a tolerogenic T cell immune response.

11. The method of claim 1, wherein said compound comprises a chimeric antigen receptor.

12. The method of claim 11, wherein the chimeric antigen receptor is a chimeric T cell receptor.

13. The method of claim 1, wherein said compound enhances immune cell function.

14. The method of claim 13, wherein the immune cell is a T cell.

15. The method of claim 14, wherein the compound that enhances T cell function is an immune checkpoint pathway inhibitor.

16. The method of claim 1, wherein said compound comprises a tolerogenic factor.

17. The method of claim 1, wherein said compound comprises an adjuvant.

18. The method of claim 1, wherein said compound comprises a nucleic acid.

19. The method of claim 18, wherein said nucleic acid is or encodes an siRNA, mRNA, miRNA, lncRNA, tRNA, saRNA, or shRNA.

20. The method of claim 18, wherein said nucleic acid is a plasmid.

21. The method of claim 1, wherein the compound comprises a protein or peptide.

22. The method of claim 1, wherein the compound comprises a virus.

23. The method of claim 18, wherein the nucleic acid encodes an MHC complex.

24. The method of claim 1, wherein said immune cell is in a resting state.

25. The method of claim 24, wherein expression of one or more of the markers CD25, KLRG1, CD80, CD86, PD-1, PDL-1, CTLA-4, CD28, CD3, MHC-I, MHC-II, CD62L, CCR7, CX3CR1 or CXCR5 in the immune cell is modulated by delivery of said compound into said immune cell.

26. The method of claim 25, wherein expression of one or more of the markers is decreased and/or expression of one or more of the markers is increased.

27. The method of claim 1, wherein said immune cell is a naive immune cell or a memory immune cell.

28. The method of claim 1, wherein said cell suspension comprises whole blood, buffy coat cells, a mixed cell population, or a purified cell population.

29. The method of claim 1, wherein said cell suspension comprises peripheral blood mononuclear cells, and wherein the compound is delivered to a peripheral blood mononuclear cell of the cell suspension.

30. The method of claim 1, wherein said cell suspension comprises mammalian cells.

31. The method of claim 30, wherein said cell suspension comprises human, mouse, dog, cat, horse, monkey, or rat cells.

32. The method of claim 1, wherein said compound comprises a nucleic acid encoding a chimeric antigen receptor.

33. The method of claim 32, wherein the chimeric antigen receptor is a chimeric T cell receptor.

34. The method of claim 1, wherein said compound comprises a virus-like particle.

35. The method of claim 1, wherein said nucleic acid is a transposon.

36. The method of claim 29, wherein the peripheral blood mononuclear cells comprise one or more of the following types of cells: T cells, B cells, NK cells, monocytes, dendritic cells, and macrophages.

37. The method of claim 29, wherein the peripheral blood mononuclear cells comprise a T cell.

38. The method of claim 29, wherein the peripheral blood mononuclear cells comprise a B cell.

39. The method of claim 29, wherein the peripheral blood mononuclear cells comprise an NK cell.

40. The method of claim 29, wherein the peripheral blood mononuclear cells comprise a monocyte.

41. The method of claim 29, wherein the peripheral blood mononuclear cells comprise a dendritic cell.

42. The method of claim 29, wherein the peripheral blood mononuclear cells comprise a macrophage.

43. The method of claim 37, wherein the compound comprises a chimeric antigen receptor.

44. The method of claim 37, wherein the compound comprises a nucleic acid encoding a chimeric antigen receptor.

45. The method of claim 37, wherein the compound comprises a nucleic acid that is a transposon.

46. The method of claim 37, wherein the compound enhances T cell function, and wherein the compound that enhances T cell function is an immune checkpoint pathway inhibitor.

47. The method of claim 37, wherein the compound comprises a virus or virus-like particle.

48. A method for engineering of immune cell function in an immune cell comprising intracellular delivery of a compound by passing a suspension comprising said immune cell through a microfluidic device comprising a constriction and contacting the immune cell with said compound to deliver said compound into the cytosol of said immune cell, wherein the constriction has a diameter of 2 µm to 10 µm, and wherein said compound comprises:
   a) an antigen that comprises a full-length, unprocessed protein; or
   b) a tumor antigen or viral antigen selected from the group consisting of liver cancer antigen, lung cancer antigen, bladder cancer antigen, breast cancer antigen, colon cancer antigen, rectal cancer antigen, endometrial cancer antigen, kidney cancer antigen, leukemia antigen, melanoma antigen, non-Hodgkin lymphoma antigen, pancreatic cancer antigen, prostate cancer antigen, thyroid cancer antigen, ovarian cancer antigen, uterine cancer antigen, HIV antigen, Ebola antigen, HPV antigen, and EBV antigen.

49. The method of claim 48, wherein said compound comprises an antigen having a length of greater than 7, 8, 9 or 10 amino acids and wherein said immune cell processes said antigen and displays a class I histocompatibility antigen restricted processed form of said antigen on a surface of said immune cell.

50. The method of claim 48, wherein the compound comprises an antigen, and wherein said immune cell processes said antigen and displays said antigen on a surface of said immune cell.

51. The method of claim 50, wherein the immune cell displays a class I or class II histocompatibility antigen restricted processed form of said antigen on a surface of said immune cell.

52. The method of claim 48, wherein said membrane is disrupted by passing said immune cell through a constriction having a diameter of 3 µm to 6 µm.

53. The method of claim 48, wherein said immune cell is a T cell, B cell, dendritic cell, macrophage, NK cell, monocyte, neutrophil, granulocyte, or innate lymphoid cell.

54. The method of claim 48, further comprising intracellular delivery of a compound that induces the differentiation of the immune cell into a cell with a tolerogenic phenotype.

55. The method of claim 48, wherein said antigen comprises a full-length, unprocessed protein.

56. The method of claim 48, further comprising contacting said immune cell with an effector T cell and activating a cytotoxic T cell immune response.

57. The method of claim 48, further comprising contacting said immune cell with an effector T cell and activating a helper T cell immune response.

58. The method of claim 48, further comprising contacting said immune cell with an effector T cell and activating a tolerogenic T cell immune response.

59. The method of claim 48, wherein said compound comprises a disease-associated antigen.

60. The method of claim 55, wherein said compound comprises a tumor antigen, viral antigen, bacterial antigen, self-antigen, or fungal antigen.

61. The method of claim 48, wherein said compound comprises a liver cancer antigen, lung cancer antigen, bladder cancer antigen, breast cancer antigen, colon cancer antigen, rectal cancer antigen, endometrial cancer antigen, kidney cancer antigen, leukemia antigen, melanoma antigen, non-Hodgkin lymphoma antigen, pancreatic cancer antigen, prostate cancer antigen, thyroid cancer antigen, ovarian cancer antigen, or uterine cancer antigen.

62. The method of claim 48, wherein said compound comprises a tumor cell lysate or cell lysate from tissue infected with a pathogen.

63. The method of claim 48, wherein said compound comprises a neoantigen.

64. The method of claim 48, wherein said compound comprises an HIV antigen, Ebola antigen, HPV antigen, or EBV antigen.

65. The method of claim 48, further comprising intracellular delivery of a compound that enhances immune cell function.

66. The method of claim 48, wherein the immune cell is a T cell.

67. The method of claim 66, further comprising intracellular delivery of a compound that enhances T cell function.

68. The method of claim 67, wherein the compound that enhances T cell function is an immune checkpoint pathway inhibitor.

69. The method of claim 48, further comprising intracellular delivery of a tolerogenic factor.

70. The method of claim 48, further comprising intracellular delivery of an adjuvant.

71. The method of claim 61, wherein the compound comprises a protein or peptide.

72. The method of claim 48, wherein the compound comprises a virus or virus-like particle.

73. The method of claim 48, wherein said immune cell is in a resting state.

74. The method of claim 73, wherein expression of one or more of the markers CD25, KLRG1, CD80, CD86, PD-1, PDL-1, CTLA-4, CD28, CD3, MHC-I, MHC-II, CD62L, CCR7, CX3CR1 or CXCR5 in the immune cell is modulated by delivery of said compound into said immune cell.

75. The method of claim 74, wherein expression of one or more of the markers is decreased and/or expression of one or more of the markers is increased.

76. The method of claim 48, wherein said immune cell is a naive immune cell or a memory immune cell.

77. The method of claim 48, wherein said cell suspension comprises whole blood, buffy coat cells, a mixed cell population, or a purified cell population.

78. The method of claim 48, wherein said cell suspension comprises peripheral blood mononuclear cells, and wherein the compound is delivered to a peripheral blood mononuclear cell of the cell suspension.

79. The method of claim 48, wherein said cell suspension comprises mammalian cells.

80. The method of claim 79, wherein said cell suspension comprises human, mouse, dog, cat, horse, monkey, or rat cells.

81. The method of claim 48, wherein said compound comprises a liver cancer antigen.

82. The method of claim 48, wherein said compound comprises a lung cancer antigen.

83. The method of claim 48, wherein said compound comprises a bladder cancer antigen.

84. The method of claim 48, wherein said compound comprises a breast cancer antigen.

85. The method of claim 48, wherein said compound comprises a colon cancer antigen.

86. The method of claim 48, wherein said compound comprises a rectal cancer antigen.

87. The method of claim 48, wherein said compound comprises an endometrial cancer antigen.

88. The method of claim 48, wherein said compound comprises a kidney cancer antigen.

89. The method of claim 48, wherein said compound comprises a leukemia antigen.

90. The method of claim 48, wherein said compound comprises a melanoma antigen.

91. The method of claim 48, wherein said compound comprises a non-Hodgkin lymphoma antigen.

92. The method of claim 48, wherein said compound comprises a pancreatic cancer antigen.

93. The method of claim 48, wherein said compound comprises a prostate cancer antigen.

94. The method of claim 48, wherein said compound comprises a thyroid cancer antigen.

95. The method of claim 48, wherein said compound comprises an ovarian cancer antigen.

96. The method of claim 48, wherein said compound comprises a uterine cancer antigen.

97. The method of claim 48, wherein said compound comprises an HIV antigen.

98. The method of claim 48, wherein said compound comprises an Ebola antigen.

99. The method of claim 48, wherein said compound comprises an HPV antigen.

100. The method of claim 48, wherein said compound comprises an EBV antigen.

101. The method of claim 64, wherein the compound comprises a protein or peptide.

102. The method of claim 78, wherein the peripheral blood mononuclear cells comprise one or more of the following types of cells: T cells, B cells, NK cells, monocytes, dendritic cells, and macrophages.

103. The method of claim 78, wherein the peripheral blood mononuclear cells comprise a T cell.

104. The method of claim 78, wherein the peripheral blood mononuclear cells comprise a B cell.

105. The method of claim 78, wherein the peripheral blood mononuclear cells comprise an NK cell.

106. The method of claim 78, wherein the peripheral blood mononuclear cells comprise a monocyte.

107. The method of claim 78, wherein the peripheral blood mononuclear cells comprise a dendritic cell.

108. The method of claim 78, wherein the peripheral blood mononuclear cells comprise a macrophage.

109. The method of claim 103, further comprising intracellular delivery of a compound that enhances immune cell function.

110. The method of claim 103, further comprising intracellular delivery of a compound that enhances T cell function.

111. The method of claim 110, wherein the compound that enhances T cell function is an immune checkpoint pathway inhibitor.

112. The method of claim 103, further comprising intracellular delivery of a tolerogenic factor.

113. The method of claim 103, further comprising intracellular delivery of an adjuvant.

114. A method for engineering of immune cell function in an immune cell comprising intracellular delivery of a compound by passing a suspension comprising said immune cell through a microfluidic device comprising a constriction and contacting the immune cell with said compound to deliver said compound into the cytosol of said immune cell, wherein the constriction has a diameter of 2 μm to 10 μm, wherein the compound comprises a protein comprising a TALEN protein, Zinc finger nuclease, or transcription factor.

115. The method of claim 114, wherein the immune cell displays a class I or class II histocompatibility antigen restricted processed form of an antigen on a surface of said immune cell.

116. The method of claim 114, wherein said membrane is disrupted by passing said immune cell through a constriction having a diameter of 3 μm to 6 μm.

117. The method of claim 114, wherein said immune cell is a T cell, B cell, dendritic cell, macrophage, NK cell, monocyte, neutrophil, granulocyte, or innate lymphoid cell.

118. The method of claim 114, wherein said compound confers the expression of a homing phenotype to the immune cell.

119. The method of claim 114, wherein said compound induces the differentiation of the immune cell into a cell with a tolerogenic phenotype.

120. The method of claim 114, further comprising contacting said immune cell with an effector T cell and activating a cytotoxic T cell immune response.

121. The method of claim 114, further comprising contacting said immune cell with an effector T cell and activating a helper T cell immune response.

122. The method of claim 114, further comprising contacting said immune cell with an effector T cell and activating a tolerogenic T cell immune response.

123. The method of claim 114, wherein said compound enhances immune cell function.

124. The method of claim 123, wherein the immune cell is a T cell.

125. The method of claim 124, wherein the compound that enhances T cell function is an immune checkpoint pathway inhibitor.

126. The method of claim 114, wherein said compound comprises a tolerogenic factor.

127. The method of claim 114, wherein the compound comprises a peptide.

128. The method of claim 114, wherein said immune cell is in a resting state.

129. The method of claim 128, wherein expression of one or more of the markers CD25, KLRG1, CD80, CD86, PD-1, PDL-1, CTLA-4, CD28, CD3, MHC-I, MHC-II, CD62L, CCR7, CX3CR1 or CXCR5 in the immune cell is modulated by delivery of said compound into said immune cell.

130. The method of claim 129, wherein expression of one or more of the markers is decreased and/or expression of one or more of the markers is increased.

131. The method of claim 114, wherein said immune cell is a naive immune cell or a memory immune cell.

132. The method of claim 114, wherein said cell suspension comprises whole blood, buffy coat cells, a mixed cell population, or a purified cell population.

133. The method of claim 114, wherein said cell suspension comprises peripheral blood mononuclear cells, and wherein the compound is delivered to a peripheral blood mononuclear cell of the cell suspension.

134. The method of claim 114, wherein said cell suspension comprises mammalian cells.

135. The method of claim 134, wherein said cell suspension comprises human, mouse, dog, cat, horse, monkey, or rat cells.

136. The method of claim 114, wherein the compound comprises a protein comprising a TALEN protein.

137. The method of claim 114, wherein the compound comprises a protein comprising a Zinc finger nuclease.

138. The method of claim 114, wherein the compound comprises a protein comprising a transcription factor.

139. The method of claim 133, wherein the peripheral blood mononuclear cells comprise one or more of the following types of cells: T cells, B cells, NK cells, monocytes, dendritic cells, and macrophages.

140. The method of claim 133, wherein the peripheral blood mononuclear cells comprise a T cell.

141. The method of claim 133, wherein the peripheral blood mononuclear cells comprise a B cell.

142. The method of claim 133, wherein the peripheral blood mononuclear cells comprise an NK cell.

143. The method of claim 133, wherein the peripheral blood mononuclear cells comprise a monocyte.

144. The method of claim 133, wherein the peripheral blood mononuclear cells comprise a dendritic cell.

145. The method of claim 133, wherein the peripheral blood mononuclear cells comprise a macrophage.

\* \* \* \* \*